(12) United States Patent
Volkamer et al.

(10) Patent No.: US 10,379,194 B2
(45) Date of Patent: Aug. 13, 2019

(54) MOBILE DEVICES FOR TRACKING A RADIATION DISK LIGHT SOURCE AND METHODS USING SAME

(71) Applicant: THE REGENTS OF THE UNIVERSITY OF COLORADO, A BODY CORPORATE, Denver, CO (US)

(72) Inventors: Rainer Volkamer, Boulder, CO (US); Sunil Baidar, Denver, CO (US); David Thomson, Boulder, CO (US)

(73) Assignee: The Regents of the University of Colorado, a body corporate, Denver, CO (US)

( * ) Notice: Subject to any disclaimer, the term of this patent is extended or adjusted under 35 U.S.C. 154(b) by 146 days.

(21) Appl. No.: 15/713,106

(22) Filed: Sep. 22, 2017

(65) Prior Publication Data

US 2018/0088204 A1  Mar. 29, 2018

Related U.S. Application Data

(60) Provisional application No. 62/398,852, filed on Sep. 23, 2016.

(51) Int. Cl.
| | |
|---|---|
| *G01S 3/786* | (2006.01) |
| *G01S 3/781* | (2006.01) |
| *G01S 3/789* | (2006.01) |
| *G01S 3/783* | (2006.01) |
| *G01N 21/31* | (2006.01) |
| *G01N 21/3504* | (2014.01) |
| *G01N 21/35* | (2014.01) |

(52) U.S. Cl.
CPC ............ *G01S 3/7862* (2013.01); *G01N 21/31* (2013.01); *G01S 3/781* (2013.01); *G01S 3/783* (2013.01); *G01S 3/789* (2013.01); *G01N 2021/3531* (2013.01); *G01N 2021/3595* (2013.01)

(58) Field of Classification Search
CPC ........ G01S 3/7862; G01S 3/781; G01S 3/783; G01S 3/789; G01N 21/31; G01N 2021/3595; G01N 2021/3531
USPC ..................................................... 250/203.4
See application file for complete search history.

(56) References Cited

U.S. PATENT DOCUMENTS

| | | | |
|---|---|---|---|
| 7,501,629 B2 * | 3/2009 | Hashmonay | G01N 21/3504 250/339.08 |
| 8,178,775 B2 * | 5/2012 | Taylor, II | G01S 3/7861 136/246 |

OTHER PUBLICATIONS

Baidar, S. et al., "Combining Active and Passive Airborne Remote Sensing to Quantify NO2 and Ox Production near Bakersfield, CA," British J Environ & Climate Change, vol. 3(4), 2013, pp. 566-586.
(Continued)

*Primary Examiner* — Seung C Sohn
(74) *Attorney, Agent, or Firm* — Saul Ewing Arnstein & Lehr LLP; Kathryn Doyle; Domingos J. Silva

(57) ABSTRACT

The invention provides in one aspect a fast digital light source tracker aboard a moving ground-based or airborne platform. The tracker consists of two rotating mirrors, a lens, an imaging camera, and a motion compensation system that provides the Euler angles of the mobile platform in real time. The tracker can be simultaneously coupled to UV-Vis and FTIR spectrometers, making it a versatile tool to measure the absorption of trace gases using the light source's incoming radiation.

19 Claims, 41 Drawing Sheets
(39 of 41 Drawing Sheet(s) Filed in Color)

(56) References Cited

OTHER PUBLICATIONS

Baidar, S. et al., "Development of a digital mobile solar tracker," Atmos Meas Tech, 9, 2016, pp. 963-972.
Baidar, S. et al., "The CU Airborne MAX-DOAS instrument: vertical profiling of aerosol extinction and trace gases," Atmos Meas Tech, 6, 2013, pp. 719-739.
Coburn, S. et al., "The CU ground MAX-DOAS instrument: characterization of RMS noise limitations and first measurements near Pensacola, FL of BrO, IO, and CHOCHO," Atmos Meas Tech, 4, 2011, pp. 2421-2439.
Frins, E. et al., "Determination of NOx emissions from Frankfurt Airport by optical spectroscopy (DOAS)—A feasibility study," Atmos Meas Tech Discuss, 2016, pp. 1-18.
Liu, F. et al., "NOx lifetimes and emissions of cities and power plants in polluted background estimated by satellite observations," Atmos Chem Phys, 16, 2016, pp. 5283-5298.
Mellqvist, J. et al., "Measurements of industrial emissions of alkenes in Texas using the solar occultation flux method," Journal of Geophysical Res, vol. 115, 2010, pp. D00F17-1-13.

\* cited by examiner

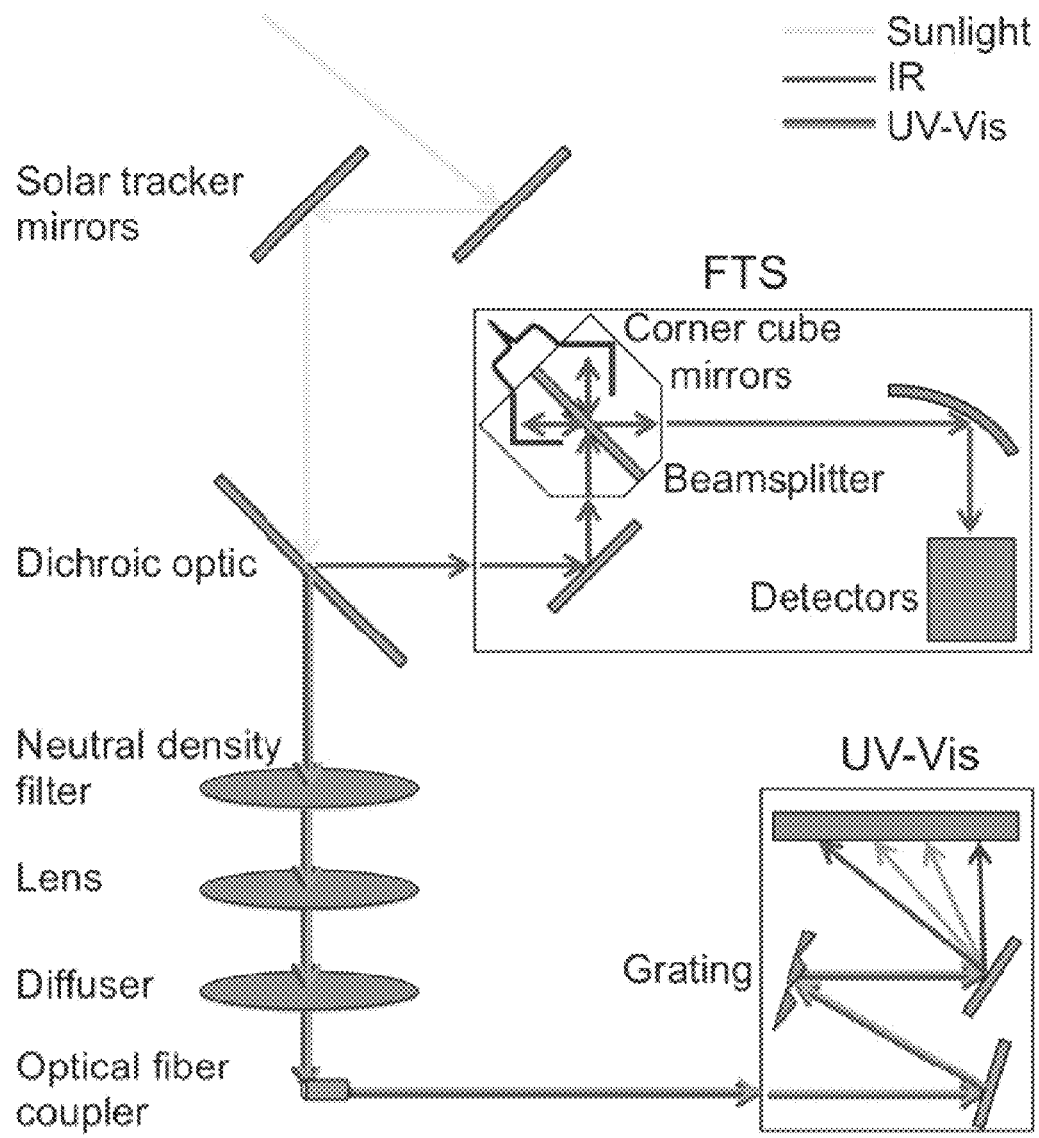

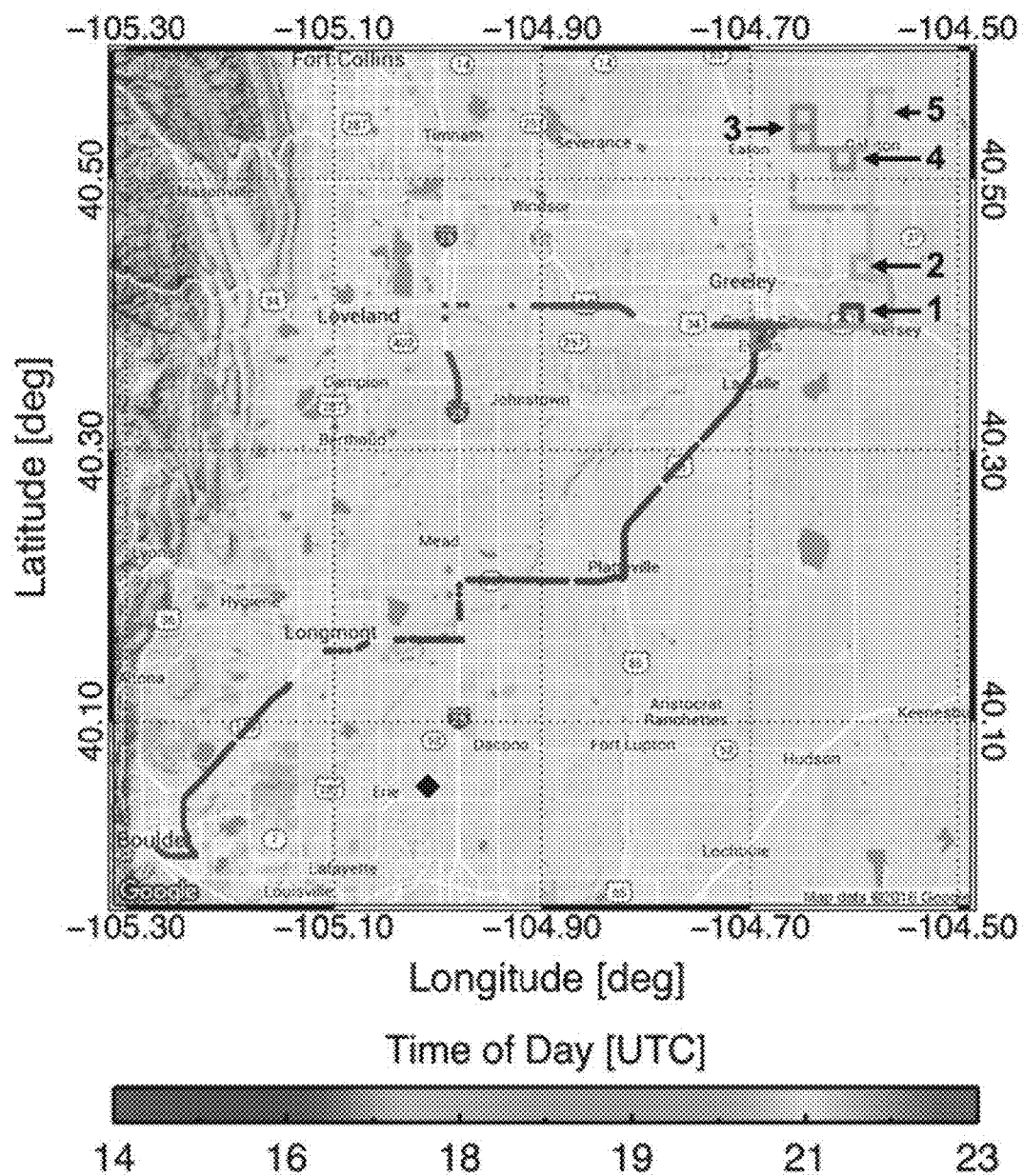

MOBILE DEVICES FOR TRACKING A RADIATION DISK LIGHT SOURCE AND METHODS USING SAME

CROSS-REFERENCE TO RELATED APPLICATIONS

This application claims the benefit of priority under 35 U.S.C. § 119(e) of U.S. Provisional Patent Application No. 62/398,852, filed Sep. 23, 2016, the entire disclosure of which is hereby incorporated herein by reference.

BACKGROUND OF THE INVENTION

Mobile column measurements provide a means to characterize the distribution of trace gases over a large spatial scale while capturing the atmospheric variability over the column. Combined with wind measurements, mobile column measurements of trace gases have been shown to be very useful to constrain emission of trace gases from source regions by applying a mass conservation approach. Mobile column measurements from various platforms have previously been used to estimate: nitrogen oxides ($NO_x$) emissions from cities; nitrogen dioxide ($NO_2$), sulfur dioxide ($SO_2$), and formaldehyde (HCHO) emissions from industries using the differential optical absorption spectroscopy (DOAS) technique; and fugitive volatile organic compound (VOC) emissions from refineries using the solar occultation flux (SOF) method. The DOAS method typically is limited to the UV-Vis wavelength region and uses scattered sunlight; while the SOF method uses direct sun observations in the mid-IR wavelengths.

DOAS measurements of scattered sunlight are particularly attractive for mobile column measurements, because scattered sunlight measurements do not require clear-sky conditions and because of the relative ease of operating such instruments. In particular, the stability of the elevation angle (EA), i.e., angle relative to the horizon, is less crucial at higher EAs typically used for mobile DOAS measurements. However, logistical challenges arise when measurements observe the direct solar beam from a moving platform, e.g., due to highly uncorrelated motions of vehicles on roads.

There is thus a need in the art for devices and techniques for detecting and measuring gas emissions in a vertical column using light source beams, from an unstable, moving platform. The present invention addresses this need.

BRIEF SUMMARY OF THE INVENTION

In one aspect, the invention provides a mobile radiation disk light source tracker system mounted on a platform. In another aspect, the invention also provides a method of tracking an incoming radiation disk light source position on a continuous basis from a platform. In yet another aspect, the invention provides a computer-implemented method of operating the mobile tracker system of the invention.

In certain embodiments, the system comprises a first stepper motor and a second stepper motor. In other embodiments, the system comprises a first mirror, wherein the first mirror is mounted at a 45° angle on the first stepper motor. In yet other embodiments, the system comprises a second mirror, which is mounted at a 45° angle opposite from the first mirror. In yet other embodiments, the =first and second mirrors are mounted onto a rotational stage that is coupled with the second stepper motor, wherein the rotational stage allows for 360° rotation of the first and second mirrors. In yet other embodiments, the system comprises a lens and an aperture plate, which are set up such that light source incoming radiation that is reflected by the first mirror onto the second mirror is then reflected by second mirror onto the lens. In yet other embodiments, the lens focuses the incoming radiation disk onto a front side of the aperture plate. In yet other embodiments, the system comprises a motion compensation system that measures in real time the pitch, roll and heading information (Euler Angles) of the platform, which is used to calculate the light source position relative to the platform in real time. In yet other embodiments, the system comprises an imaging monitoring system that is capable of measuring the position of the incoming radiation disk focused onto the front side of the aperture plate. In yet other embodiments, the first and second stepper motors are controlled to ensure that the incoming radiation focused onto the front side of the aperture plate is within the imaging device's field of view.

In certain embodiments, the light source is selected from the group consisting of the Sun, the Moon, and an artificial disk-like light source. In other embodiments, the light source is the Sun. In yet other embodiments, the monitoring system is a camera.

In certain embodiments, a UV-vis spectrometer is located on the opposite side of the aperture plate. In other embodiments, a diffuser is located between the opposite side of the aperture plate and the UV-vis spectrometer. In yet other embodiments, a dichroic mirror is located between the second mirror and the lens, and wherein the dichroic mirror is positioned at an angle of 45° with respect to the incoming beam. In yet other embodiments, the dichroic mirror directs infrared radiation to a IR spectrometer.

In certain embodiments, the motion compensation system comprises at least one angle sensor. In other embodiments, the at least one angle sensor comprises a GPS-based inertial navigation system and/or an inclinometer.

In certain embodiments, the method comprises monitoring the position of the light source from the platform using the mobile radiation tracker of the invention.

In certain embodiments, the method comprises using heading, pitch and roll angle (Euler Angles) information of the platform to calculate an incoming radiation disk light source position relative to the platform orientation in real time. In other embodiments, the method comprises controlling the first and second stepper motors such that the incoming radiation focused onto the front side of the aperture plate is within the imaging device's field of view.

In certain embodiments, the method comprises recording and evaluating incoming radiation disk images to determine the relative center positions of the aperture and the incoming radiation disk, in order to determine if the incoming radiation focused onto the front side of the aperture plate is within the imaging device's field of view. In other embodiments, a threshold is applied to convert incoming radiation disk images to binary format contours. In yet other embodiments, the incoming radiation disk images are distinguished from the aperture plate and aperture which are not exposed to the incoming radiation. In yet other embodiments, the binary format contours are subjected to an ellipse- or circle-fitting algorithm. In yet other embodiments, the position of the fitted ellipse or circle center is determined relative to the aperture. In yet other embodiments, the position of the fitted ellipse or circle center relative to the aperture is corrected for any motion observed between measurements. In yet other embodiments, the relative position of the fitted ellipse or circle center is used to optimize the light source tracking precision.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The following detailed description of specific embodiments of the invention will be better understood when read in conjunction with the appended drawings. For the purpose of illustrating the invention, specific embodiments are shown in the drawings. It should be understood, however, that the invention is not limited to the precise arrangements and instrumentalities of the embodiments shown in the drawings.

FIGS. 2A-2E depict an illustrative non-limiting instrumental setup of the Euler Angle based tracking apparatus. FIGS. 2A-2B are photographs depicting the digital solar tracker apparatus mounted inside the roof hatch of the mobile laboratory. FIGS. 2C-2D are schematic representations of the solar tracker apparatus, both including a camera (FIG. 2C) and without a camera (FIG. 2D). FIG. 2E is a processed image of the solar disk on the aperture plate showing fitted circles (green). The red circles show the search region for the circle fitting algorithm.

FIG. 20 is a map of research drive track of RD11 to investigate agricultural sources near Greeley, Colo. Sites 1, 4 and 5 are dairy farms, 2 is a beef farm and 3 is a sheep farm. The diamond indicates the location of the BAO tower.

FIG. 24A shows maps of the five sites of interest. FIG. 24B shows site 1 and time series graphs of the flux, calculated using Eq. 1.

FIG. 24C shows site 2 and time series graphs of the flux, calculated using Eq. 1. Arrows indicate mean wind direction at each site.

FIG. 25A shows maps of the five sites of interest. FIG. 25B shows site 1 and time series graphs of the flux, calculated using Eq. 1.

FIG. 25C shows site 2 and time series graphs of the flux, calculated using Eq. 1. Arrows indicate mean wind direction at each site.

DETAILED DESCRIPTION OF THE INVENTION

Figure 1:
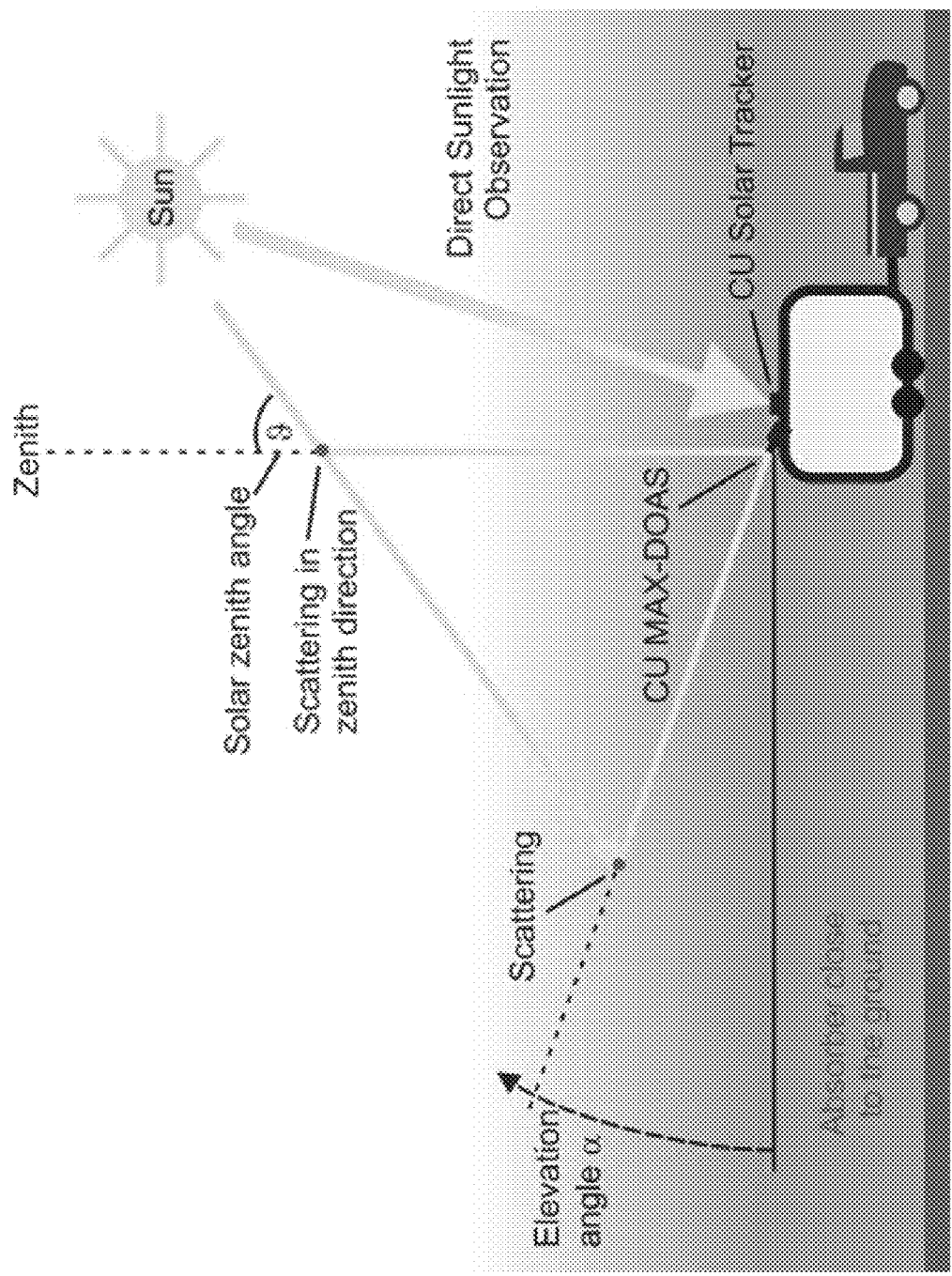
FIG. 1 is an illustration of the measurement principles of the mobile digital (Euler Angle based) light source tracker apparatus and the MAX-DOAS aboard the mobile laboratory.

The invention provides, in one aspect, a fast digital (Euler Angle-based) incoming radiation disk light source tracker aboard a moving platform. A moving platform is defined as any kind of platform that is not stationary over time; it may be, for example, ground-bound or airborne. The tracker consists of two rotating mirrors, a lens, an imaging camera, and a motion compensation system that provides the Euler angles of the mobile platform in real time. The tracker can be simultaneously coupled to UV-Vis and IR spectrometers, making it a versatile tool to measure the absorption of trace gases using light source incoming radiation. The integrated system allows the tracker to operate autonomously while the mobile laboratory is in motion. In an illustrative non-limiting example, mobile direct sun Differential Optical Absorption Spectroscopy (mobile DS-DOAS) and Solar Occultation Flux (SOF) observations using this tracker were conducted. An angular precision of 0.052° (about $\frac{1}{10}$ of the solar disk diameter) was demonstrated during research drives, and this tracking precision was verified from measurements of the center to limb darkening (CLD, the changing appearance of Fraunhofer lines) in the mobile DS-DOAS spectra. The high photon flux from direct sun observation enables measurements of atmospheric trace gases (such as, for example, nitrogen dioxide ($NO_2$) and ammonia ($NH_3$)) slant columns with high temporal resolution, and reveals spatial detail in the variations of the trace gases vertical column densities (VCDs). In an illustrative non-limiting example, the $NO_2$ VCD from DS-DOAS was compared with a co-located MAX-DOAS instrument. Overall good agreement was observed amid a highly heterogeneous air mass.

The use of Euler Angles within the devices and methods of the present invention allow for several advantages over devices and methods of the prior art. The light source tracking devices of the prior art did not have access to Euler Angles at all, or could not continue to correct for vehicle motion if the direct beam was lost. This means, in practice, that in the devices of the prior art when the source beam, such as the Sun, was lost (due to the interception by a visual obstacle, such as but not limited to a tree, a bridge, and/or a cloud), the vehicle had to be stopped and the tracking device had to be realigned. This was time consuming, and in practice limited measurements mostly to clear sky conditions.

The present invention leverages access to the Euler Angles actively, and enables measurements under broken cloud conditions, and that maximizes the duty cycle of measurements, essentially eliminating the need for manual re-alignment, maximizing quality measurements, and saving cost. With the devices of the present invention, if the source beam is lost, the alignment can be accomplished quickly and in a fully automated form (typically within 500 milliseconds). Changes in the vehicle orientation while the sun is lost are always "known" to the software, and the vehicle does not need to be stopped. This eliminates the need for time-consuming search algorithms of the solar disk, or the manual need to re-align the device. The benefit of a higher duty cycle of high-quality measurements, manpower cost savings, and possibility to conduct measurements over a wider range of environmental conditions (e.g., broken clouds), and efficiently from aircraft are consequences of having knowledge of the Euler Angles, and the ability to use them to quickly align the device at all time.

The continuous course tracking of the light source enabled by the Euler Angles of the platform is further refined using the imaging system to improve the tracking precision. High precision tracking of the light sources such as the solar disk presented as a non-limiting example here is required to improve the precision of the trace gas measurements.

The invention provides an Euler angle-based mobile radiation tracker system mounted on a moving platform. In certain embodiments, the system comprises a first stepper motor and a second stepper motor. In other embodiments, the system comprises a first mirror, wherein the first mirror is mounted at a 45° angle on the first stepper motor. In yet other embodiments, the system comprises a second mirror, which is mounted at a 45° angle opposite from the first mirror. In other embodiments, the first and second mirrors are mounted onto a rotational stage that is coupled with the second stepper motor, wherein the rotational stage allows for 360° rotation of the first and second mirrors. In other embodiments, the system comprises a lens and an aperture plate, which are set up such that incoming radiation that is reflected by the first mirror onto the second mirror is then reflected by second mirror onto the lens, wherein the lens focuses the incoming radiation disk onto a front side of the aperture plate. In other embodiments, the system comprises a monitoring system that is capable of measuring the position of the incoming radiation disk focused onto the front side of the aperture plate. In other embodiments, the platform comprises a motion compensation system that provides its Euler angle in real time.

In certain embodiments, the incoming radiation is from a radiation disk light source. In other embodiments, the light source is the Sun, the Moon, or an artificial disk-like light source. In yet other embodiments, the radiation is direct sunlight. In other embodiments, the monitoring system is a camera. In yet other embodiments, the camera is a camera capable of recording images in at least one light spectrum selected from the group consisting of UV-light (wavelengths from about 10 nm to about 400 nm), visible light (wavelengths from about 400 nm to about 750 nm), short wave IR (wavelengths from about 0.75 μm to about 8 μm) and long wave IR (wavelengths from about 8 μm to about 1,000 μm). In yet other embodiments, the use of a non-visible wavelength camera allows for tracking of the light source through visible light obscuring media, such as but not limited to smoke and cloud cover. In yet other embodiments, an UV-vis spectrometer is located on the opposite side of the aperture plate. In yet other embodiments, a diffuser is located between the opposite side of the aperture plate and the UV-vis spectrometer. In yet other embodiments, a dichroic mirror is located between the second mirror and the lens, and wherein the dichroic mirror is positioned at an angle of 45° with respect to the incoming beam. In yet other embodiments, the dichroic mirror directs infrared radiation to an IR spectrometer.

In certain embodiments, the motion compensation system comprises at least one angle sensor to measure heading, pitch and roll angle (Euler Angle) information of the platform. In other embodiments, the at least one angle sensor comprises a GPS-based inertial navigation system and/or an inclinometer. In yet other embodiments, the heading, pitch and roll angle information of the platform are used to calculate celestial/astronomical body position relative to the platform in real time. In yet other embodiments, the first and second stepper motors are controlled to ensure that the incoming radiation focused onto the front side of the aperture plate is within the imaging device's field of view.

The invention further provides a method of tracking a light source position on a continuous basis from a platform (which may be, for example, ground-bound or airborne). In certain embodiments, the method comprises monitoring the position of the light source from the platform using any of the mobile radiation trackers described herein.

The invention further provides a computer-implemented method of operating the mobile tracker systems of the invention. In certain embodiments, the method comprises using heading, pitch and roll angle (Euler Angle) information of the platform to calculate light source (such as astronomical solar) position relative to the platform orientation in real time. In other embodiments, the method comprises controlling the first and second stepper motors such that the incoming radiation focused onto the front side of the aperture plate is within the imaging device's field of view.

In certain embodiments, determining if the incoming radiation focused onto the front side of the aperture plate is within the imaging device's field of view comprises recording and evaluating incoming radiation disk images to determine the relative center positions of the aperture and the incoming radiation disk. In other embodiments, a threshold is applied to convert incoming radiation disk images to binary format contours. In yet other embodiments, the incoming radiation disk images are distinguished from the aperture plate and aperture. In yet other embodiments, the binary format contours are subjected to an ellipse- or circle-fitting algorithm. In yet other embodiments, the position of the fitted ellipse or circle center is determined relative to the aperture. In yet other embodiments, the position of the fitted ellipse or circle center relative to the aperture is corrected for any motion observed between measurements.

Definitions

As used herein, each of the following terms has the meaning associated with it in this section.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, exemplary methods and materials are described.

Generally, the nomenclature used herein and the laboratory procedures in atmospheric chemistry and spectrometry are those well-known and commonly employed in the art.

As used herein, the articles "a" and "an" refer to one or to more than one (i.e., to at least one) of the grammatical object of the article. By way of example, "an element" means one element or more than one element.

As used herein, the term "about" is understood by persons of ordinary skill in the art and varies to some extent on the context in which it is used. As used herein when referring to a measurable value such as an amount, a temporal duration, and the like, the term "about" is meant to encompass variations of ±20% or ±10%, more preferably ±5%, even more preferably ±1%, and still more preferably ±0.1% from the specified value, as such variations are appropriate to perform the disclosed methods.

As used herein, the term "Euler Angle" refers to three angles used to describe the orientation of a rigid body. Euler Angles represent a sequence of three elemental rotations, i.e. rotations about the axes of a coordinate system. For instance, a first rotation about x by an angle α, a second rotation about y by an angle β, and a last rotation again about z, by an angle γ. These rotations start from a known standard orientation.

The following abbreviations are used herein: CCD, Charge coupled device; CLD, Center to limb darkening; dSCD, differential slant column densities; DOAS, Differential optical absorption spectroscopy; DS-DOAS, direct-sun differential optical absorption spectroscopy; EA, Elevation angle; FRAPPE, Front Range Air Pollution and Photochemistry Experiment; FTS, Fourier transform spectrometer; ILS, Instrument line shape; LOD, Limit of detection; $NO_R$, Sum of nitric oxide (NO) and $NO_2$; PBLH, Planetary boundary layer height; SOF, Solar occultation flux; SZA, Solar zenith angle; VCD, Vertical column density; VOC, Volatile organic compound.

It is to be understood that, wherever values and ranges are provided herein, the description in range format is merely for convenience and brevity and should not be construed as an inflexible limitation on the scope of the invention. Accordingly, all values and ranges encompassed by these values and ranges are meant to be encompassed within the scope of the present invention. Moreover, all values that fall within these ranges, as well as the upper or lower limits of a range of values, are also contemplated by the present application. The description of a range should be considered to have specifically disclosed all the possible sub-ranges as well as individual numerical values within that range and, when appropriate, partial integers of the numerical values within ranges. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

The following examples further illustrate aspects of the present invention. However, they are in no way a limitation of the teachings or disclosure of the present invention as set forth herein.

EXAMPLES

The invention is now described with reference to the following Examples. These Examples are provided for the purpose of illustration only, and the invention is not limited to these Examples, but rather encompasses all variations that are evident as a result of the teachings provided herein.

Example 1: Euler Angle Based Mobile Solar Tracker

Figure 2A:
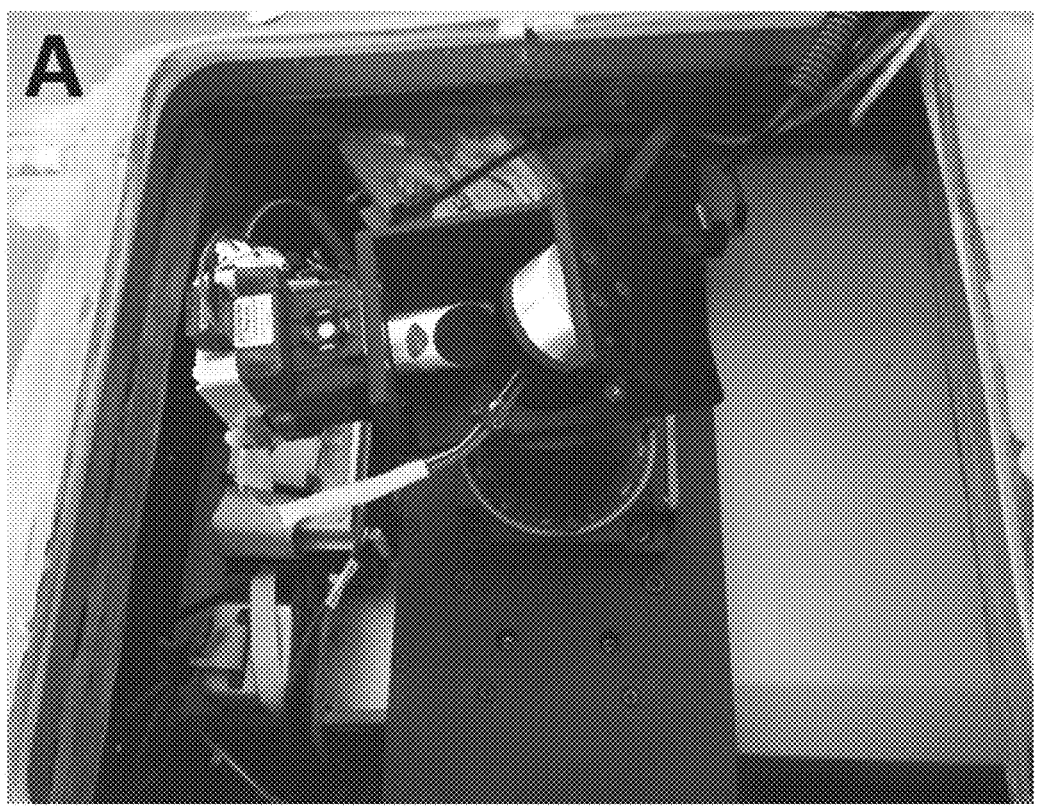
Figure 2B:
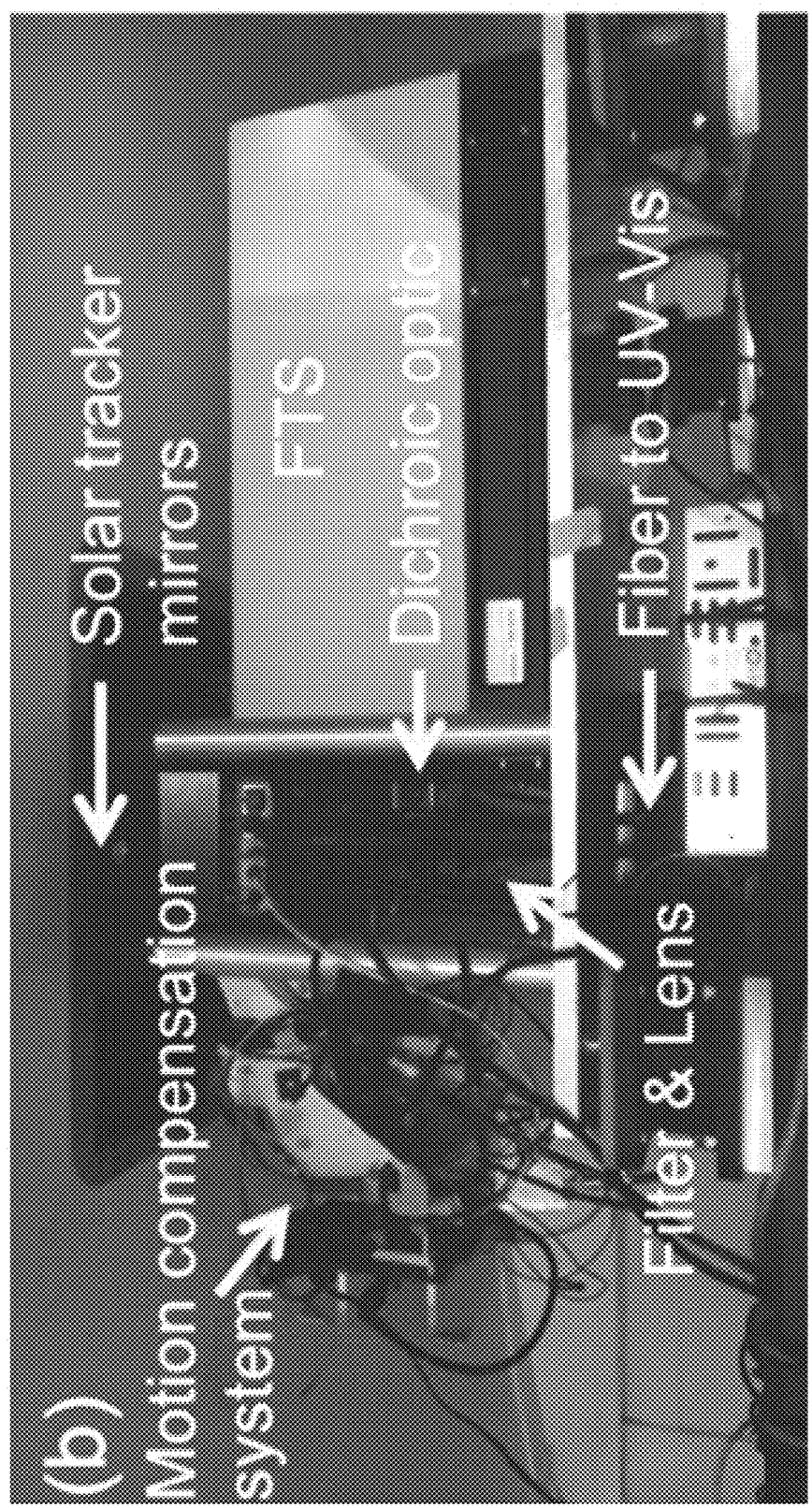
Figure 2C:
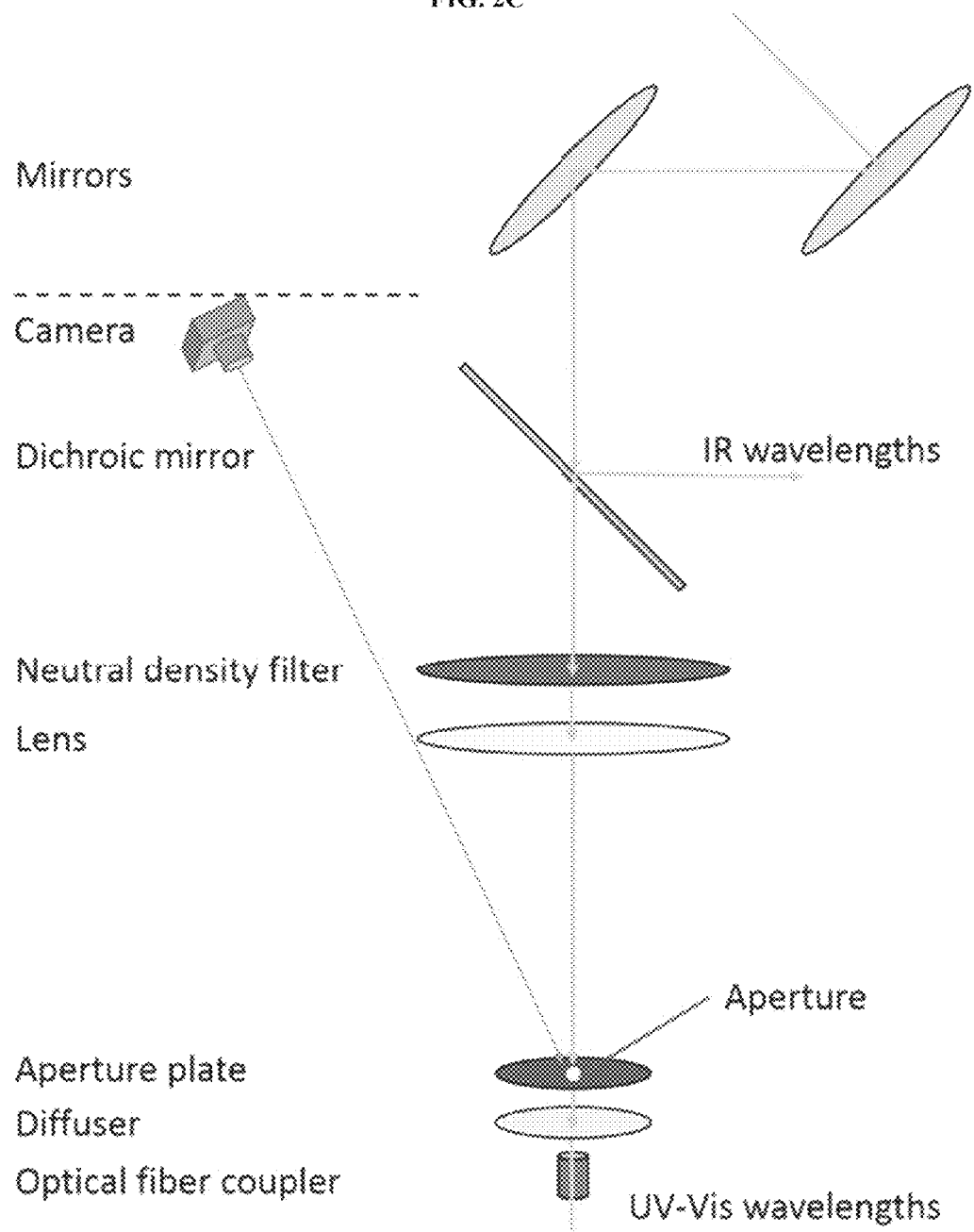

The mobile solar tracker as deployed aboard the mobile laboratory (FIG. 1) is shown in FIGS. 2A-2B in a top-down and side view. The solar tracker is an alt-azimuthal tracker consisting of two mirrors. The first mirror is mounted at a 45° angle directly on a stepper motor and allows access to any EA. The direct coupling of the mirror permits fast backlash free movements. The second mirror is mounted at a 45° angle opposite to the first mirror. The two mirrors are mounted on a rotational stage that is driven by a second stepper motor. The electrical connection is realized via a slip ring that transmits communication and power to the EA motor and permits unrestrained and continuous 360° rotation of the mirror system. The rotational stage and the slip ring have inner (hollow axle) diameters of 2 and 1.5 inches, respectively, that transmits the solar beam. FIGS. 2C and 2D show optical schematics of exemplary embodiments of the solar tracker. The light is focused by a 2 inches f/4 lens onto an aperture plate with a 2 mm diameter hole. A 1.5 mm thick quartz diffuser plate mounted at the back of the aperture plate ensures homogeneous illumination of the UV-Vis spectrometer via a set of optical fibers. The infrared wavelength beam is directed to an IR spectrometer by using a dichroic mirror positioned at an angle of 45° above the lens.

The system comprises a motion compensation system that decouples the telescope field of view from vehicle movements in real time (<0.35° accuracy). The motion compensation system includes angle sensors to measure pitch and roll angles of the vehicle and a feedback loop to correct the telescope position for pitch and roll angles in real time, ensuring constant desired elevation and azimuth angles are maintained during spectra acquisition. Briefly, the system comprises a PC104 computer connected to the two stepper motors of the tracker, two angle sensors, any angle sensor (such as but not limited to Systron Donner Inertial MMQ-G), and an electronic inclinometer. The MMQ-G is a small robust GPS-based inertial navigation system. It provides accurate 3-D position, time, and velocity, as well as heading, pitch, and roll (1σ=0.29° from manufacturer). The pitch, roll, and heading information from the sensor is processed by custom LabVIEW software as Euler angles to calculate the astronomical solar position relative to the real-time vehicle orientation along the drive track. The two mirror angles are then sent to the stepper motors to bring the solar disk into the field of view (FOV) of the imaging camera. Once properly initialized the motion compensation system allows for the automatized operation of the tracker during the drive.

Figure 2E:
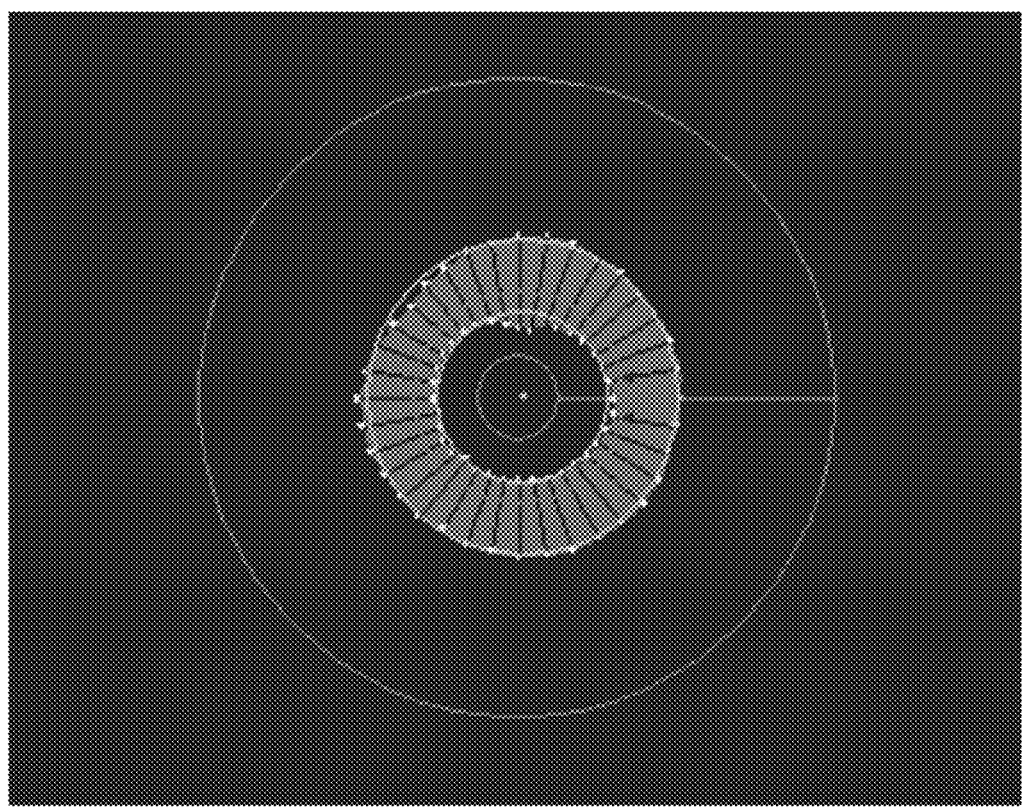

A smart camera with an embedded PC (NATIONAL INSTRUMENTS™ NI-1722, 480×640 pixels, 400 MHz; or NI-1772, 480×640 pixels, 1.6 GHz) is used as an imaging feedback system to monitor and control the pointing of the tracker once the solar disk is in the FOV of the camera. The imaging camera is mounted below the baseplate of the solar tracker at an angle of 20° and has a FOV of 5.2°×3.9°. It is equipped with a standard lens with UV filter (for protection) that observes the image of the solar disk on the aperture plate. During operation, the solar disk has a diameter of about 140 pixels, corresponding to an angular resolution of about 0.0038° per pixel. The 2 mm aperture has a diameter of about 80 pixels. The images are evaluated for the centers of the solar disk and the aperture using a built-in LabVIEW image processing algorithms to determine pixel difference between the centers of the two circles (FIG. 2E). This code runs on the smart camera CPU in real time. The pixel offsets in x and y direction are determined and then sent to the PC104 via a serial data cable for fine tracking of the sun. The loop rate of the tracking system is determined by a combination of image acquisition and determination of offsets by the imaging software (~17-30 ms), communication and angle correction (a few ms), and motor latencies to execute the motor commands (~10-20 ms). In certain non-limiting embodiments, an overall loop rate of 20-30 Hz is realized.

Example 2: Tracking Algorithm

Figure 3:
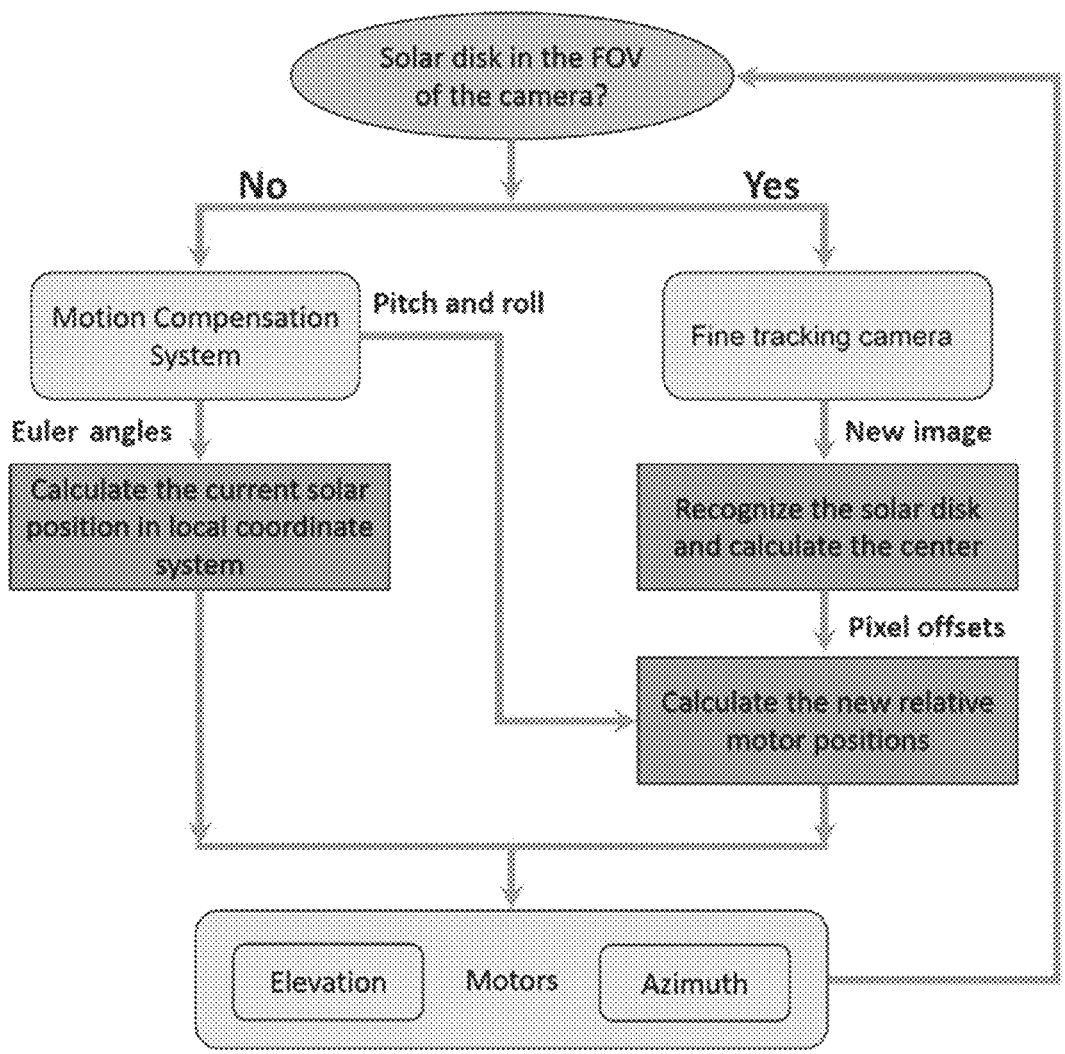
FIG. 3 is an illustrative non-limiting flowchart of the tracking algorithm used with the apparatus of the invention.

The operation of the mobile solar tracker is based on a two-level algorithm as shown in FIG. 3. First, the real-time pitch, roll, and heading information of the platform is used as Euler angles to correct the astronomical solar position and locate the sun in the sky relative to the vehicle orientation. This calculated sun position in the local vehicular coordinate system provides the coarse mirror angles to the motors to bring the solar disk into the FOV of the camera. The solar disk images are recorded and evaluated to determine the center position of the aperture and the solar disk. First, a threshold is applied to convert the image to binary format to distinguish the bright solar disk from the dark aperture plate and aperture. Next, an ellipse fitting algorithm is applied to the binary image contours. For subsequent images, depending on the distance of the solar disk to the aperture, either a circle or an ellipse fitting algorithm is applied. The circle and ellipse algorithms used here are the functions built in to the LabVIEW vision toolkit from National Instruments. The choice of ellipse vs. circle algorithm is made for efficiency, as well as due to limitations of each algorithm. The circle algorithm is significantly faster than the ellipse algorithm, as it only searches for a circle to fit within a well-defined region of the image, centered around the aperture, whereas the ellipse algorithm searches the entire camera pixel space. A consistency check is performed for the radii of fitted circles/ellipses before calculating the difference in the center position of the solar disk and aperture. Once the deviation between the aperture and the solar disk centers is determined from the camera data, a small correction is applied based on historical MMQ data to account for the motion of the platform during the control loop time, i.e., the time from when the picture was recorded until the new motor target position is commanded.

One of the major challenges with tracking the sun from a moving platform is accounting for the platform motion that happens over the course of each control loop interval. As the platform is in continuous uncorrelated motion, the orientation at the time of the recording of the image is different to that when the motor positions are updated. Fast MMQ data at 100 Hz was used to account for this change in orientation and correct the pixel offset data from the imaging system. The correction based on the most recent data from MMQ (t=0) and the data 4 points back in time (t=−40 ms) yielded the best result. The difference in pitch and roll angles between these two points (n=0 and n=−4) and the relationship between degree and pixel is used to correct the pixel offset data from the imaging system. The corrected pixel data are converted to mirror angles to update the mirror positions in order to align the two centers and subsequently keep them aligned. The algorithm that converts x,y pixels to angles has three main components: 1) image analysis to find the error, 2) conversion from pixels to angle to correct the error, and 3) applying the historical pitch and roll correction to improve overall performance.

Figure 4:
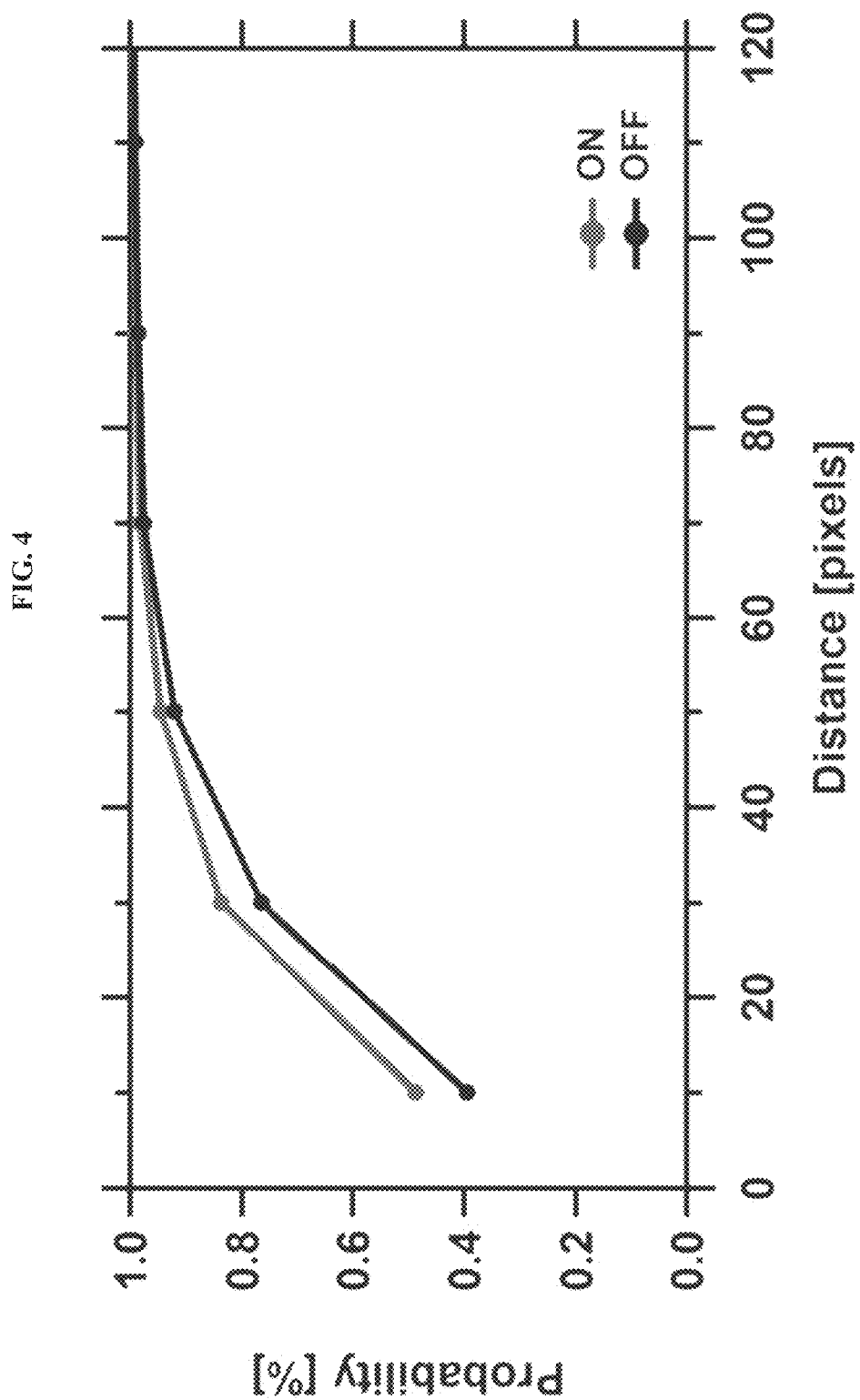
FIG. 4 is a graph of the cumulative distribution of distance (in pixels) between the centers of the solar disk and the aperture for (i) when correction for real time pitch and roll was applied (red) and (ii) correction was not applied (black). An improvement of up to 23% (relative) was observed when the correction based on real time pitch and roll was applied.

Application of this correction for motion of the platform leads to measurable improvements in the tracking during research drives. A cumulative density plot of percentage of points within a certain distance off of the center of the solar disk when this correction is (i) applied and (ii) not applied during segments of a research drive is shown in FIG. 4. An additional 9% of data (a relative improvement of ~23%) were found to lie in the closest bin to the center (0-20 pixels, 0.075°) when the correction is applied.

Example 3: Integrated Motion Compensation System and Imaging Feedback

The primary function of the motion compensation system in the mobile solar tracker setup is to accurately determine the real-time orientation of the platform in order to locate the sun in the sky while moving. The secondary purpose is to make a small correction in the imaging data in order to account for the lag time it takes to record the camera image of the solar disk, process it, and update the new motor target position. The given angle accuracy by the manufacturer for the pitch, roll, and heading from the MMQ-G is 0.29°. In practice, the pitch angle measured by the MMQ-G and an independent angle sensor on the NSF/NCAR GV research aircraft agree within 0.15° ($1\sigma$). However, the angular diameter of the solar disk is 0.53° in the sky, and the motion compensation system by itself is not good enough to track the sun accurately while moving. The imaging setup is needed for very high tracking precision. However, with the uneven motion on the road, the imaging setup alone cannot track the sun continuously during drives at any reasonable angular precision and duty cycle. By integrating the imaging setup with the motion compensation system a high level of angular precision and duty cycle is achieved. The advantages of the integrated motion compensation system and imaging feedback loop are the following:

1. The position of the sun in the sky in a wide range of situations, including obstructed and de-aligned viewing conditions, can be accurately determined. The location of the sun relative to the vehicle local orientation is known at any point in time, also when the solar disk is not in the FOV of the camera, e.g., because of bumps in the road, or trees, buildings, bridges and/or clouds obstructing the view.

2. Time needed to search for the sun in the sky is eliminated and results in an improved duty cycle of the instrument to conduct measurements and minimize data gaps.

3. Straightforward operation of the instrument is possible. Only a rough alignment is needed to orient the tracker mirrors and the motion compensation system. The final tracking accuracy is based only on the imaging loop.

4. High-precision tracking of the sun is achievable.

Example 4: Direct Sun DOAS

The solar tracker was coupled to an Ocean Optics QE65000 spectrometer with thermo-electrically cooled charge coupled device (CCD) array detector via optical fiber bundles for DSDOAS measurements. A 12 m long 1.5 mm diameter fiber bundle transfers the direct solar beam from the solar tracker to a 10 m long 1.7 mm diameter single core silica fiber to minimize polarization effects. The other end of the monofiber is connected to a fiber bundle that delivers light to a single UV-Vis spectrometer, or to a bifurcated fiber bundle connected to two or more UV-Vis spectrometers. The mono-fiber was found to be critical during the DOAS analysis of the UV-Vis spectra. Without the mixing monofiber the root mean square of the DOAS fit increased gradually over a short period of time, which was not observed when the mixing fiber was in place. A single spectrometer that covered the wavelength range of 390 to 520 nm with ~0.55 nm resolution (full width at half maximum) was used during FRAPPE 2014 to measure $NO_2$ VCDs. The optical spectrometer bench was heated and kept at a constant temperature of 40±0.05° C., to minimize changes in optical properties, while the detector itself was cooled to −10° C. to reduce dark current. The temperature stability was maintained by using a two-stage temperature-controlled housing. The integration time for each spectrum was 2 s. An absorptive neutral density filter with an optical density of 1.6 (e-based) was placed above the focusing lens of the solar tracker to avoid saturation of the detector.

Example 5: DOAS Analysis

Figure 5:
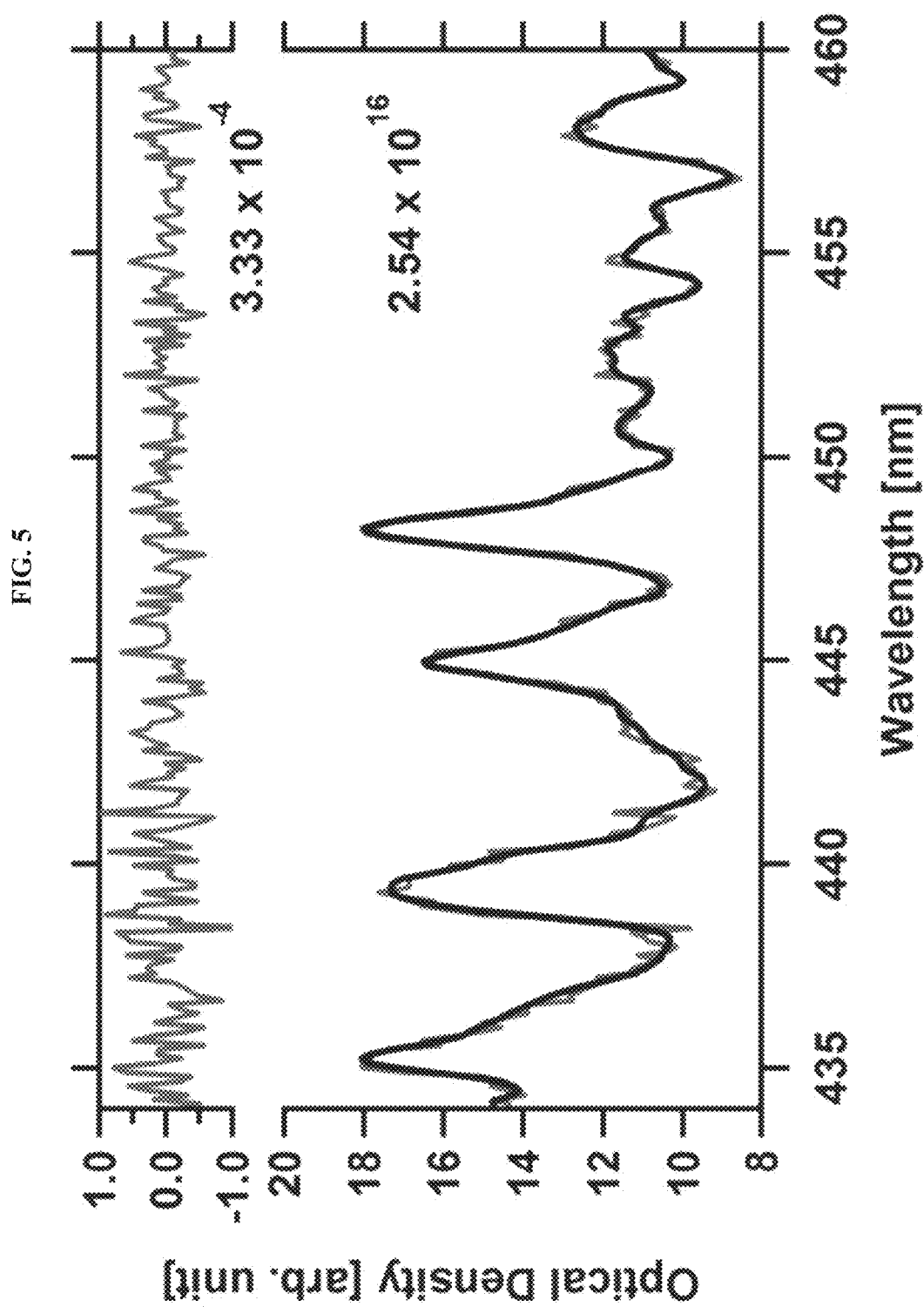
FIG. 5 is a graph of the spectral fits of $NO_2$ and corresponding residual (top panel) from the DOAS fit. The spectrum was taken at 16:59:00 UTC (SZA=37.4°) during the RD#11 on Aug. 13, 2014. The red line represents the measured spectrum and the black line is the fitted cross section. The retrieved $NO_2$ dSCD and RMS for the DOAS fit are also shown.

The wavelength range of 434-460 nm was used for DOAS retrieval of $NO_2$. Trace gas reference cross sections for $NO_2$ at 298K, orthogonal $NO_2$ at 220 K, $O_3$, $H_2O$, $O_4$, glyoxal, and a center to limb darkening (CLD) reference spectrum were simultaneously fitted using a nonlinear least square fitting routine. The CLD correction reference spectrum was calculated as described in the following section and fitted to account for uneven decreases in intensity of solar spectrum at the center and at the limb of the solar disk. CLD is also used to evaluate tracker performance. A fifth-order polynomial to account for scattering processes and broadband absorption in the atmosphere as well as broadband instrumental features, and an additional intensity offset to account for instrument stray light were also included in the fitting procedure. A spectrum from a clean background region was included as the Fraunhofer reference spectrum in the analysis. FIG. 5 shows a spectral fit for $NO_2$ and the corresponding residual from the DOAS fit.

Example 6: Center to Limb Darkening

The effective emission temperature for solar radiation coming from the center is higher compared to the edges of the solar disk. This decrease in effective emission temperature results in an observed decrease in solar intensity towards the edges of the solar disk. This effect is known as the center-to-limb darkening. The optical depth (OD) of the solar Fraunhofer lines also decreases from the center to the edges of the solar disk and results in the need for the CLD correction in DOAS analysis for UV-Vis solar occultation measurements. An empirical approach to correct for the CLD effect showed that the addition of a CLD correction improved DOAS retrieval of iodine monoxide (IO) and chlorine dioxide (OClO) from balloon-borne solar occultation measurements. High-resolution solar spectra taken from the solar disk center and averaged over the solar disk were used to create a reference pseudo-absorber cross section that was included in the DOAS fits.

Figure 6A:
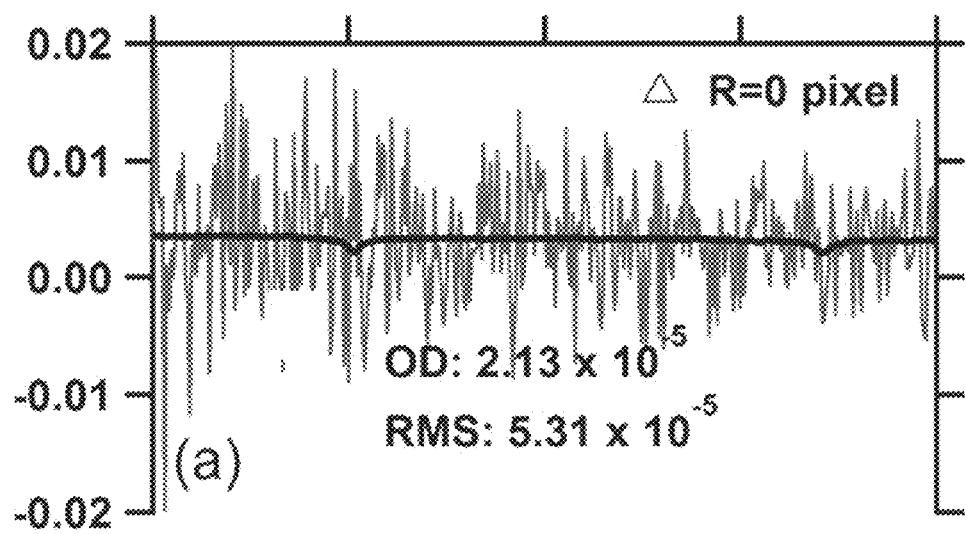
FIGS. 6A-6C are graphs of spectral fits of CLD reference for spectra taken at 0, 25 (0.095°) and 50 pixels (0.19°) off of the center of the solar disk. The optical density of the CLD fit result and the root-mean-square residual that remains after subtracting all absorbers are also shown.
Figure 6B:
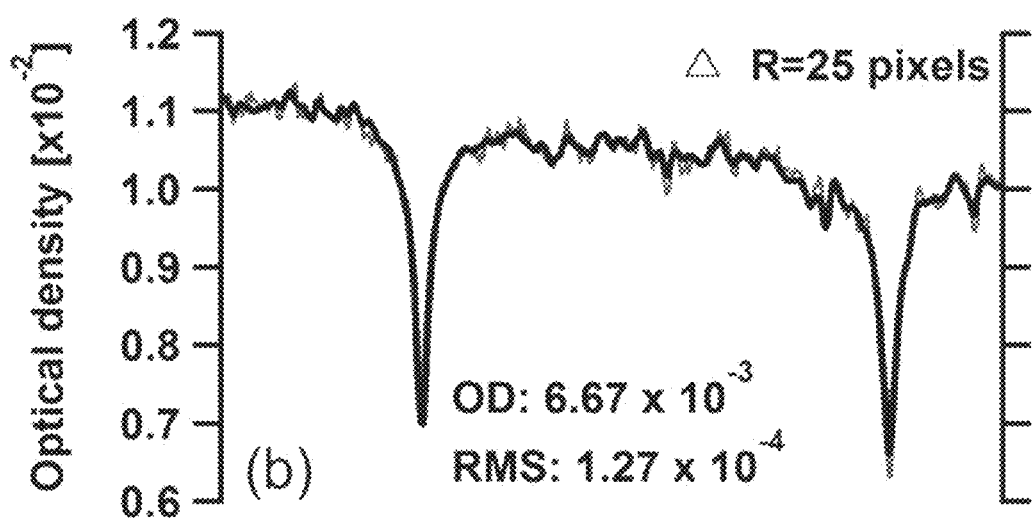
Figure 6C:
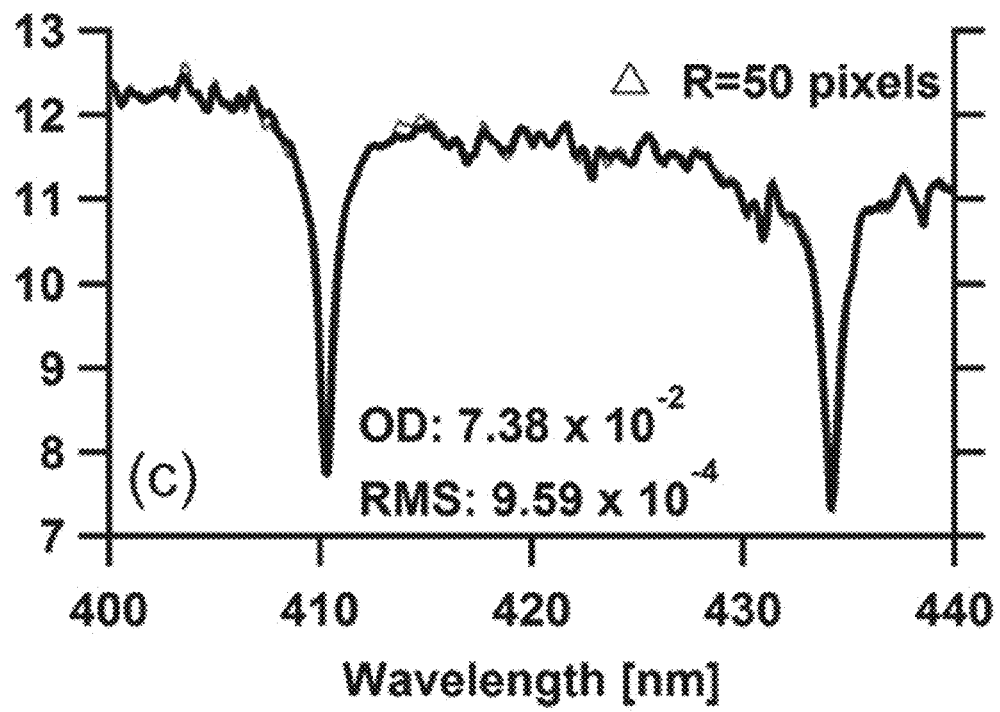

The UV-Vis spectra was determined in the wavelength window from 400 to 440 nm for the CLD correction fit coefficient to estimate the effective tracking precision from spectral data. This fit window was chosen to include two strong Fraunhofer lines (Hδ at 410.2 nm and Hγ at 434.0 nm) in the DOAS analysis. For radiation from the central portion of the solar disk near-zero CLD was expected. A significant CLD signal was expected when the pointing accuracy is suboptimal, i.e., when radiation from near the edges of the solar disk contributes significantly to the overall photon flux of the UV-Vis spectra. FIGS. 6A-6C show the spectral proofs of CLD correction fits for spectrum taken at the center of the solar disk, 25 pixels (0.095°) off of the center, and 50 pixels (0.19°) off of the center. FIGS. 6A-6C clearly illustrate that the CLD correction becomes more important as spectra are collected further away from the center of the solar disk. The inclusion of CLD reference spectrum in the retrieval (1) improved $NO_2$ fit, (2) minimized residuals, and (3) reduced scattering in the retrieved $NO_2$ slant columns.

Example 7: Evaluation of the Tracker Accuracy from Imaging Feedback

Figure 7:
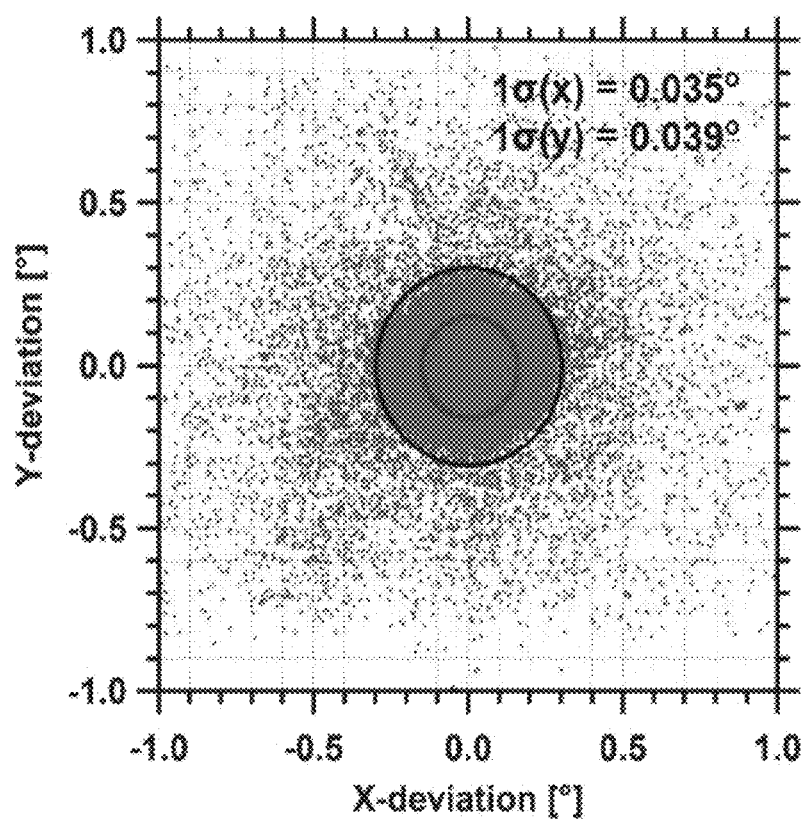
FIG. 7 is a plot of the position of the centers of the solar disk on the aperture plate during the RD#11 on 13 Aug. 2014.
Figure 8A:
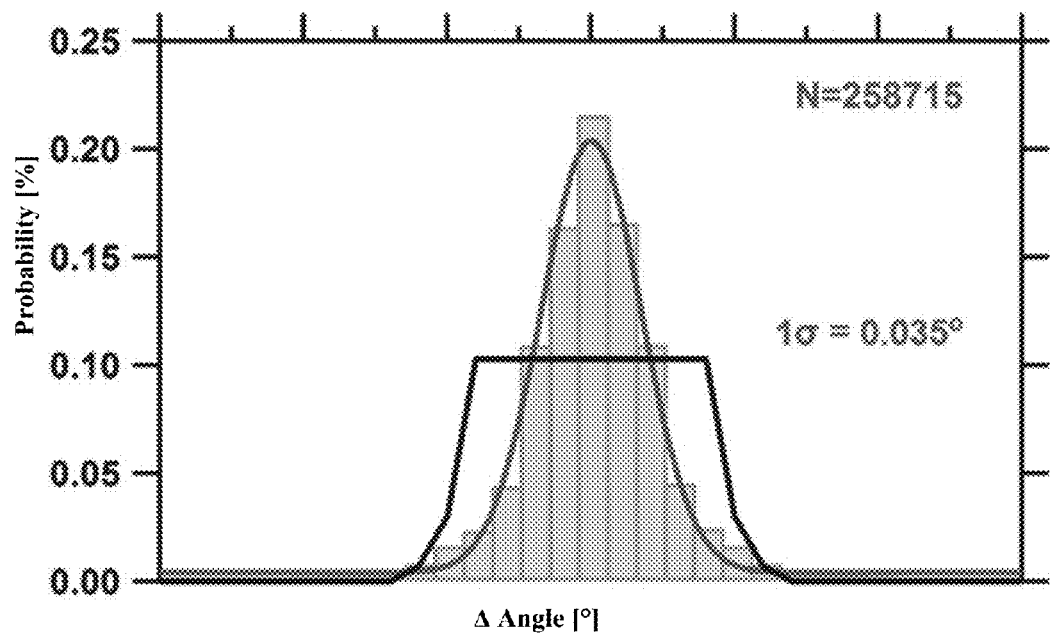
FIGS. 8A-8B depict two histograms of the angular deviation between the solar disk center and the aperture center in x direction (FIG. 8A) and y direction (FIG. 8B). The red lines show the Gaussian fits to the data. The black lines represent the tracking precision derived from CLD fits. The flat top of the distribution reflects the fact CLD signals are significant only at the edges of the solar disk.
Figure 8B:
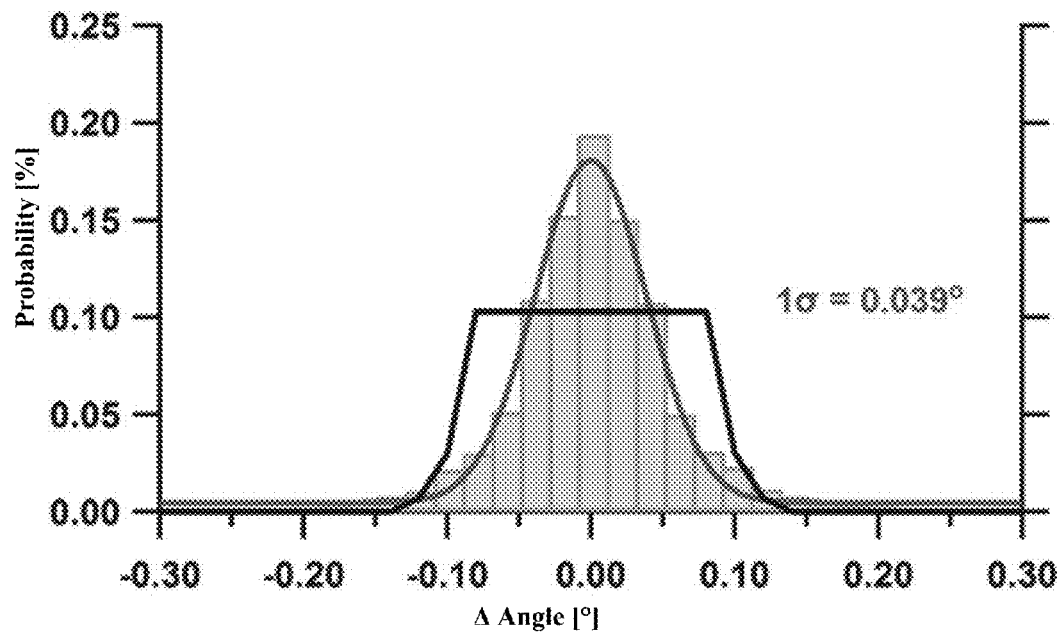

The pointing accuracy of the solar tracker was determined from the deviation of the center of the two fitted circles (i.e., aperture and solar disk) shown in FIG. 2E. The deviations in the x- and y-directions in camera FOV were converted to angular deviation using the relationship between the diameter of the sun in the camera picture and its angular diameter in the sky. The locations of the center of the solar disk for every circle/ellipse fit from the RD 11 (duration ~8 h) on 13 Aug. 2014 are shown in FIG. 7. FIGS. 8A-8B show two histograms of the angular deviation between the centers of the two circles in x and y direction during the RD 11 (only data taken when the vehicle was in motion are included). The 1σ standard deviation in x and y direction determined from a Gaussian fit (red lines) are 0.035° and 0.039° respectively giving an overall pointing precision of 0.052°. Hence the pointing precision (1σ) of about one-tenth of the solar disk angular diameter in the sky was achieved during mobile operation. Note that data points when the solar disk was not in the FOV of the camera are excluded from this analysis. On average the solar disk ventured outside the FOV of the camera every 3-4 s but was highly variable. The solar disk was in the FOV of the camera 88% of the time that the mobile laboratory was in motion. Of the ~12% of the time that the system needed to reacquire the solar disk, the sun was back in the FOV within 0.5 s for 90% of the instances that it was lost. The system is largely unaffected by these short losses because of the fast scan acquisition time (8 ms), which enables filtering of good data with 8 ms time resolution. A 2 s spectrum accumulates many 8 ms scans, and scans that do not meet a minimum threshold signal criteria are automatically eliminated. Thus the 2 s spectra contain useful data that can be evaluated for $NO_2$ VCDs with a duty cycle of ~91% of the drive time under clear-sky conditions.

Figure 9A:
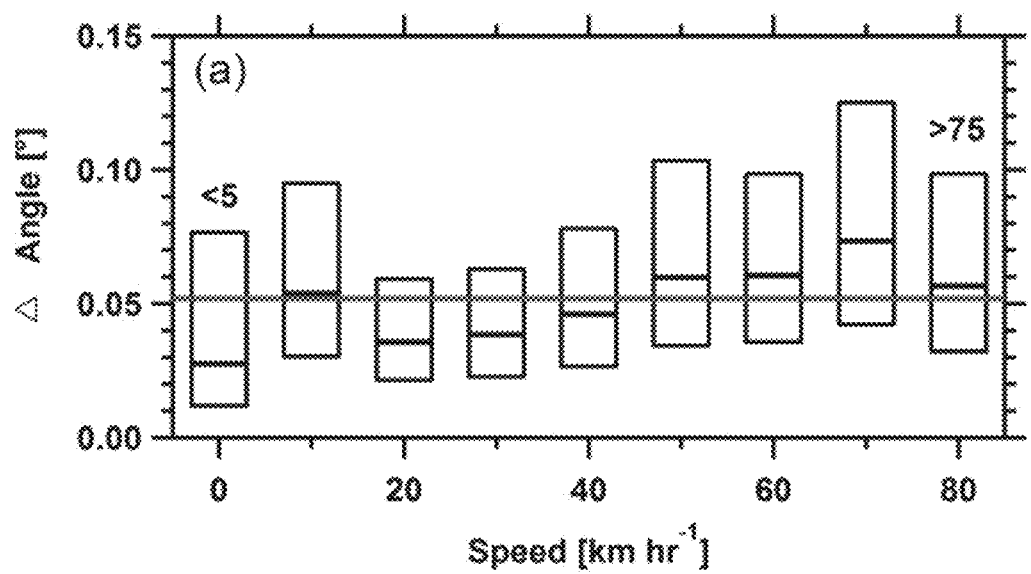
FIGS. 9A-9B are graphs reporting the pointing precision as a function of vehicle speed (FIG. 9A) and solar zenith angle (FIG. 9B) during the RD#11 on 13 Aug. 2014. The top, center and bottom of the boxes represent the 75th, 50th (median) and 25th percentiles of the data. The red lines represent the overall 1σ pointing precision from the Gaussian fits reported in FIGS. 8A-8B
Figure 9B:
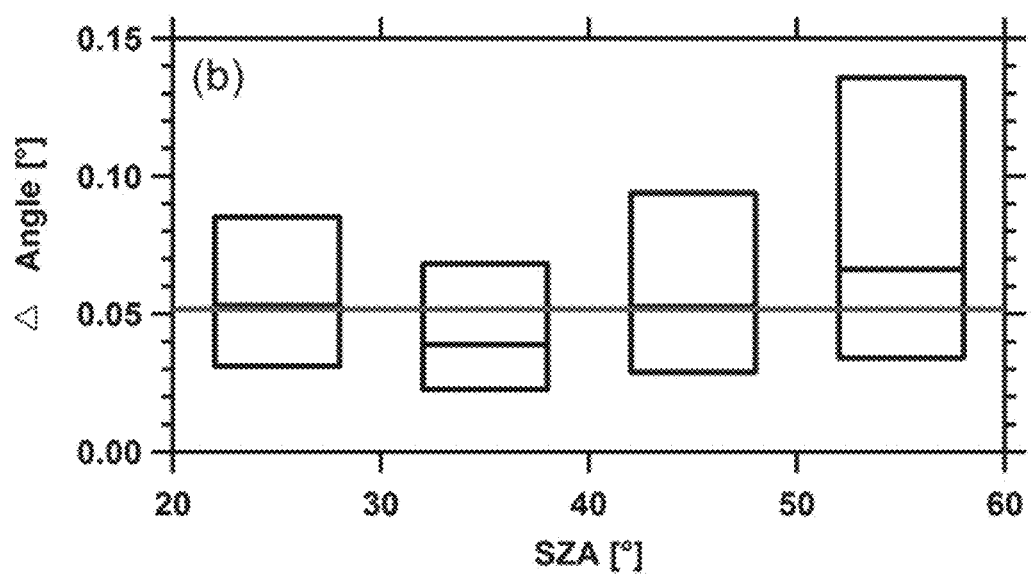

FIGS. 9A-9B show the box plot of angular deviation as a function of vehicular speed and solar zenith angle (SZA) respectively. The top and bottom of the box represent the 25th and 75th percentile of the data respectively while the middle line is the median. The red lines indicate the 1σ tracking precision from the Gaussian fits (FIGS. 8A-8B). The distribution appears to be slightly larger at larger speeds, and above 50° SZA; however, the means were not found to be statistically different. The apparent slight losses in precision seen at 5-15 km h$^{-1}$ and 20-30° SZA were also not statistically different from the mean. Also, this behavior is not observed during other drives.

Example 8: Evaluation of the Tracker Accuracy from the CLD

Figure 10:
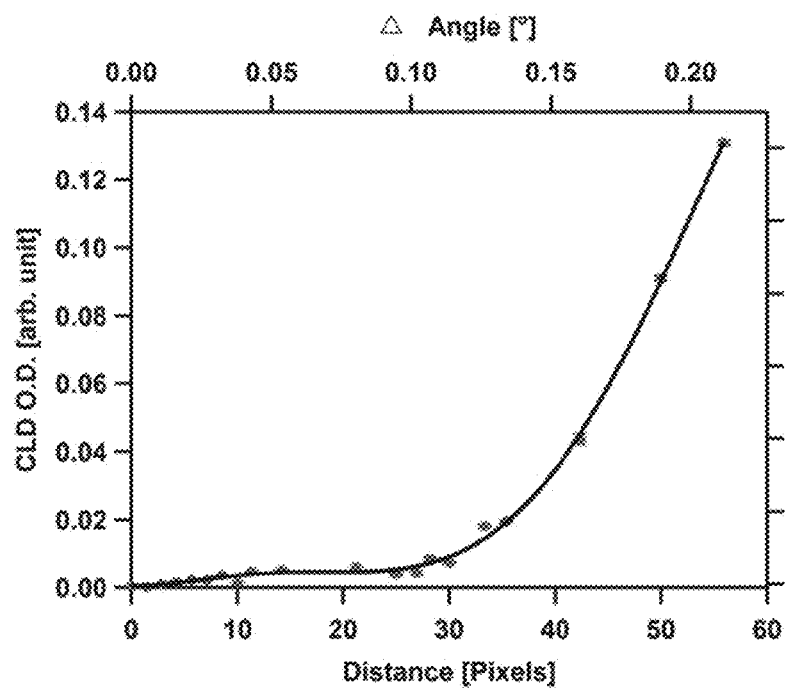
FIG. 10 is a graph of the relation between CLD optical density from DOAS fit and pointing deviation from the center of the solar disk.
Figure 11:
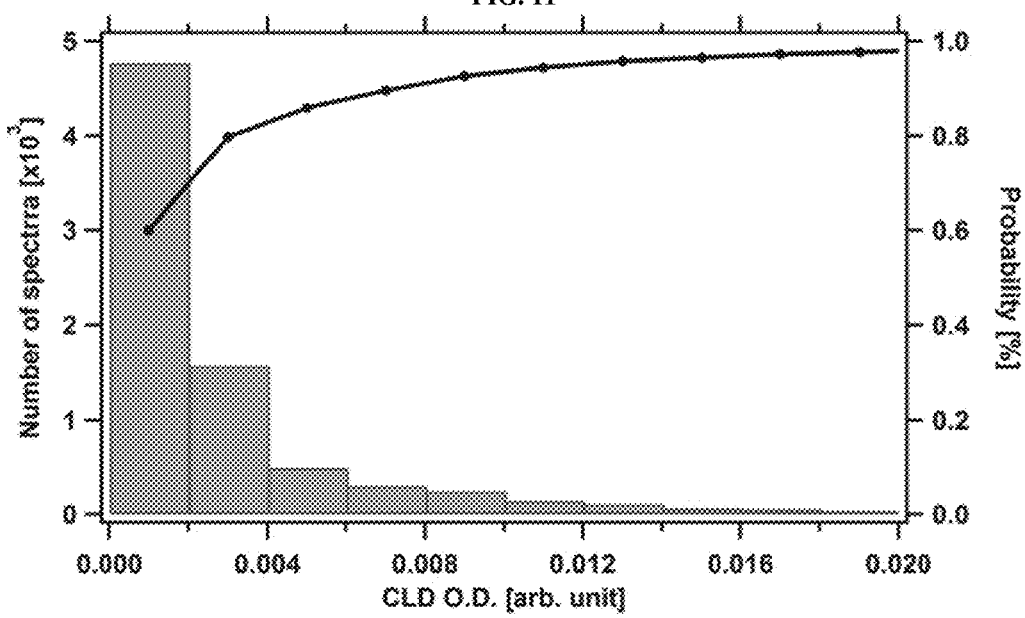
FIG. 11 is a histogram showing the distribution of CLD optical density from the DOAS fit for the spectra collected during the RD#11 on 13 Aug. 2014. The black line shows the cumulative densities.
Figure 12:
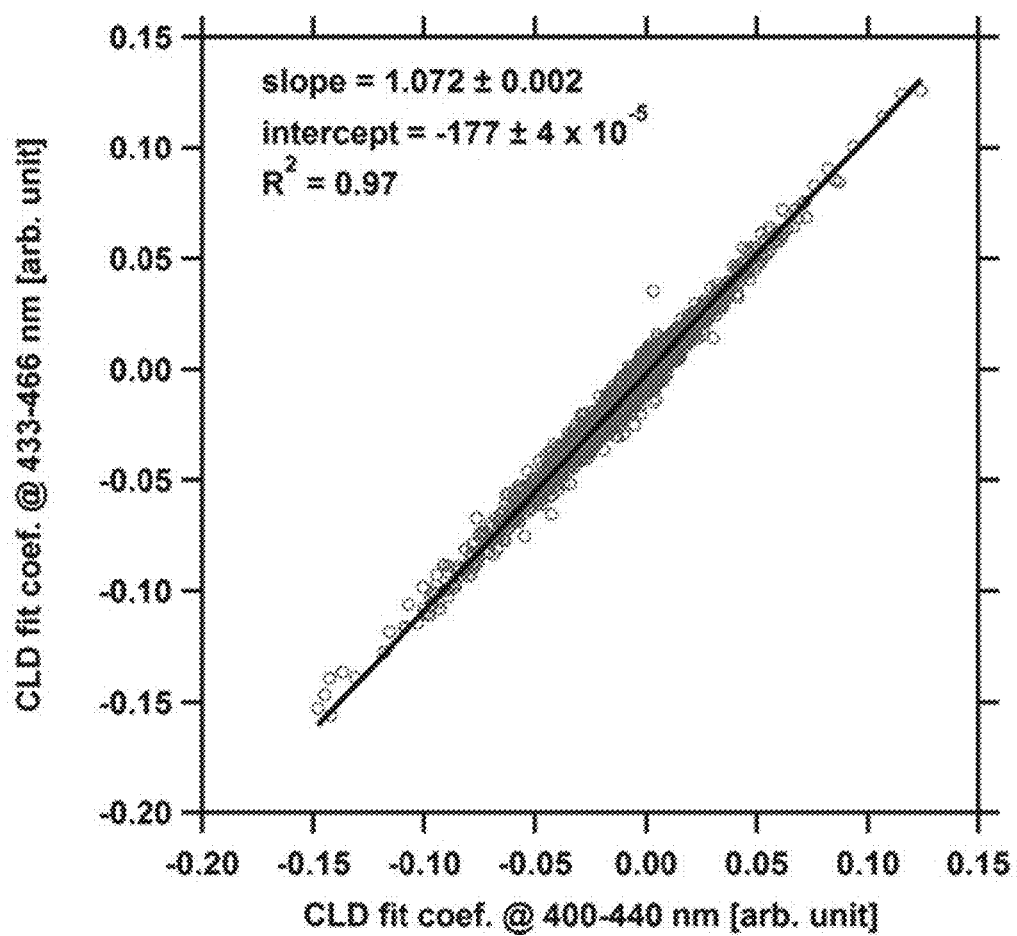
FIG. 12 is a graph of the correlation of CLD fit coefficients retrieved at 400-440 nm and 433-466 nm DOAS fit windows.

FIG. 10 shows CLD fit coefficient (absolute value) as a function of distance from the center. The chosen Fraunhofer reference spectrum from the center of the solar disk for the DOAS analysis does not always have the highest OD for the Fraunhofer lines since it also depends upon the SZA. Thus, depending upon the SZA of the reference spectrum and the measured spectrum, the CLD fit coefficient can change sign and require the use of absolute value. The fit coefficient gradually increases with the increasing distance from the center of the disk until it is 25-30 pixels off of the center. After that the increase in the fit coefficient is much more pronounced. In fact, from 0 to 30 pixels the CLD fit coefficient is not very sensitive to the pixel offset. This is because CLD is a power law function of distance from the center of the solar disk to the limb and hence is not very sensitive close to the center. Without being limited by any particular theory, this insensitivity closer to the center is likely further pronounced in the setup for the following reasons: (1) the size of the aperture used to collect the radiation for the UV-Vis spectra (~40 pixels in radius) results in radiance-weighted average spectra that show no significant need for CLD correction until it is 25-30 pixels off of the center; (2) As the SZA of the sun changes the observed CLD is a combination of the solar movement and pointing inaccuracy and can have compensating effects over small scales. It is clearly evident from FIG. 10 that the CLD ODs from DOAS fits are a robust method of quantitatively determining whether an individual spectrum was taken within 30 pixels of the center or outside this threshold. The CLD ODs from the DOAS analysis for the RD 11 are shown in FIG. 11 as a histogram and a cumulative probability distribution function for different fit coefficient bins. FIG. 11 shows that 95% of the data are within the CLD OD of 0.13, which corresponds to pixel offset of ~30 pixels or an angular precision of about 0.12° (2a). This is consistent with angular tracking precision of 0.052° (1σ) determined from the camera data. The black lines in FIGS. 8A-8B represent the tracking precision derived from CLD fits. The flat top of the distribution reflects the fact that CLD is insensitive across the solar disk and only at the edges the CLD signals are significant (FIG. 10). The precision of the CLD correction fits from DOAS analysis has been crosschecked using the CLD correction fit from the $NO_2$ retrieval window and showed excellent agreement (slope=1.07, intercept=1.77× $10^{-3}$, $R^2$=0.97; see FIG. 12). The 7% increase in slope is very likely due to the wavelength dependence of CLD. A 9±3% increase in CLD fit coefficient is expected based on the wavelength dependence from 420 to 450 nm.

Figure 13:
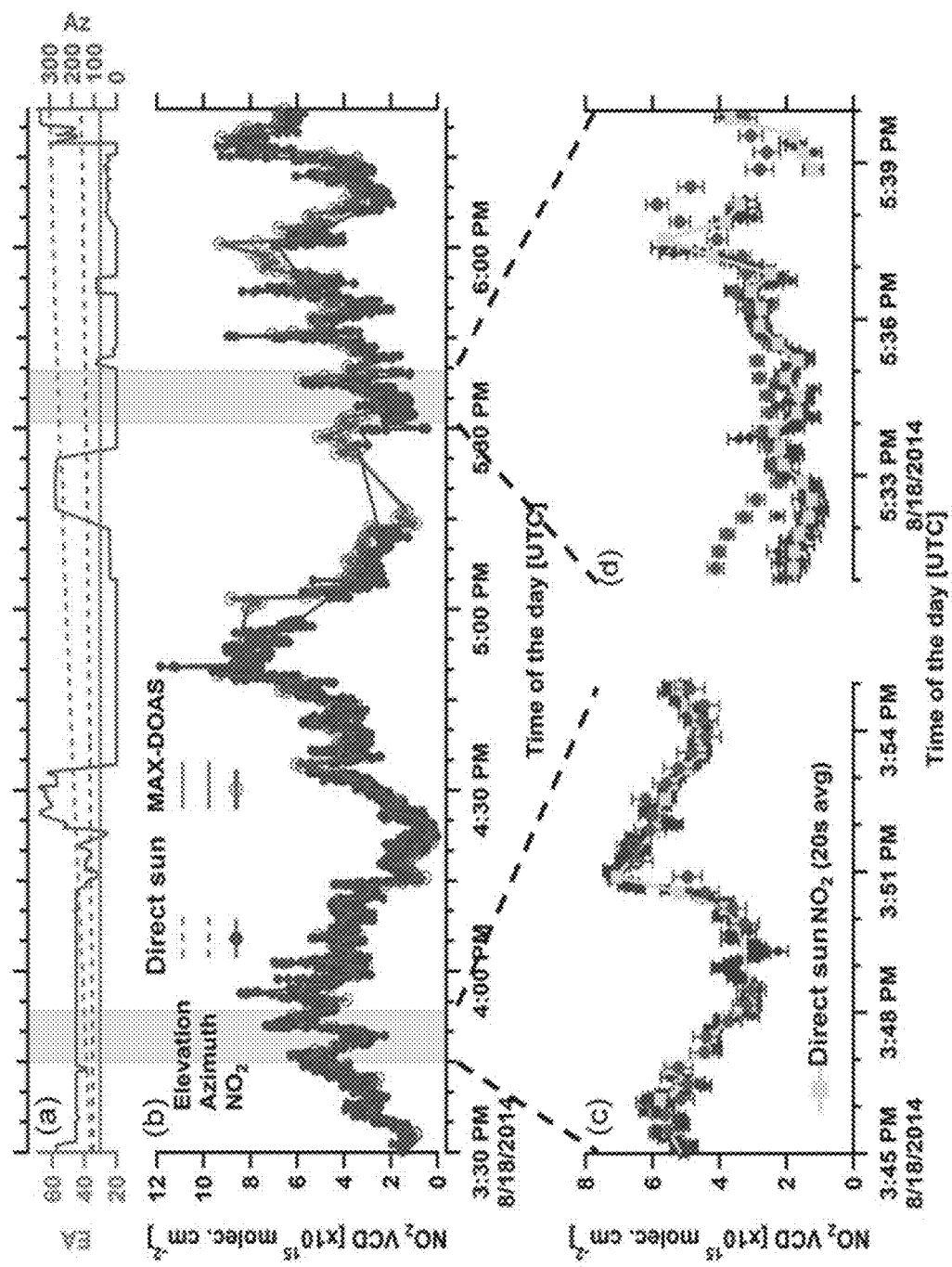
FIG. 13, comprising panels (a)-(d), reports measurements of $NO_2$ VCD aboard the mobile laboratory during the RD#14 on 18 Aug. 2014 in northern Colorado. Panel (a) reports the EA and the Az angles for the DS-DOAS (dashed) and the MAX-DOAS (solid). Panel (b) reports the time series of $NO_2$ VCD measured by the DS-DOAS and the MAX-DOAS. Panels (c) and (d) show expansion into two 9 min period (gray boxes) when (i) difference in EA and Az between the two instruments was ~10° and ~70° and (ii) difference in EA and Az was ~25° and ~140°. The direct sun $NO_2$ line (yellow) represents the DS-DOAS data averaged to the MAX-DOAS timestamp. Note that the MAX-DOAS instrument was acquiring a zenith reference spectrum at 15:49 for 60 s. The open circles in panel (c) (at ~3:51-3:52 PM) represent the MAX-DOAS data points which do not pass the root-mean-square-based quality control but was included for comparison purposes. The error bars in panel (c) and panel (d) represent 1σ fit errors.
Figure 14:
FIG. 14 is a map of $NO_2$ vertical column measurements along the drive track during RD#14 on 18 Aug. 2014 in Northern Colorado.

Example 9: Field Applications and Comparison with MAX-DOAS $NO_2$ VCDs measured by DS-DOAS using the mobile solar tracker were compared with VCDs from a co-located MAX-DOAS instrument on the mobile laboratory. $NO_2$ dSCD from both instruments were converted into VCDs using a geometric air mass factor (geoAMF=1/sin(EA)). FIG. 13 shows the time series of $NO_2$ VCDs measured by the two instruments during RD 14 on 18 Aug. 2014 in northern Colorado. The drive track for the research drive is shown in FIG. 14. The $NO_2$ detection limit and precision (1σ) for the direct sun measurements are $7 \times 10^{14}$ and $3 \times 10^{14}$ molecules $cm^{-2}$ respectively for a 2 s integration time. Even though the two instruments are co-located and used a similar retrieval, the comparison is not straightforward because of the following: (1) the viewing geometries of the two instruments are not the same. MAX-DOAS measurements were made at 30° EA facing towards the back of the mobile laboratory. DS-DOAS observations depend upon the solar elevation and azimuth angle (Az) at the time of the measurements. Thus, the two instruments are typically not looking at the same air mass; (2) Both instruments make measurements averaged horizontally over a distance that depends upon the EA. For example, for a boundary layer height of 1 km, the MAX-DOAS observations at 30° EA average over a horizontal distance of 1.7 km (geometric path). In contrast, the direct sun observation only averages over a horizontal distance of 0.6 km at solar elevation of 60°.

The EA and Az angles at the time of measurements for the two instruments are shown in FIG. 13, panel (a). The agreement between $NO_2$ VCDs is found to be best when the two instruments have similar viewing geometry. An expanded view of $NO_2$ VCD over two 9 min periods when (i) EA and Az angles for the two instrument are relatively similar (i.e., looking at the same air mass; δEA=~10° and δAz=~70°) and (ii) difference in EA and Az angles are larger (i.e., looking at the different air masses; δEA=~25° and δAz=~140°) are shown in FIG. 13, panels (c) and (d) respectively. The agreement between the two instruments is indeed better in FIG. 13, panel (c) compared to FIG. 13, panel (d). During the period shown in FIG. 13 panel (d), the two instruments were almost looking in opposite directions along the drive track. As the MAX-DOAS was looking towards the back of the mobile laboratory, it observes the air mass probed by the solar tracker after a certain time which is dependent upon the speed of the vehicle. FIG. 13, panel (d) shows a small offset in the magnitude of $NO_2$ VCD as well as time (see peak at 17:37). The small offset in magnitude is likely due the difference in EA where the MAX-DOAS averages over a larger distance while the offset in time is a result of Az viewing geometry.

Figure 15:
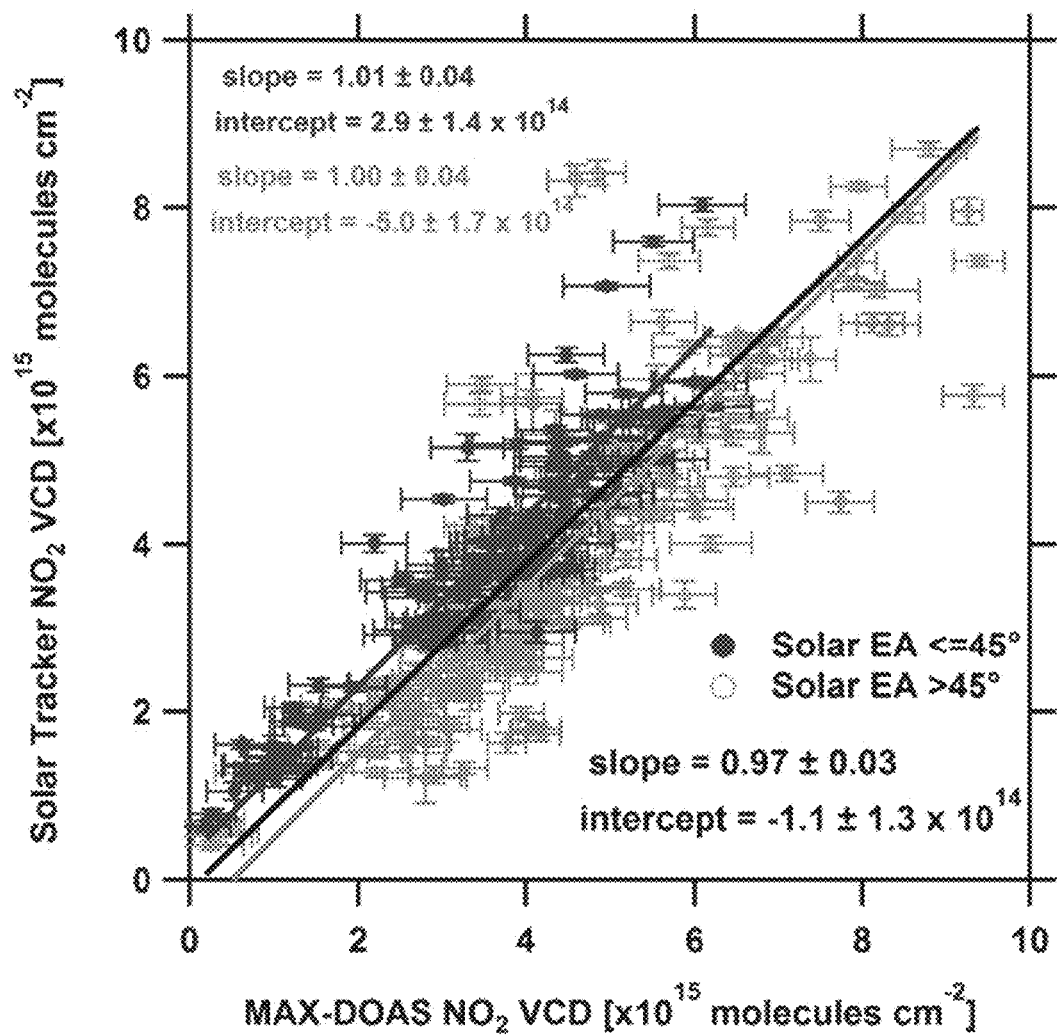
FIG. 15 is a correlation graph of $NO_2$ vertical column measured by the DS-DOAS (solar tracker) and MAX-DOAS instruments during RD#14 on 18 Aug. 2014 in Northern Colorado. The lines show orthogonal distance least square fit to all data (middle line), for solar EA<=45° (dark) and for solar EA>45° (light). The error bars represent 1σ fit error for respective instruments. The DS-DOAS data were averaged for 20 seconds in time to the MAX-DOAS timestamp.

The time series for $NO_2$ measured by the two instruments track each other very well. High photon flux in the direct solar beam enabled fast measurements with high signal to noise, and this is evident in the time series. The DS-DOAS measurements captured variability in $NO_2$ at much finer scale than the MAX-DOAS data. This has potentially important benefits with resolving column enhancements of spatially confined emission sources, and the spatial variations within plumes. The good agreement between the DS-DOAS and MAX-DOAS observations is reflected in the slope of 0.97±0.03 for the orthogonal distance regression of the two data sets (FIG. 15, offset=−1.1±1.3×$10^{14}$ molecules $cm^{-2}$). All data shown in FIG. 13, panel (b) are included in the comparison regardless of the EA and azimuth angle difference. The DS-DOAS data are averaged for 20 s to the MAX-DOAS timestamp. If the data are filtered for the solar EA (i) below 45 and (ii) above 45, the slopes of the orthogonal least squares fits improve to unity (1.01±0.04 for case (i) and 1.00±0.04 for case (ii)) but not significantly different from the fit to all data. The offset is larger (−5.0±1.7×$10^{14}$ molecules $cm^{-2}$) for the second case. Such good agreement gives confidence in the validity of the new solar tracker measurements for $NO_2$ and other species using the DS-DOAS method. In certain embodiments, the data obtained using the compositions and methods of the invention can be used to quantify emissions of trace gases from various sources such as power plants, refineries, farms, and feedlots.

Example 10: Mobile Solar Occultation Flux with EM27 FTS

A customized BRUKER® EM27 FTS was coupled to the solar tracker described in Example 1 and used as part of a mobile platform for the measurement of trace gases at Mid-IR wavelengths. The EM27 FTS is a Michelson interferometer with a double pendulum corner cube mirror design. The oscillating mirrors determine the optical path difference (OPD). this configuration allows for fast scanning at 160 kHz to provide spectra acquisition with 2 Hz time resolution and includes a zinc selenide (ZnSe) beam splitter and window, 24V power supply and a Stirling-cooled sandwich detector operating at 77 K, consisting of a mercury cadmium telluride (MCT) and an indium antimonide (InSb)

detector in a single detector housing. Each detector has an active area of 1 nm diameter. The FTS allowed for measurements over a wide spectral range in the mid-IR spectral region of the solar spectrum from 700 to 5000 cm$^{-1}$. An apodization function was not used for the measurements during FRAPPE. Boxcar was selected in order to keep the resolution at its maximum of 0.5 cm$^{-1}$. Further specifications about the instrument configuration are provided in Table 1.

TABLE 1

Specification of the mobile SOF instrument

|  | Mid-IR | | UV-Vis |
|---|---|---|---|
| Characteristic | Channel 1 | Channel 2 | Channel 3 |
| Spectrometer | Michelson interferometer EM27 | | Grating spectrometer QE65000 |
| Spectral resolution | 0.5 cm$^{-1}$ | | ~0.55 nm |
| Detector | MCT | InSb | CCD |
| Spectral range | 700-1850 cm$^{-1}$ | 1850-5,000 cm$^{-1}$ | 390-520 nm |
| Dimensions[1] | 860 nm × 520 nm × 600 nm | | |
| Weight[1] | ~45 kg | | |
| Power requirement[2] | 115 V AC, 380 W | | |

[1]Includes the solar tracker, spectrometers and base plate.
[2]includes the solar tracker, spectrometers, laptops for data acquisition and control electronics.

Example 11: Trace Gas Data Retrieval

Figure 16:
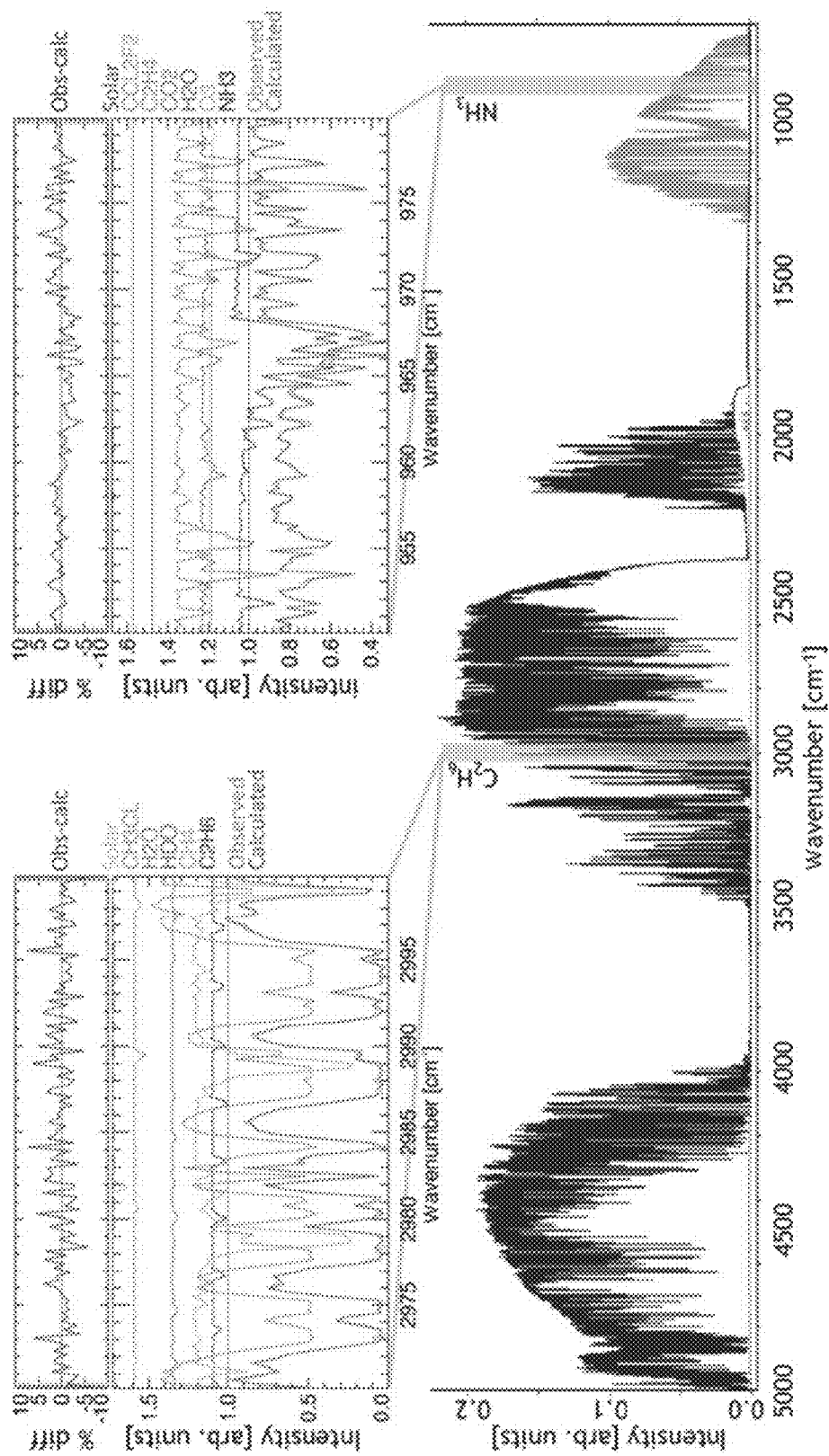
FIG. 16 is a solar spectrum measured by the InSb (blue) and MCT (green) detectors. Highlighted bars indicate the spectral intervals used for the retrieval of $C_2H_6$ and $NH_3$. Spectral proof of $C_2H_6$ is shown on the top left and of $NH_3$ on the top right. The $C_2H_6$ column was $7.13 \times 10^{16}$ molecules $cm^{-2}$ (% rms=2.7) and the $NH_3$ column was $40.2 \times 10^{16}$ molecules $cm^{-2}$ (% rms=1.9) for the retrievals shown.

The spectra taken with the MCT detector were corrected for instrument background. An example solar spectrum measured by the MCT and InSb detectors is shown in FIG. 16, where the micro windows used for the $C_2H_6$ and $NH_3$ retrieval are highlighted. $NH_3$ VCDs were retrieved from MCT spectra using the micro window 950-980 cm$^{-1}$. The InSb spectra were used without further corrections for the retrieval of $C_2H_6$ at 2970-3000 cm$^{-1}$. The spectral fit windows including interfering species are listed in Table 2. All retrievals were conducted using SFIT4 software (Hase et al., Appl. Opt., 38, 3417-3422, 2004) and a priori profile parameters as given in Table 3. SFIT4 uses the vertical profiles of pressure, temperature and water vapor taken from NCEP (National Centers for Environmental Prediction) and WACCM (Whole Atmosphere Community Climate Model) at given altitudes that were assumed to be constant throughout each day. It uses updated $C_2H_6$ lines from Harrison et al. (J. Quant. Spectrosc. Ra., 111, 357-363, 2010) and HITRAN 2008 (Rothman et al., J. Quant. Spectrosc. Ra., 110, 9, 533-572, 2009) line lists for all other absorbers listed in Table 2. The a priori error allows for the VCD of interest ($NH_3$ or $C_2H_6$) to vary by a factor of 100 around the a priori value; the interfering gases, e.g., $CO_2$ and $H_2O$, were allowed less variability. SFIT iterates to obtain a best fit between the calculated and measured spectrum. The residual parameter (% rms) is used to quality assure the data. The quality assurance cutoff % rms value has been determined by contrasting $1/\sqrt{N}$ noise against the residual, where N is the cumulative number of spectra that have a % rms less than or equal to the threshold, and noise is the spread of residuals within the threshold. The cutoff % rms has been taken as 3 times the minimum of the $1/\sqrt{N}$ noise against the residual plot and was determined to be 3.6 for $NH_3$ and 6.4 for $C_2H_6$. This translates to ~75% of $NH_3$ and ~47% of $C_2H_6$ spectra being considered during analysis. Spectral proof of the detection of both gases is shown in FIG. 16. In this demonstrated case, the detected gas column density of $C_2H_6$ has a value of 7.13×10$^{16}$ molecules cm$^{-2}$ and for $NH_3$ a value of 40.2×10$^{16}$ molecules cm$^{-2}$, which is well above the detection limit. The top panel of the fit window shows the residual between observed and fitted spectrum. Besides the observed and fitted spectrum the fit window also includes the strongest interfering trace gases.

TABLE 2

Spectral fit windows used in retrievals

| Target Species | Interfering Species | Spectral Range |
|---|---|---|
| $NH_3$ | $O_3$, $H_2O$, $CO_2$, $C_2H_4$ | 950-980 cm$^{-1}$ |
| C2H6 | $CH_3Cl$, $H_2O$, HDO, $CH_4$ | 2970-3000 cm$^{-1}$ |
| NO2 | $O_3$, $H_2O$, $O_4$, $C_2H_2O_2$, CLD | 434-460 nm |

TABLE 3

Overview of SFIT4 a priori values

| Species | A priori (molecules/cm$^2$) | A priori error (%) |
|---|---|---|
| $C_2H_6$ | 1.18 × 10$^{16}$ | 10,000 |
| $NH_3$ | 2.23 × 10$^{13}$ | 10,000 |
| $CH_3Cl$ | 8.88 × 10$^{15}$ | 1,000 |
| $H_2O$ | 3.78 × 10$^{22}$ | 50 |
| HDO | 1.43 × 10$^{23}$ | 50 |
| $CH_4$ | 3.12 × 10$^{19}$ | 100 |
| $O_3$ | 8.44 × 10$^{18}$ | 1 |
| $C_2H_4$ | 3.75 × 10$^{14}$ | 10 |
| $CO_2$ | 6.65 × 10$^{21}$ | 10 |

Figure 17:
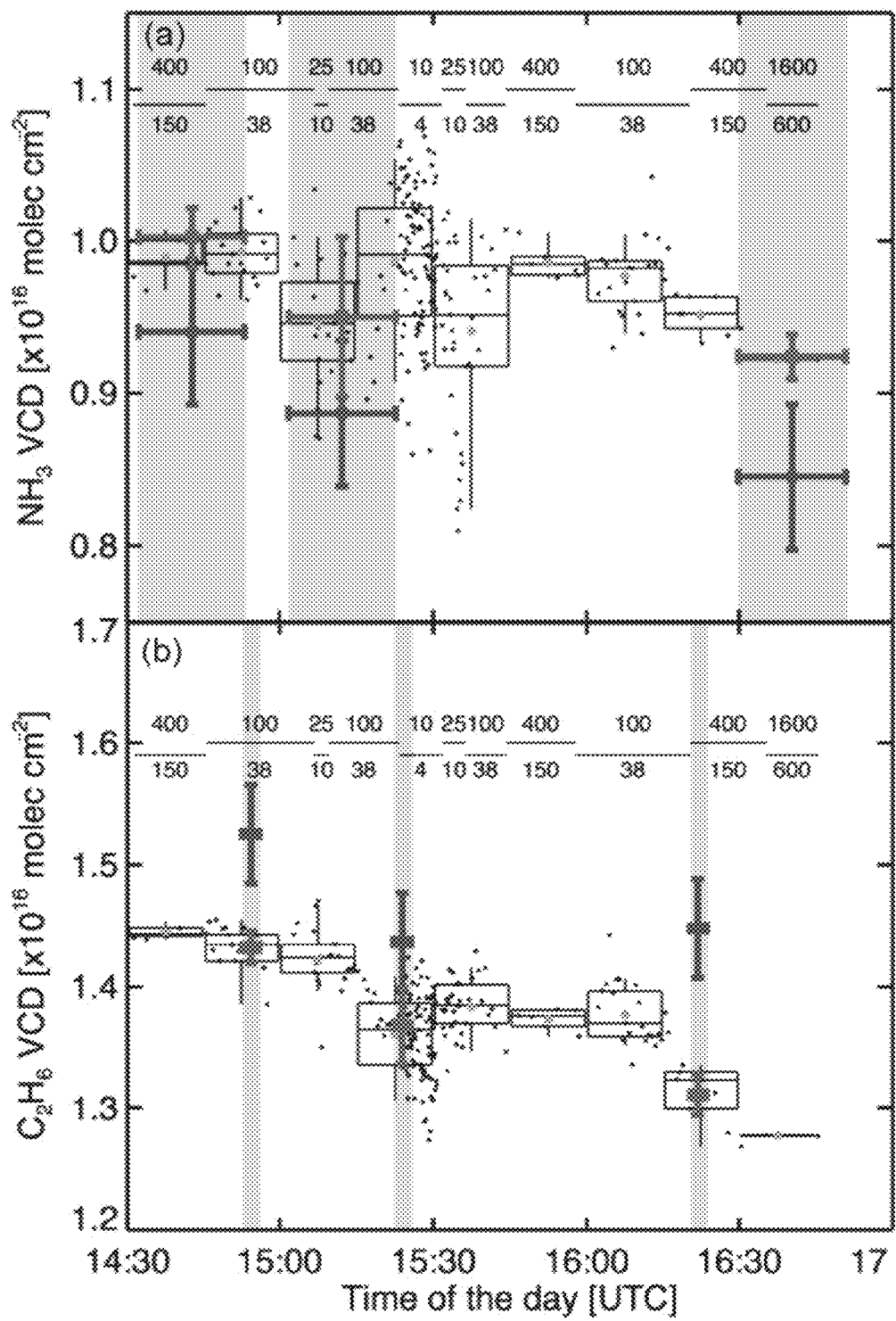
FIG. 17 is a set of graphs showing an assessment of the SOF accuracy versus the HR-NCAR-FTS. The top graph reports $NH_3$ VCD; the lower cross in each segment denotes HR-NCAR-FTS measurements, the upper cross in each segment denotes mobile SOF measurements. The bottom graph reports $C_2H_6$ VCD; the upper cross in each segment denotes HR-NCAR-FTS measurements, the lower cross in each segment denotes mobile SOF measurements. In both graphs, individual reported data points are derived from the mobile SOF device, boxes and center dots are averaged data points over 15 min intervals from the mobile SOF device. Numbers above the dashes indicate the internally co-added scan number and numbers below the dashes indicate the integration time of each stored spectrum in seconds. Boxes and whiskers represent 5th, 25th, median, 75th and 95th percentiles for every 15 min. The VCD uncertainty on the mobile SOF and NCAR measurements is given as the 1σ standard deviation.

Example 12: Comparison of Mobile Device to National Center for Atmospheric Research Values Prior to field deployment, collocated measurements were performed comparing the mobile device described in Example 10 with values derived at the National Center for Atmospheric Research (NCAR) in Boulder, Colo., which is equipped with a high-resolution BRUKER® 120HR FTS (HR-NCAR-FTS). The mobile SOF instrument was mounted in a trailer that was parked in a parking lot ~50 m away from the HR-NCAR-FTS, assuring that both instruments observed the nearly same air mass. Coincident time intervals of the measurements were evaluated to determine the accuracy of the trace gas VCDs and the limit of detection (LOD) of the 0.5 cm$^{-1}$ resolution FTS. LOD was calculated using the equation:

$$LOD_{exp} = k \cdot \sigma_{Gaussian} |background|, \quad (1)$$

where k is a factor chosen according to the confidence interval, and $\sigma_{Gaussian}$ is the standard deviation during a time period in which the air mass is not changing (i.e., constant $C_2H_6$ and $NH_3$ VCD). k=3 was set for a 99.7% confidence interval. The LOD is given in units of VCD and determines the minimum amount of a gas to be detected in order to be statistically distinct from a blank measure. In the mornings before a research drive (RD) and, if the cloud cover permitted, in the afternoon after an RD, stationary measurements were taken in a parking lot at Colorado University (40.005° N, 105.270° W) to determine $\sigma_{Gaussian}$, and they were found to be consistent with the $\sigma_{Gaussian}$ determined at NCAR shown in FIG. 17. A longer integration time averages more scans and reduces the noise in the data. For the background determination mobile SOF data points within the integration time of one HR-NCAR-FTS were averaged. The background was calculated as the difference between mobile SOF FTS and HR-NCAR-FTS data points.

Example 13: Characterization of Instrument Line Shape

Figure 18:
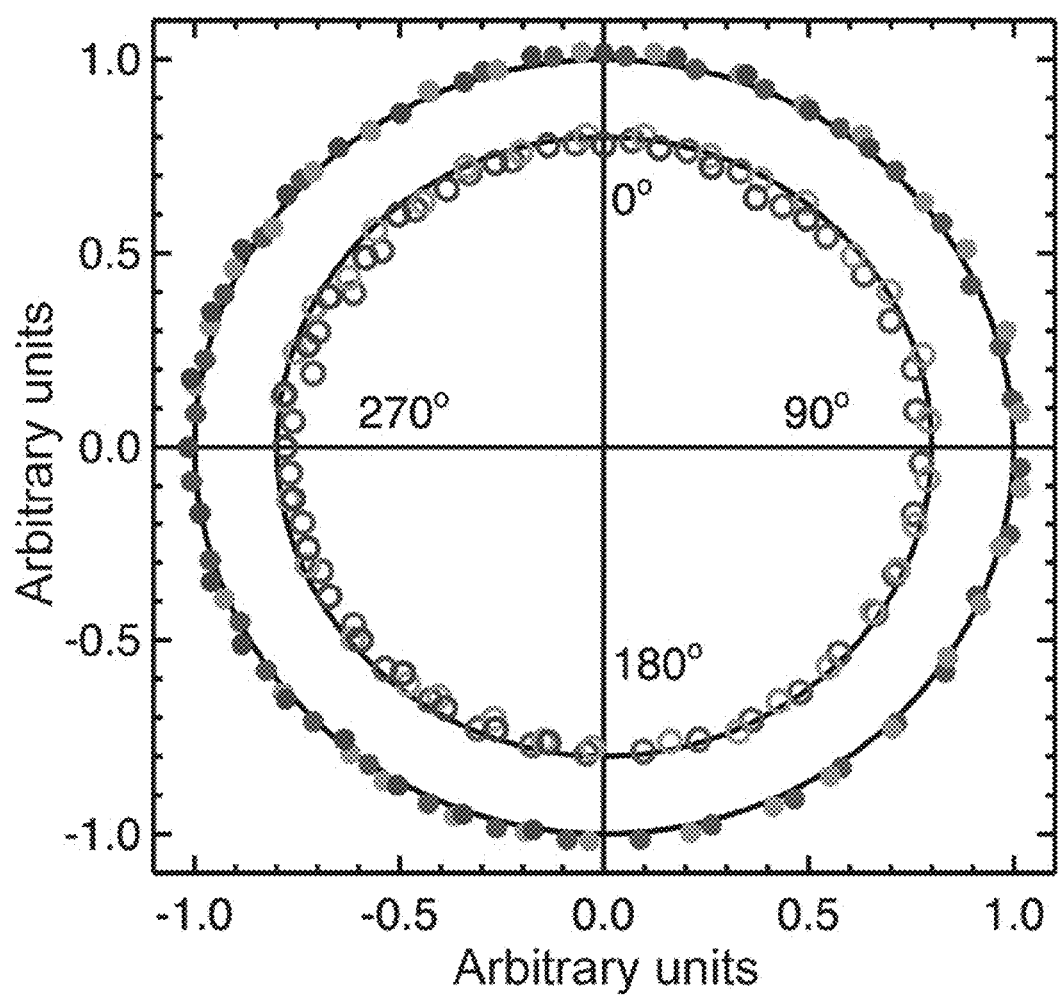
FIG. 18 is a diagram showing angle dependence of the instrument line shape (ILS) modulation efficiency at maximum OPD. MCT detector: open circles. InSb detector: filled circles. Green, red and blue measured at an elevation angle of 5, 45 and 65°, respectively. The black unit circles represent an ideal ILS modulation efficiency having a value of 1.000.

For measurements from the mobile laboratory, the azimuth and elevation angles change rapidly over the course of a research drive. It is therefore important to characterize the instrument line shape (ILS) over a wide range of azimuth and elevation angle pairs. This was tested in a laboratory setup where the solar tracker was pointed at a globar to observe atmospheric water vapor over a distance of several meters along the path between the FTS and the globar. The light emitted by the globar is collimated and directed onto the solar tracker. The FTS with solar tracker is positioned on a rotatable platform. The ILS has been determined using the retrieval code LINEFIT (Hase et al., Appl. Opt., 38, 3417-3422, 1999) version 14 using water vapor absorption lines in the spectral range at 1950-1900 for the InSb and at 1820-1800 cm$^{-1}$ for the MCT detector. The modulation efficiency at maximum OPD is shown in FIG. 18 for different azimuthal and elevation angles.

Figure 19:
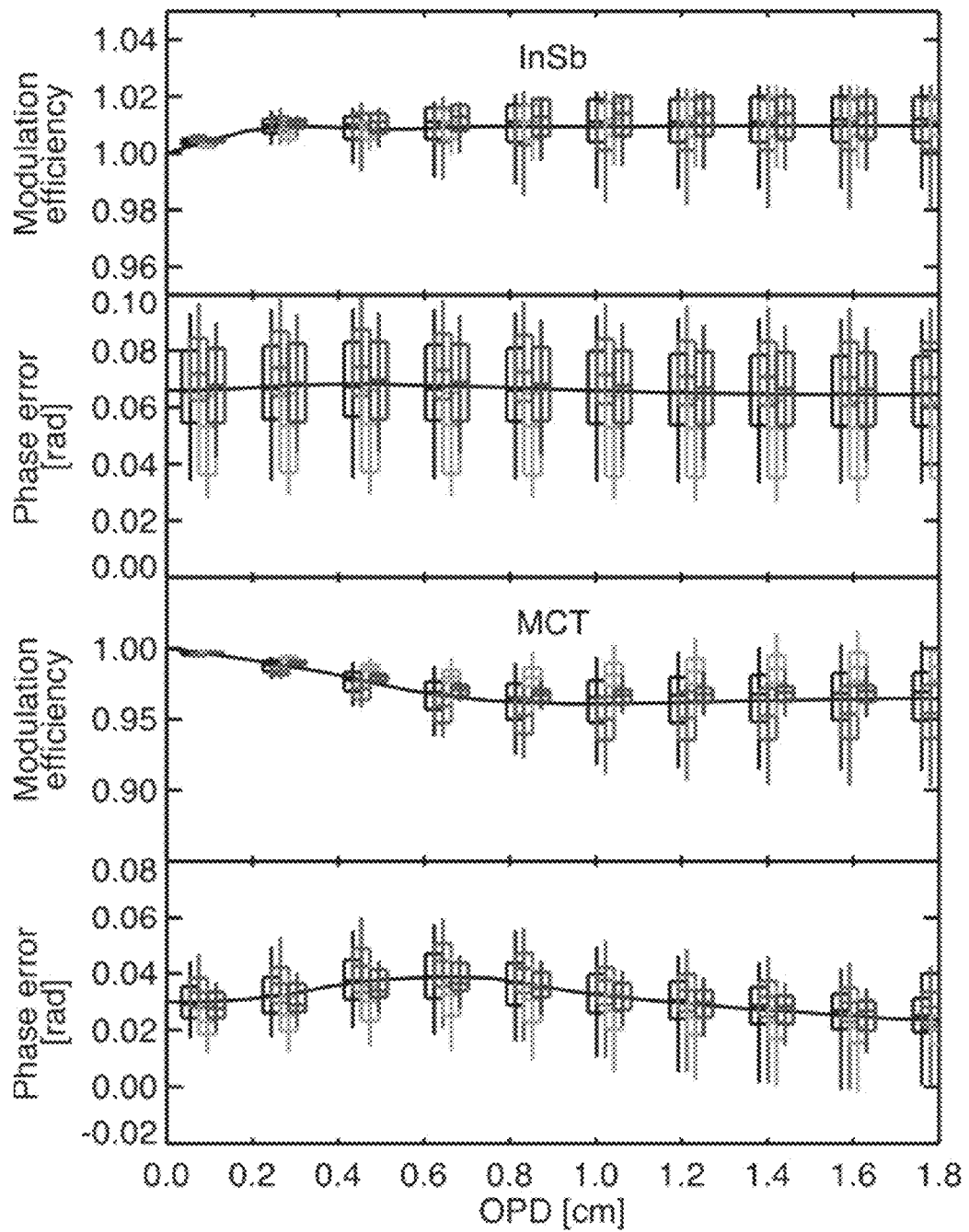
FIG. 19 is a set of graphs showing instrument line shape (ILS) modulation efficiency and phase error as a function of optical path difference (OPD). Top panels: InSb detector. Bottom panels: MCT detector. Boxes mark 25th and 75th percentiles, and the line inside the box marks the median. Lines outside the boxes indicate 5th and 95th percentile. Green, red and blue represent averages over an elevation angle of 5, 45 and 65°, respectively. Black is the average over all data. The different colored whiskers are offset with respect to the OPD for visualization; green whiskers are located at the exact OPD.

While driving around a source area or site of interest there are 90° changes in the azimuth angle with each turn and many smaller degree changes in both elevation and azimuth angles due to fine tracking on uneven dirt roads. Column density measurements along the ~2.0 m long beam between the collimated light source of a globar and the spectrometer at solar tracker azimuth angles from 0 to 360° and at elevation angles of 5, 45 and 65° were recorded to determine the ILS based on water vapor lines. FIG. 18 shows the modulation efficiency at maximum OPD as a function of azimuth angle. The inner circle shows the measurements for the MCT detector; the outer circle shows the measurements for the InSb detector. FIG. 19 shows both the modulation efficiency and phase error as a function of OPD. The top plots show the InSb results; the bottom plots show the MCT results. It can be seen that the modulation efficiency of both detectors shows rather constant behavior. From these experiments it was determined that the MCT detector has a modulation efficiency of 0.968 at maximum OPD and the InSb detector has a modulation efficiency of 1.010 at maximum OPD. These values are obtained by averaging the modulation efficiency at maximum OPD over all azimuth and elevation angle.

To investigate the effect of the ILS on the retrieval of $NH_3$ and $C_2H_6$, the retrieval software was first run using an ideal ILS as input and then using the ILS measured for the MCT and InSb detector, respectively, and comparing the VCD output with ideal and measured ILS. There was 0.5% change in the retrieved $NH_3$ VCD and no change in the $C_2H_6$ VCD. These results are listed in Table 4 and are factored into the total error on VCDs. It was determined that there is no significant angular dependency on the ILS.

TABLE 4

Results of FTS Quality Assurance

|  | Channel 1/$NH_3$ | Channel 2/$C_2H_6$ |
|---|---|---|
| Precision[1] ($10^{16}$ molec/cm$^2$) | 0.01 | 0.01 |
| Accuracy[2] ($10^{16}$ molec/cm$^2$) | 0.07 | 0.10 |
| LOD ($10^{16}$ molec/cm$^2$) | 0.10 | 0.13 |
| Total error (%) | 4.4 | 6.7 |
| OPD effect[3] (%) (2σ) | 1.0 | 0.0 |

TABLE 4-continued

Results of FTS Quality Assurance

|  | Channel 1/$NH_3$ | Channel 2/$C_2H_6$ |
|---|---|---|
| Cross section uncertainty (%) | 2.0[4] | 4.0[5] |
| Fit uncertainty (%) (2σ) | 3.8 | 5.4 |

[1]Calculated as the mean during periods in which the atmosphere remained constant.
[2]Calculated as the difference between the mobile lab FTS of the invention and the NCAR high-resolution FTS.
[3]Calculated for a median VCD of 4.32 × 10$^{16}$ molec cm$^{-2}$ for $NH_3$ and 3.49 × 10$^{16}$ molec cm$^{-2}$ for $C_2H_6$ as measured during RD10 and RD11.
[4]Source: Kleiner et al. J. Quant. Spectrosc. Ra., 82, 293-312 (2003).
[5]Source: Harrison et al. J. Quant. Spectrosc. Ra., 111, 357-363 (2010).

Example 14: Flux Calculations

VCD measurements around a site of interest were used in combination with wind fields to calculate the emission flux using the equation:

$$\text{Net Flux} = \int_S VCD \, \vec{F} \cdot \vec{n} \, ds \tag{2}$$

where VCD is the vertical column density, $\vec{F}$ is the wind vector, $\vec{n}$ is the outward facing normal with respect to the driving direction, and the integral over ds represents the drive track around a closed box. In order to determine the emission flux or production rate of a gas the wind vector needs to be known.

Model wind was used to perform the flux calculations. The model wind, extracted from the North American Mesoscale Model using the National Emission Inventory 2011 version 2 (NAM, NEI 2011v2) and with inner domain of 4 km, was interpolated for hourly instantaneous values at 36 altitudes from ~10-50 m above ground to ~18.5 km along the exact drive track coordinate and time.

The model wind was compared to measurements of wind speed and direction at the Boulder Atmospheric Observatory (BAO), observed at 10, 100 and 300 m above ground; FIG. 20 shows where the BAO tower is located. The uncertainty analysis of the model wind speed and wind direction is based on the time window 16:00-22:00 UTC, which is the time spent on the RDs. The model wind did not exactly have altitude layers at 10, 100 and 300 m to compare to BAO; therefore, the model wind was extracted at 3, 105 and 325 m, respectively, which represent the values closest to the BAO tower altitudes. The results are shown in FIGS. 21A-21C.

The error component due to wind direction was actively minimized using the spatial information contained in the mobile SOF data. The wind direction is constrained by the direction of the plume evolution from the sites and measurements of VCD column enhancements downwind. It was determined that the model wind direction for site 1 is representative of the actual wind direction, whereas for sites 2 and 4 the wind direction was corrected by $7/23$ and $11/18°$ for RD10/RD11, respectively. For comparison, the wind direction at BAO agrees to <40° on 12 and 13 Aug. 2014. To determine the effect the wind direction uncertainty has on the emission flux, the emission flux was first calculated using the model wind and then compared to the model wind corrected by direction. The bias on the emission flux due to wind direction is 9.3±3.6% for site 2 and 19.0±8.6% for site 4. This bias has been corrected as described above. For the three sites is the correction leads on average to a 9.5±7.8% change in the emission flux.

Figure 21A:
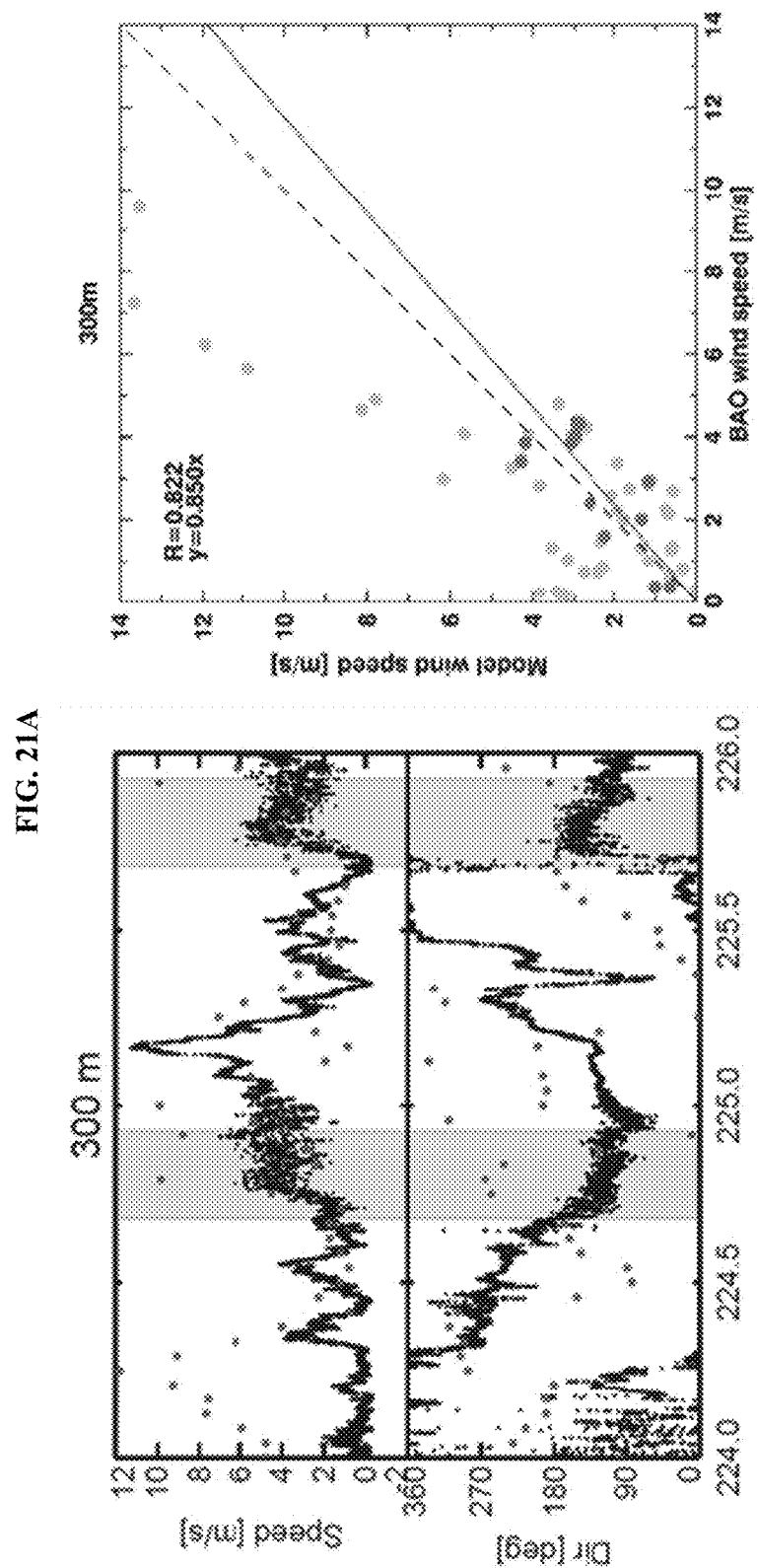
FIGS. 21A-21C are graphs comparing wind speed and wind direction at 300 (top), 100 (middle), and 10 m (bottom). Left graphs: small dots are BAO observed wind, large dots are modeled wind for 12 and 13 Aug. 2014. The colored shading indicates the times of the RDs on both days (16-22 UTC). Right graphs: Darker dots indicates data from 16-22 UTC, lighter dots is all data. The solid line indicates the fit to blue data, the dashed line is the 1:1 line.
Figure 21B:
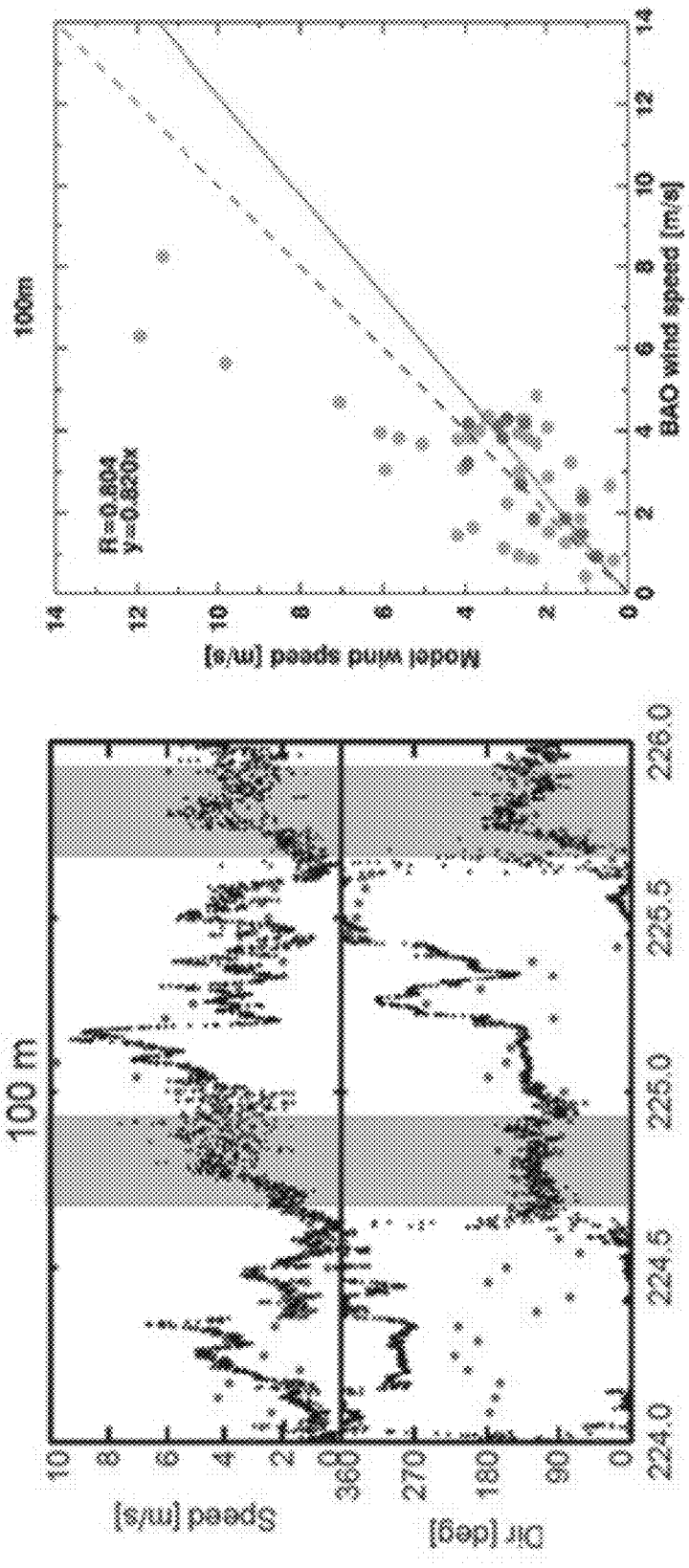
Figure 21C:
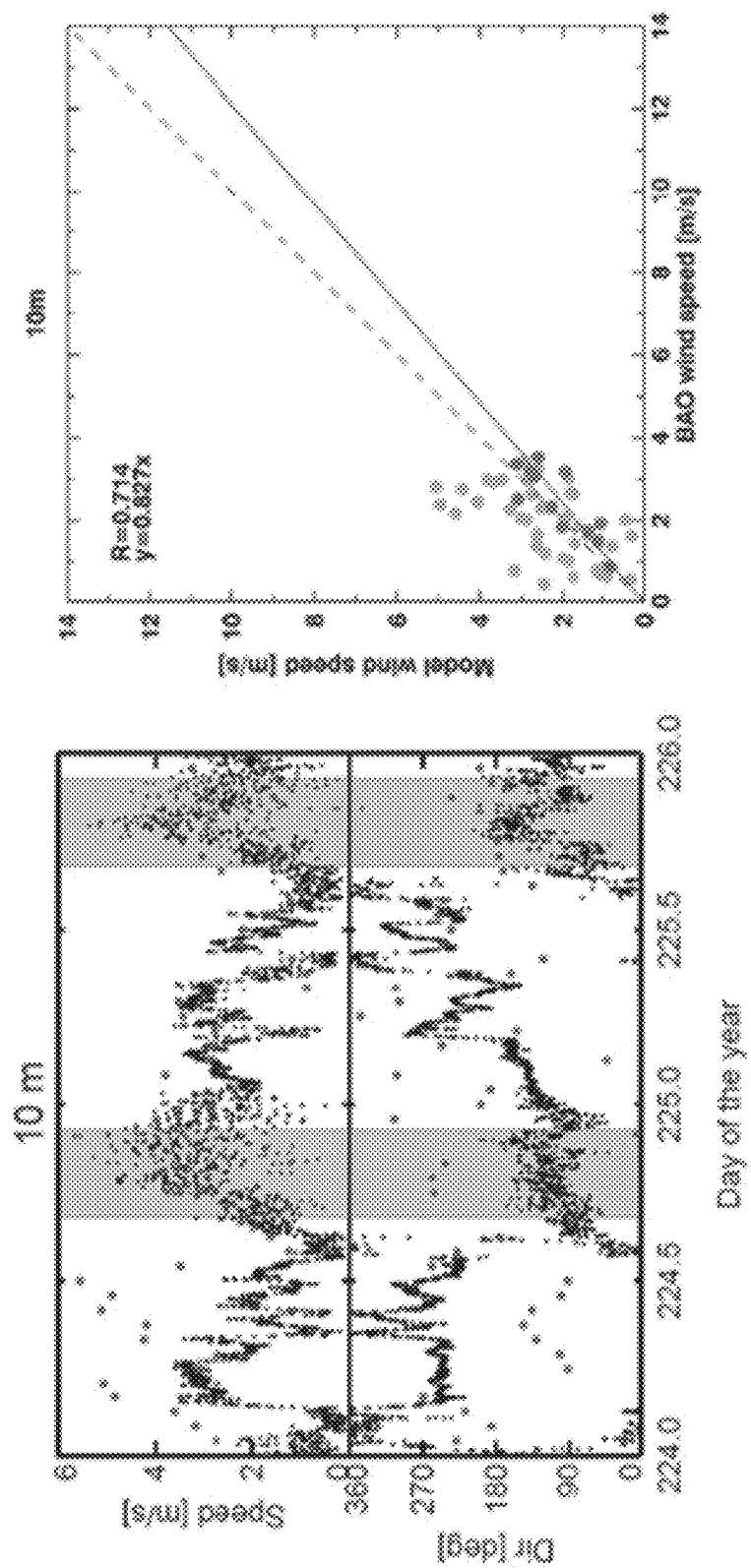

Based on the slopes in FIGS. 21A-21C the wind speed has a percent error of 16.8. There is little variability in the relative differences between measured and predicted wind speed with altitude at BAO, variations are within a few percent. The uncertainty in the emission flux due to the model wind speed was taken as the average difference over the three altitudes within the PBLH, as indicated in the bottom panel of FIGS. 22A-22B.

Vertical plume dispersion determines which altitude to use for averaging the model wind speed. The PBLH varies from ~500 to 2,500 m from the time of driving around site 1 to site 4. The model estimates that most $NH_3$ is located in the lowest 500 m of the VCD. The error due to vertical variability in winds during RD10 and RD11 was 11.2±8.3%. This error falls within the error on wind speed, indicating that the emission flux here is not sensitive to the vertical plume extend.

The combined uncertainty of wind direction and wind speed on the emission flux is 18% for site 1 during both RD10 and RD1 and dominated by the error in the wind speed. For site 2 the total wind uncertainty on emission flux is 17.8±0.5%, and for site 4 the uncertainty is 22.0±3.4%. Based on the evaluation of winds at BAO, and use of the corrected wind direction for each site, the uncertainty in the emission fluxes due to winds is 20%.

The overall uncertainty in the emission fluxes combines the uncertainty of the trace gas VCD measurements (see Table 4) and the model winds. For all gases the error of the trace gas VCD is about a factor 4 smaller than the error due to model winds in the flux calculation (see Eq. 2). The $NH_3$, $NO_2$ and $C_2H_6$ fluxes and the respective overall flux uncertainties calculated from combining the error in the VCD measurements and model winds are discussed below in Example 17.

TABLE 5

$NH_3$, $NO_2$ and $C_2H_6$ flux estimates from 12 Aug. 2014 and 13 Aug. 2014

| | Site | | |
|---|---|---|---|
| | 1 | 2 | 4 |
| Size (km × km) | 1.6 × 1.6 | 1.6 × 1.6 | 1.6 × 1.6 |
| Source type | Dairy | Beef | Dairy |
| Maximum count | unknown | 54,044 | 7,450 |
| $NH_3$ flux (kgh$^{-1}$) - RD10 | 128 ± 26 | 625± | 85 ± 17 |
| $NH_3$ flux (kgh$^{-1}$) - RD11 | 89 ± 18 | 673± | NN$^2$ |
| $NO_2$ flux (kgh$^{-1}$) - RD10 | NN$^2$ | 18± | 1.3 ± 0.3 |
| $NO_2$ flux (kgh$^{-1}$) - RD11 | NN$^2$ | 11 ± 2 | −2.5 ± 0.5$^3$ |
| $C_2H_6$ flux (kgh$^{-1}$) - RD10 | 37 ± 8$^3$ | NN$^2$ | NN$^2$ |
| $C_2H_6$ flux (kgh$^{-1}$) - RD11 | 90 ± 19$^3$ | NN$^2$ | NN$^2$ |

[1]Source: Colorado Department of Public Health and Environment: CAFO locations and maximum capacities for FRAPPE.
[2]NN indicates no number; significant influence from upwind sources precluded quantification.
[3]Influence from upwind sources was non-negligible.

The absolute values of the difference between the VCDs averaged over identical time intervals measured by the HR-NCAR-FTS and by the mobile SOF were used to quantify accuracy. The results are presented in Table 4. The findings for measurement precision and accuracy result in the following LODs: $LODNH_3 = 0.10 \times 10^{16}$ molecules/cm$^2$ and $LODC_2H_6 = 0.13 \times 10^{16}$ molecules/cm$^2$. The accuracy is composed of uncertainty in the cross section, the error associated with the spectral fit and the uncertainty on the retrieved VCD due to the ILS effect (see Example 13). With an accuracy of 6.1% for $NH_3$ and 9.0% for $C_2H_6$ and the above given LOD values this means that the accuracy is limiting the overall uncertainty in trace gas observations at concentrations greater than $2.27 \times 10^{16}$ for $NH_3$ and $1.94 \times 10^{16}$ molecules cm$^{-2}$ for $C_2H_6$. During FRAPPE, the VCDs were greater than the LOD in 99.98% for $NH_3$ and 100% for $C_2H_6$ of the measurements, which means the LOD was an issue in a low amount of measurements. In terms of the total error (see Table 4), this means that the uncertainty was determined by the accuracy of the observed median and maximum and the LOD was limiting the uncertainty on the minimum observed VCD. For a median VCD of $4.32 \times 10^{16}$ molecules cm$^{-2}$ for $NH_3$ the uncertainty is $0.19 \times 10^{16}$ molecules cm$^{-2}$, and for a median VCD of $3.49 \times 10^{16}$ molecules cm$^{-2}$ for $C_2H_6$ the uncertainty is $0.23 \times 10^{16}$ molecules cm$^{-2}$.

Example 15: Structure Function

Figure 23A:
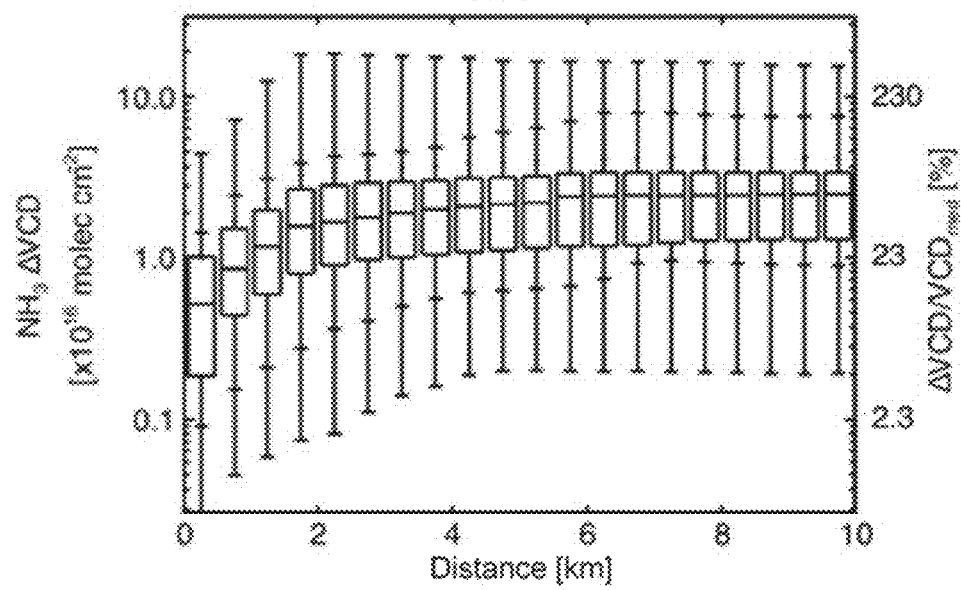
FIGS. 23A-23C are graphs of structure functions of (a) $NH_3$, (b) $C_2H_6$ and (c) $NO_2$ using data from RD11 with a time constraint of 30 min for the time period of the five sites. The bin width is 500 m. Boxes mark 25th and 75th percentiles, the dot indicates the mean and the line inside the box marks the median. Dashes below and above the boxes indicate 5th, 15th, 85th and 95th percentile.
Figure 23B:
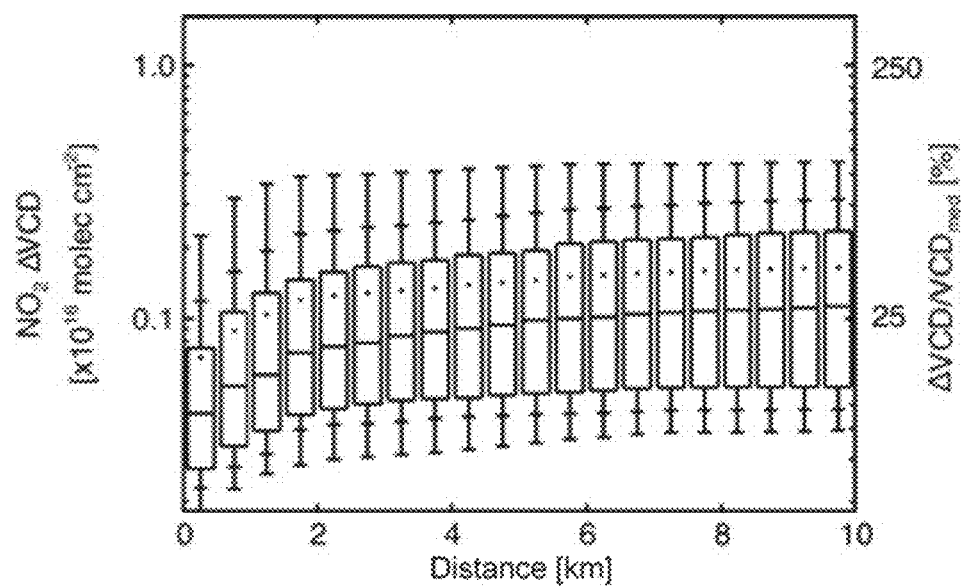
Figure 23C:
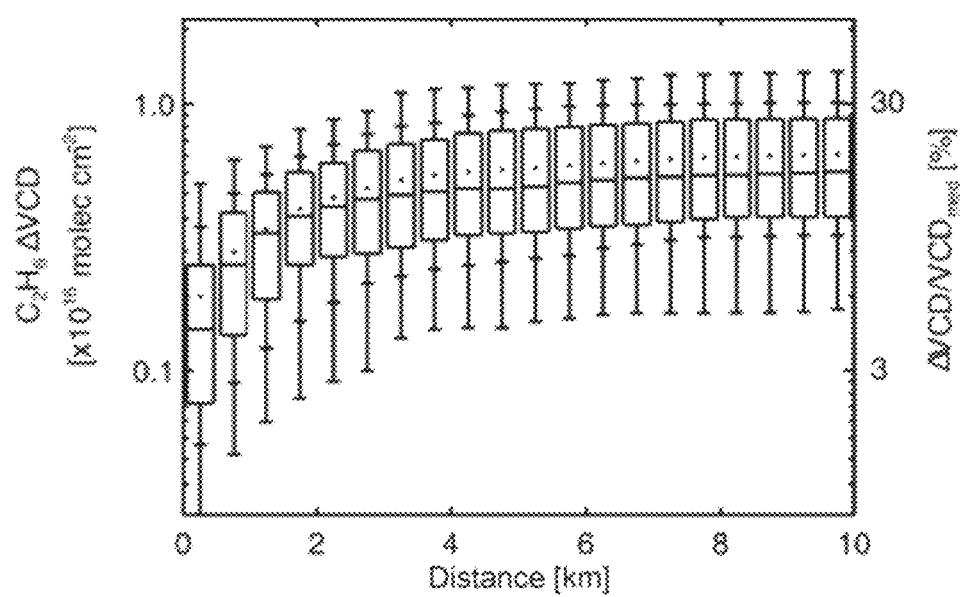

The structure function to assess the spatial scales of VCD variability is defined as $$f(Z,y) = \langle |Z(x+y) - Z(x)|^q \rangle \qquad (3)$$

where < > denotes the average difference in VCD within distance y, Z is the VCD of a gas of interest, and q is a scaling exponent. Setting q equal to 1 this structure function is a useful tool to quantify trace gas variability over horizontal distance. At small distances between measurements the structure function exhibits the largest rate of change and increases until converging at larger distances. Variabilities increase as both plumes and background air masses are observed. At a certain spatial distance the structure function converges against a maximum VCD variability. The variability length scale was defined to determine over which spatial scales a certain percentage of the maximum median variability is observed. The spatial distance at which the VCD variability is 50% of the maximum variability is denoted as $L_V$ (50%). Then $$L_V(P) = d(P \cdot V_{max}) \qquad (4)$$

where $L_V$ denotes the variability length scale for a certain percentage P and $d(P \cdot V_{max})$ denotes the distance in kilometers at which the VCD variability equals $P \cdot V_{max}$. Here, $V_{max}$ is the maximum median variability. FIGS. 23A-23C show the structure function with units of distance in kilometers on the abscissa, VCD difference has units of molecules cm$^{-2}$ on the ordinate, and a second ordinate scales the VCD difference with respect to the median VCD.

Example 16: Mobile SOF Deployment

The mobile SOF was deployed during 16 RDs during FRAPPE. Data is presented from two RDs that were conducted along almost identical drive tracks on consecutive days as well as shared common scientific objectives. The drive track for the case study from 13 Aug. 2014 is shown in FIG. 20 and is similar to the drive track on 12 Aug. 2014. The five sites indicated in that figure contain feedlots (and probably oil and natural gas storage tanks). On 12 and 13 Aug. 2014, RD10 and RD11, respectively, the following median (minimum, maximum) VCDs were observed: 4.3 (0.5, 45) for $NH_3$, 3.5 (1.5, 7.7) for $C_2H_6$ and 0.4 (0.06, 2.2)×10$^{16}$ molecules cm$^{-2}$ for $NO_2$.

Figure 22A:
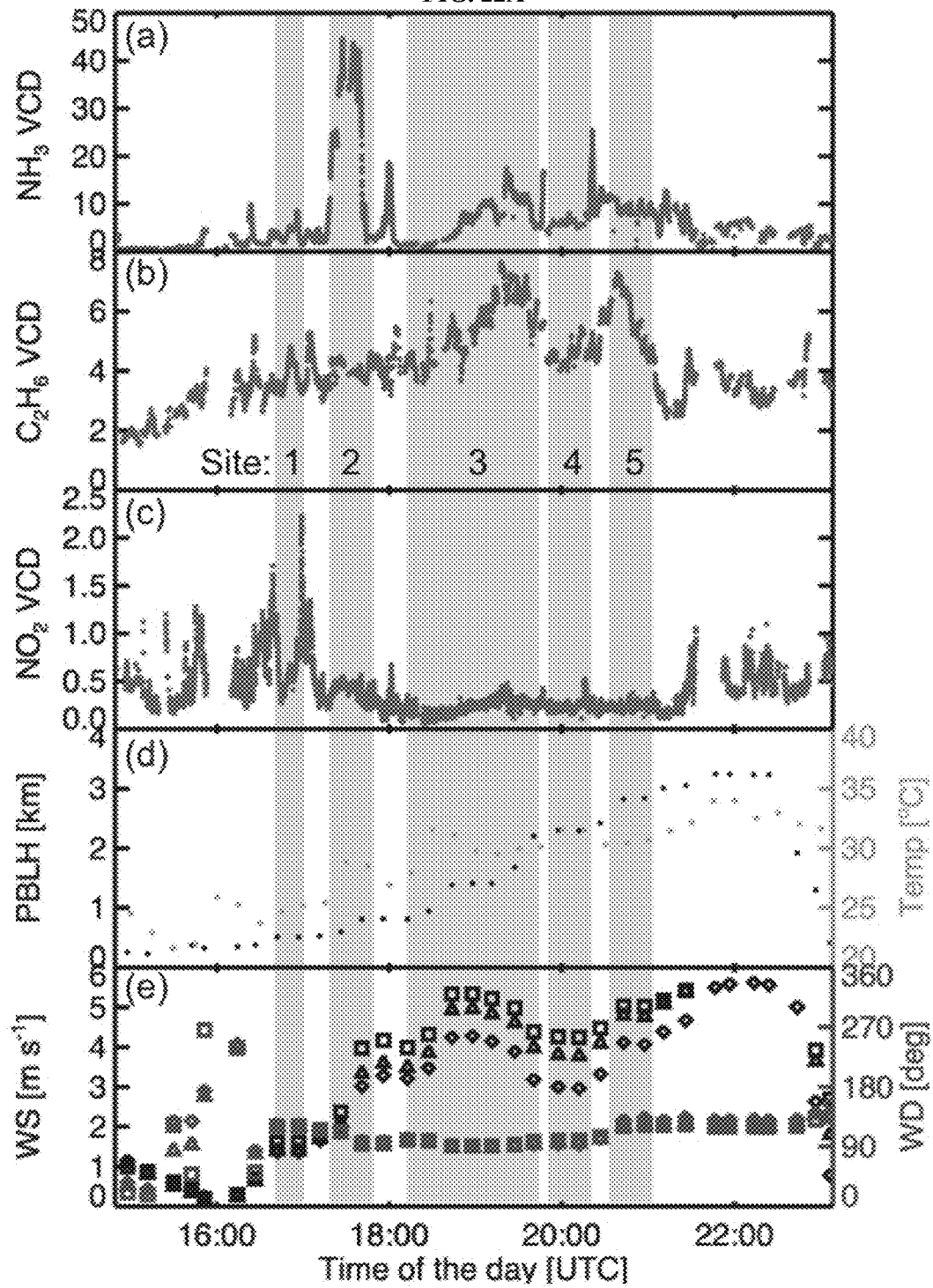
FIGS. 22A-22B are graphs of time series of the VCDs (1,016 molec cm$^{-2}$) measured for (a) $NH_3$, (b) $C_2H_6$ and (c) $NO_2$ during RD11 (FIG. 22A) and RD10 (FIG. 22B). (d) PBLH and temperature. (e) Model wind speed and model wind direction averaged over approximately 10-50 m above ground level (diamonds), over half PBLH (triangles) and over the full PBLH (squares). Shaded areas indicate times at each site marked on FIG. 21.
Figure 22B:
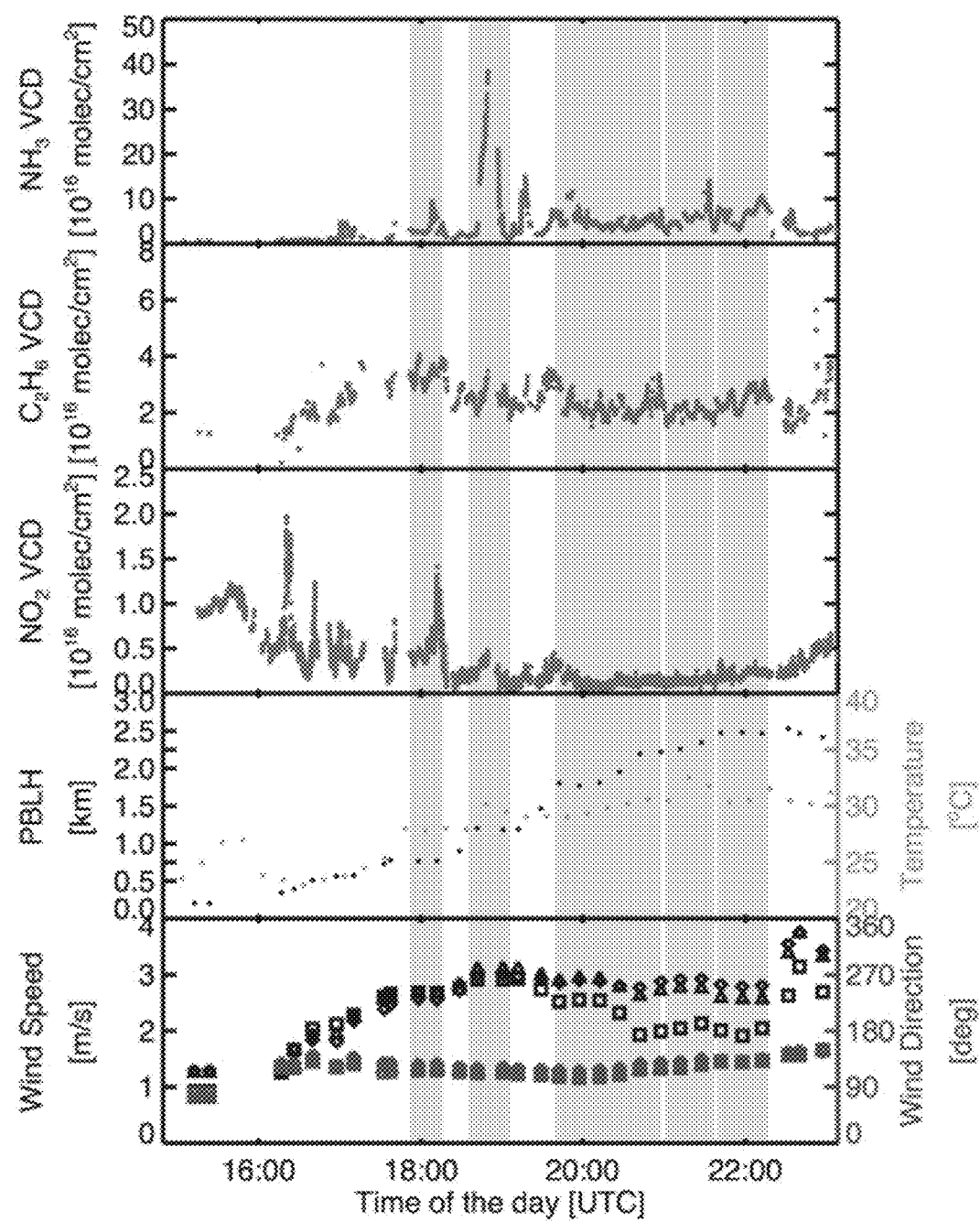
Figure 24A:
FIGS. 24A-24C are maps depicting the drive track of RD11, color coded by the VCD of $NH_3$ (left maps), $C_2H_6$ (middle maps) and $NO_2$ (right maps).
Figure 24B:
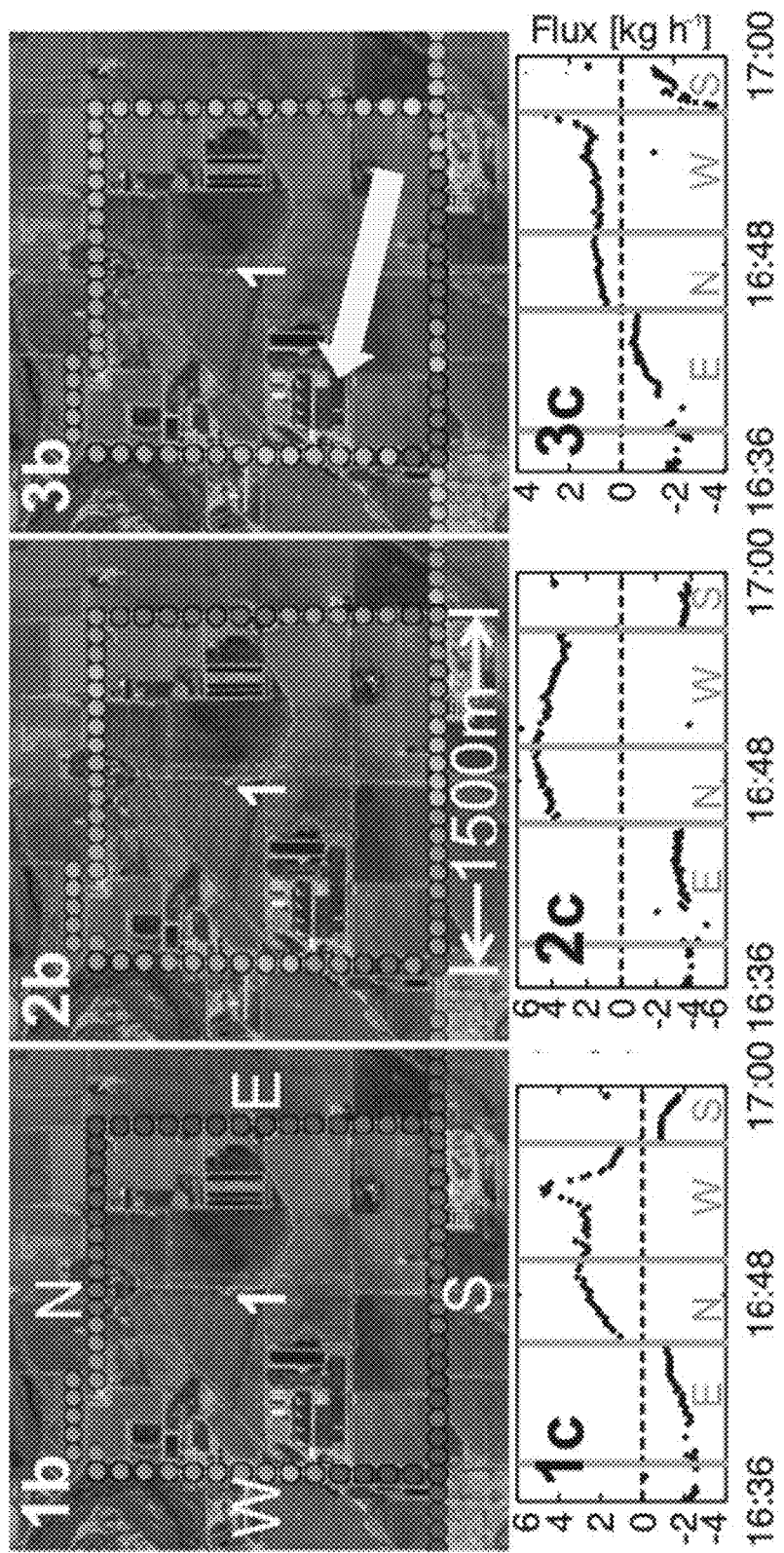
Figure 24C:
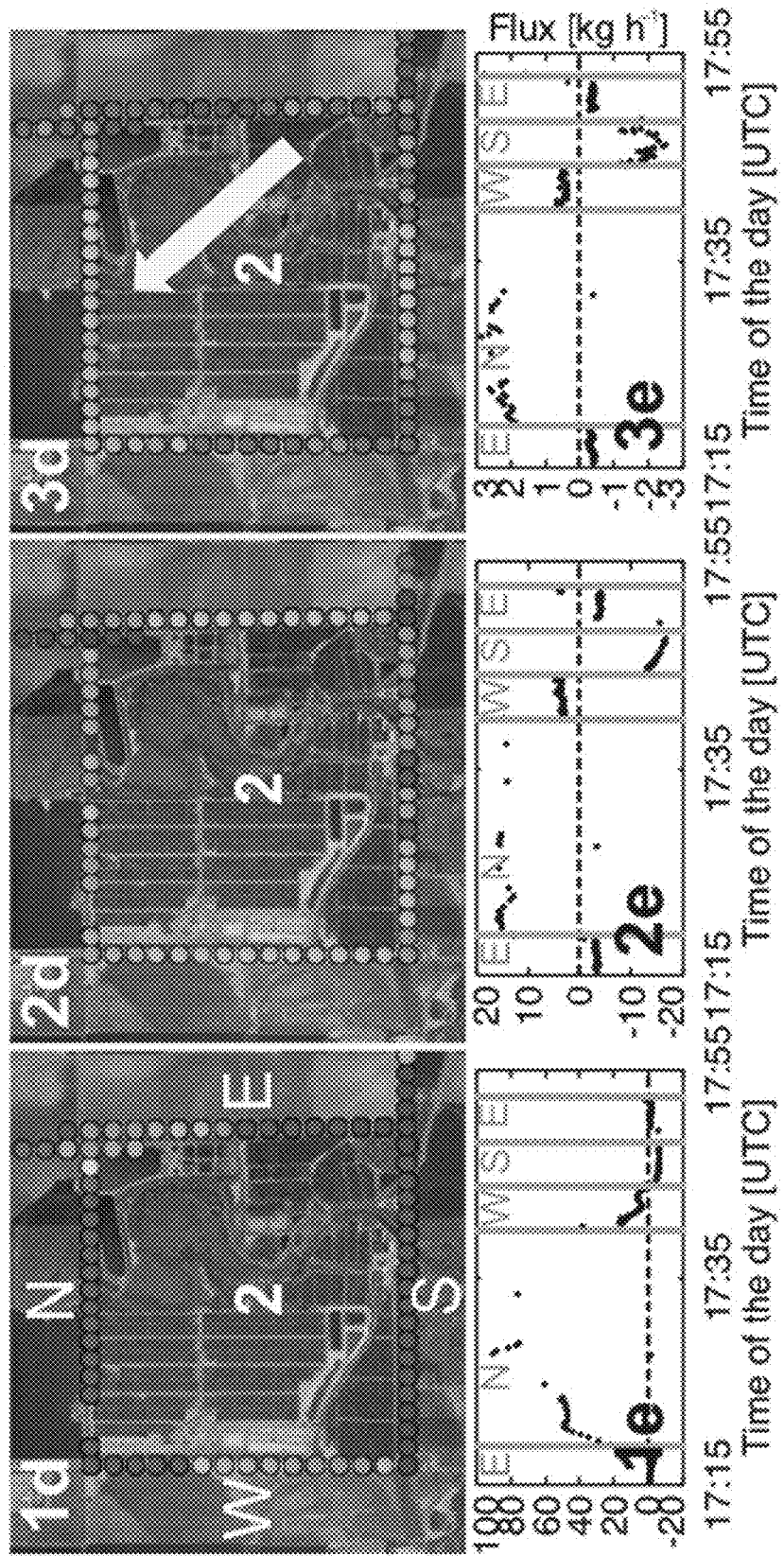
Figure 25A:
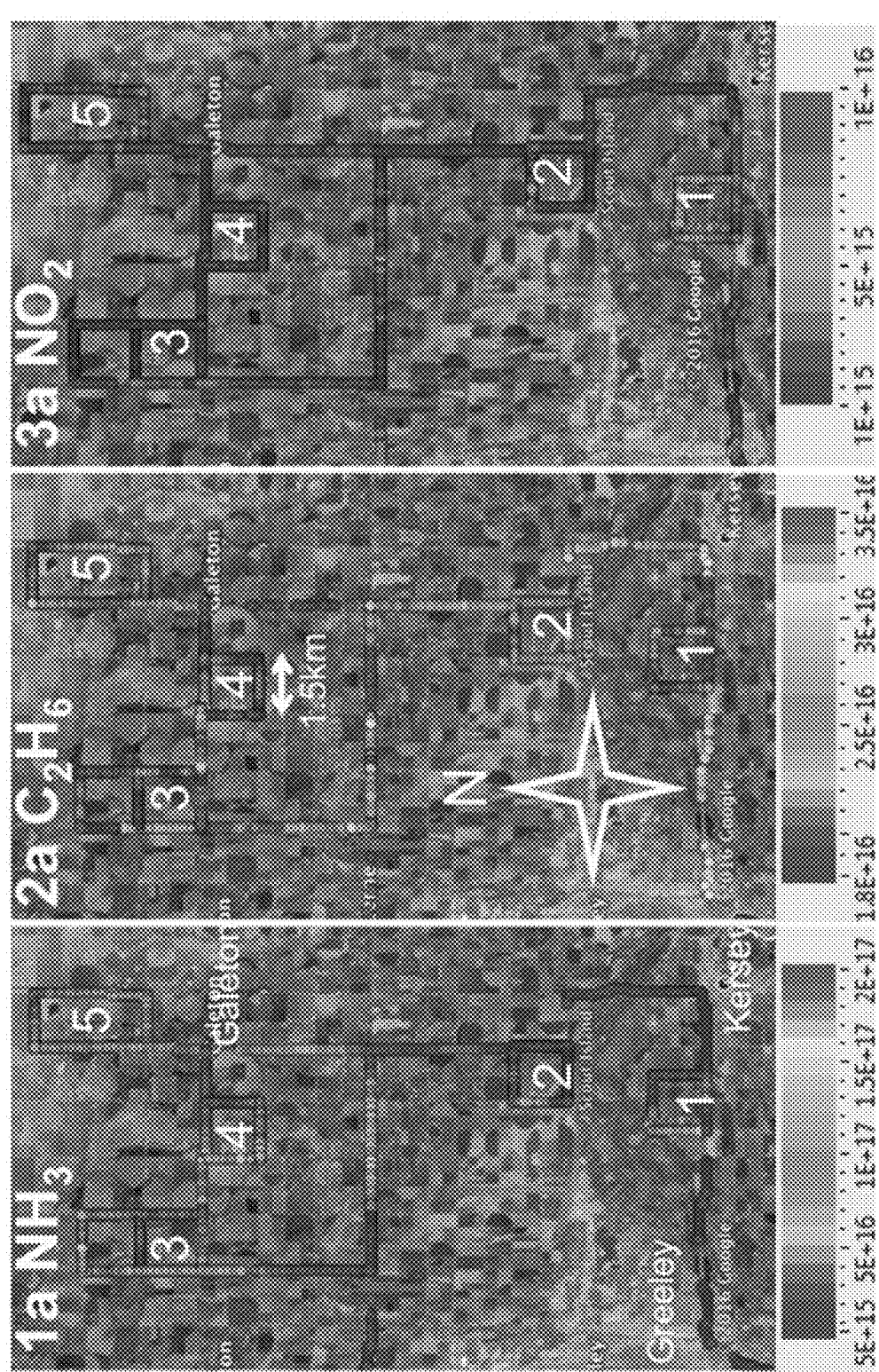
FIGS. 25A-25C are maps depicting the drive track of RD10, color coded by the VCD of $NH_3$ (left maps), $C_2H_6$ (middle maps) and $NO_2$ (right maps).
Figure 25B:
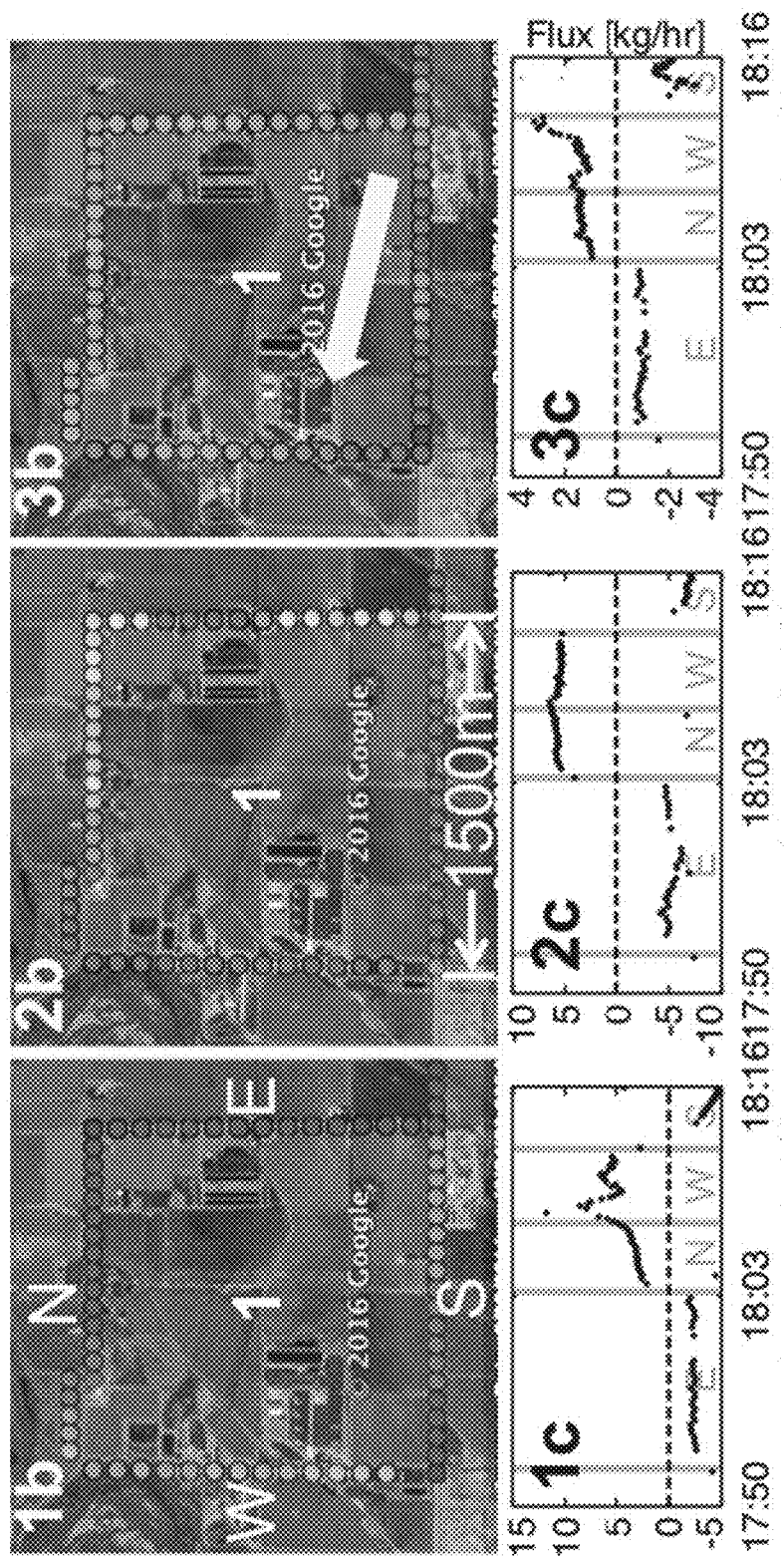
Figure 25C:
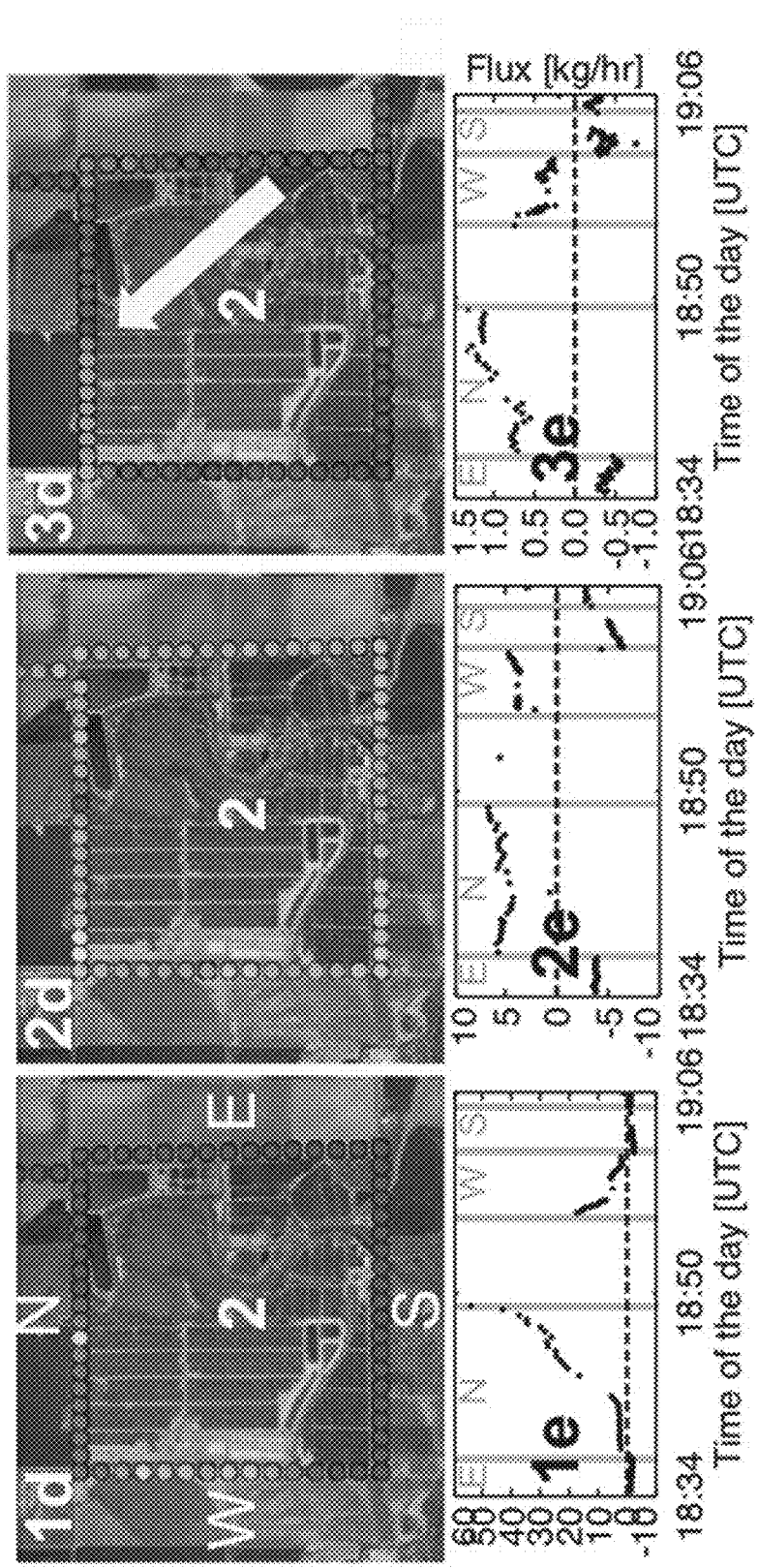

The variability in total column densities during RD11 is shown in FIG. 22A and FIGS. 24A-24C. The analogous figures for RD10 are shown in FIG. 22B and FIGS. 25A-25C. Both RDs show similar features in VCD enhancement (VCD-VCD background/of the gases, temperature and wind. FIG. 22A shows the VCD time series of the three gases, a time series for the temperature and PBLH, and the model wind speed and direction. $NH_3$ shows significant column enhancement for site 2, which was the concentrated animal feeding operation (CAFO) with ~54 000 cattle. $NO_2$ also shows some VCD enhancement for site 2. FIGS. 24A-24C show the VCD time series in form of a GOOGLE® Earth visualization to indicate the spatial distribution. Sites 1 and 2 are also shown enlarged to visualize the downwind and upwind effects. Site 1 is a source for both $NH_3$ and $C_2H_6$. There is a dairy farm located near the west end of the site and a source for $C_2H_6$ in the upper right of the site. The VCD enhancement of $NO_2$ at the south leg of the site is due to heavy traffic on that street. Site 2 for $NH_3$ shows the column enhancement downwind of the cattle feedlot and a background VCD upwind of the cattle feedlot. For that same site $NO_2$ shows a larger column enhancement downwind than upwind. $C_2H_6$ is mostly transported through site 2, as can be seen in that the VCD is on the same color scale upwind and downwind of site 2.

Example 17: Emission Fluxes

Emission fluxes were calculated as described in Example 14. The wind used for flux calculations has been averaged within the planetary boundary layer (FIG. 22A). FIGS. 24B and 24C show the flux as time series for each site. The stretch downwind of a site shows positive flux values if the site is a source. If the site is not a source, and a gas is passing through the site, then the absolute value of negative incoming flux and positive outgoing flux are expected to be comparable.

The calculated net fluxes are presented in Table 5 for RD10 and RD11. It was verified that cattle and dairy farms in sites 1, 2 and 4 are significant sources for $NH_3$ and that the CAFO soil in site 2 is a significant source of $NO_R$, which had been observed in terms of a positive $NO_2$ production rate. The numbers in Table 5 reflect the uncertainty of the spectroscopic data and the wind data. The error due to the atmospheric variability is not accounted for explicitly in these error bars.

$NH_3$ Fluxes

For sites 1, 2 and 4, the dairy and cattle feedlots are a source of NH3 during both RDs. The emission flux in site 2 with the largest head count of cattle shows agreement of better than 10% for RD10 and RD11. The average flux is $649\pm24$ kg $NH_3$ h$^{-1}$ for 54,044 cattle. This consistency between two days gives confidence that the uncertainty in the wind is conservatively estimated here. The average emission factor for site 2 is $12.0\pm2.8$ g $NH_3$ h$^{-1}$ head$^{-1}$ for both days during daytime in the summer. The uncertainty here combines the day-to-day variability and error in the wind (taken as $30\%/\sqrt{2}$). For the dairy farm in site 4 a value of $11.4\pm3.5$ g $NH_3$ h$^{-1}$ head$^{-1}$ was obtained. The per head emission flux from the two samples at site 2 and one sample at site 4 can be pooled resulting in an average emission factor of $11.8\pm2.1$ g $NH_3$ h$^{-1}$ head$^{-1}$. The head count for site 1 was unknown but can be estimated based on the pooled per head emission. The average emission flux from site 1 of 108 kg h$^{-1}$ corresponds to 9,200 cattle. During RD11 the upwind effect influenced the observed VCD at site 4 and precluded quantification of a flux. This means the upwind flux was significant, and variability during the course of driving around the site may have influenced the observed flux.

$NO_2$ Production Rates

Soils are sources of $NO_R$, which is primarily emitted as NO as a result of microbial activity $NO_2$ is subsequently produced from the reaction $NO+O_3=NO_2+O_2$ in the atmosphere. Both RDs consistently showed site 2 is a significant source of $NO_R$, with an average measured $NO_2$ production rate of 14.5 kg h$^{-1}$. The difference in the $NO_2$ emission flux from 18 kg h$^{-1}$ during RD10 and 11 kg h$^{-1}$ during RD11 may represent differences in wind speed. During RD10 the wind speed was approximately 1 to 2 ms$^{-1}$ slower than on RD11 (compare FIGS. 22A and 22B), allowing for less time for NO into $NO_2$ conversion during transport. The reaction rate constant for the above reaction is $k=3.0\times10^{-12}\times e^{-1500/T}$ cm$^3$ molec$^{-1}$ s$^{-1}$, which at a temperature of 300 K corresponds to a value for the rate constant of $2.02\times10^{-14}$ cm$^3$ molec$^{-1}$ s$^{-1}$ during the case studies. On RD10 and RD11, $O_3$ concentrations of 64 and 68 ppb at 19:00 and 18:00 UTC, respectively, correspond to a NO lifetime of ~40 s (66 ppbv $O_3$). With wind speeds of ~4 ms$^{-1}$ NO was converted into $NO_2$ over a distance of ~160 m (RD11). In particular, there is sufficient time to convert most of the NO emissions into $NO_2$ within the CAFO area of $1.6\times1.6$ km$^2$. To estimate the $NO_2$/NO ratio under photostationary state, photochemical destruction of $NO_2$ from the reaction $NO_2+O_2 \rightarrow (h\nu) NO+O_3$ needs to be taken into account. Assuming a typical photolysis frequency, $J(NO_2)$, as ~$8\times10^{-3}$ s$^{-1}$, the $NO_2$/NO ratio is 3.6, indicating that ~80% of $NO_x$ is abundant as $NO_2$. The average measured $NO_2$ production rate thus corresponds to a $NO_x$ emission rate of $18.6\pm7.4$ kg h$^{-1}$ for site 2. For a fraction of the nearby soil emission there may not be sufficient time to reach the photochemical steady state, but this fraction is likely small.

It was determined that the $NO_x$ was originating from the feedlot soil rather than point sources such as diesel generators or trucks. Based on Gaussian plume modeling a source point that is at a distance of 1.7 km from the measurement location (greatest distance of downwind measurement to a potential diesel generator for the beef feedlot at site 2) can have dispersed horizontally up to 300 m. $NO_2$ column enhancement was measured over a distance greater ~1.4 km, indicating that the source of $NO_x$ is the entire feedlot area.

$C_2H_6$ Fluxes $C_2H_6$ has a relatively long atmospheric lifetime of about 2 months and is lost in the reaction with OH: $OH+C_2H_6 \rightarrow C_2H_5+H_2O$. Assuming an OH concentration of $8\times10^6$ molecules cm$^{-3}$ and taking the OH reaction rate constant of $2.4\times10^{-13}$ cm$^3$ molec$^{-1}$ s$^{-1}$, the lifetime of $C_2H_6$ is 60 days, which gives rise to a Northern Hemisphere (NH) background VCD of, for example, $3.1\times10^{16}$ molecules cm$^{-2}$ at Kiruna, Sweden (Angelbratt et al., Atmos. Chem. Phys., 11, 9253-9269, 2011). $C_2H_6$ VCD enhancements over the NH background are therefore expected to mix on regional scales and are subject to significant transport in the atmosphere. The RDs measured the lowest VCDs of $C_2H_6$ in Boulder County, Colo. with its moratorium on fracking. Enhanced VCDs were observed throughout Weld County, Colo., in areas with active oil and natural gas (ONG) production. Using all 16 RDs, the median (minimum, maximum) VCDs in Boulder County and Weld County were 1.5 (0.5, 3.1)$\times10^{16}$ and 3.5 (1.0, 10)$\times10^{16}$ molecules cm$^{-2}$, respectively. The influence from upwind sources makes the quantification of C2H6 emission fluxes a bit more challenging. A positive emission flux was consistently quantified out of site 1, as shown in Table 5. Site 1 was also influenced from upwind sources, but the mean $C_2H_6$ flux was calculated as 63.5 kg h$^{-1}$ with an uncertainty of 29 kg h$^{-1}$.

Example 18: Aerial Mounted Devices SOF Device

Figure 26A:
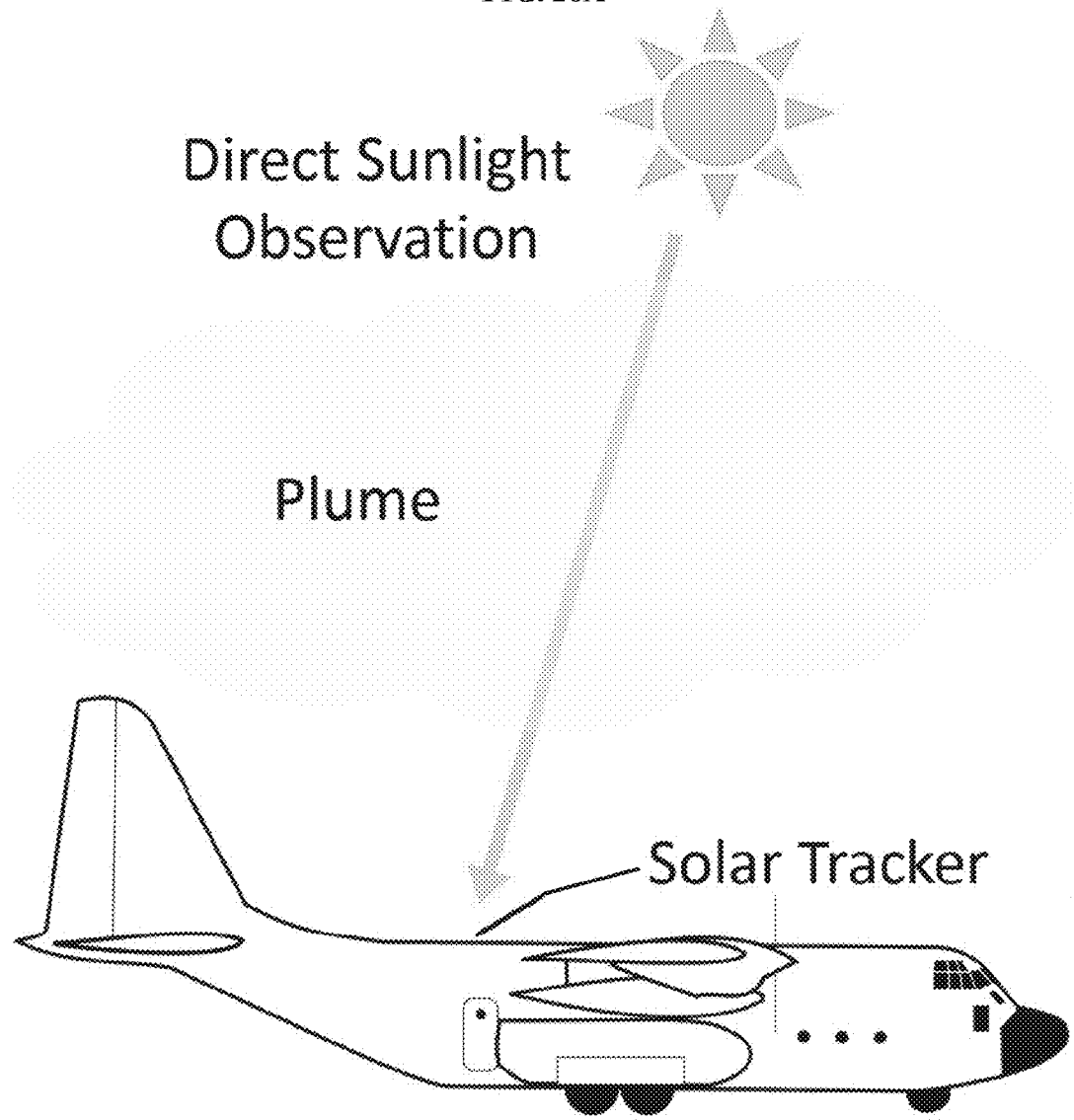
FIG. 26A is a schematic of the mobile SOF mounted aboard a C-130.
Figure 26B:
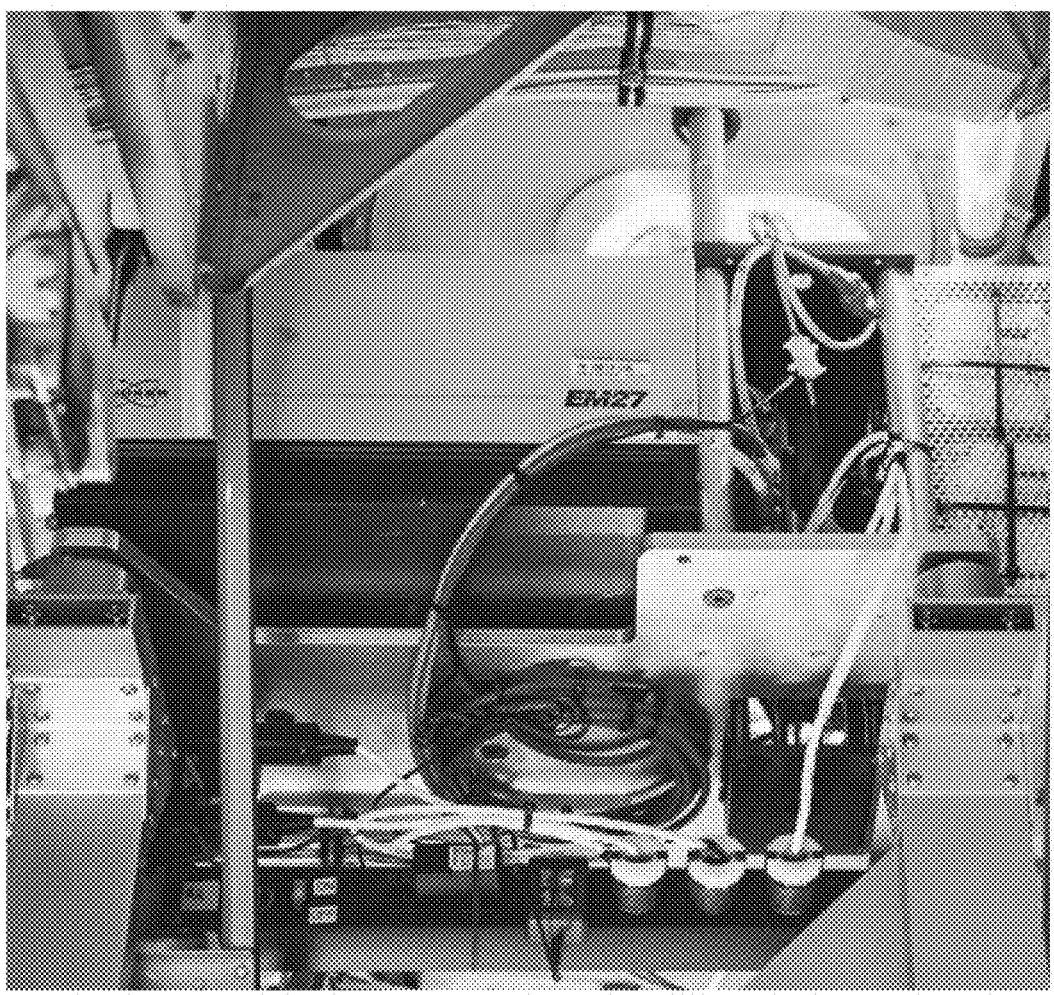
FIG. 26B is a photograph of the SOF device aboard the C-130 during the Airborne Research Instrumentation Testing Opportunity (ARISTO) 2016.
Figure 27A:
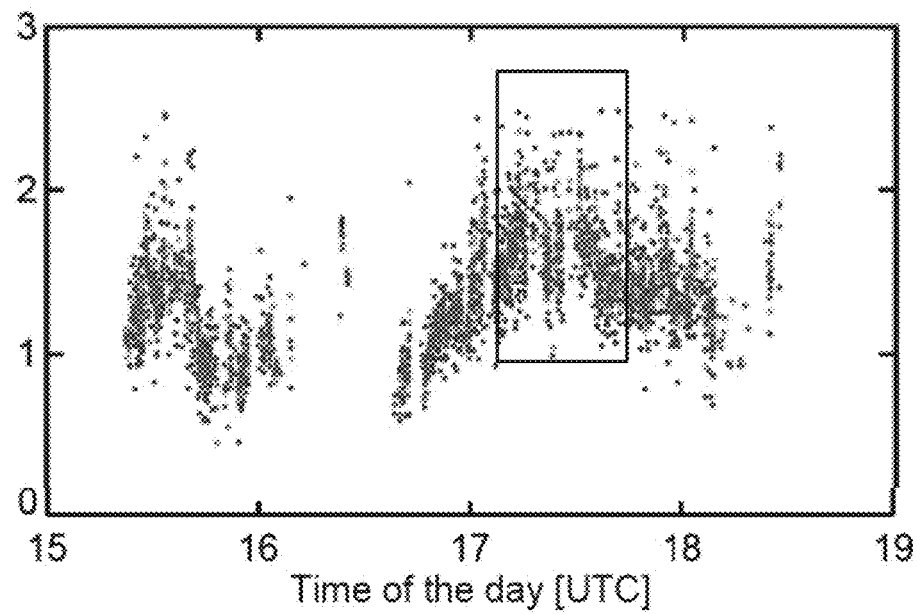
FIG. 27A is a graph of a time series of VCD data recorded from the C-130 mounted SOF device. The boxed section is shown in detail in FIG. 27C.
Figure 27B:
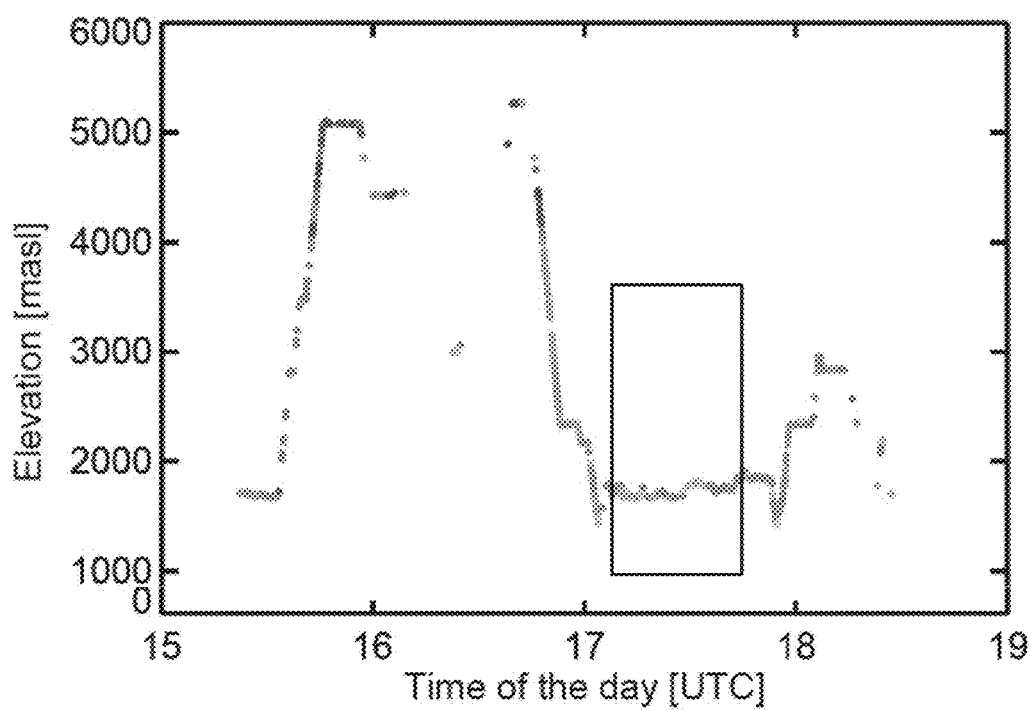
FIG. 27B is a graph of color-coded VCD as a function of elevation.
Figure 27C:
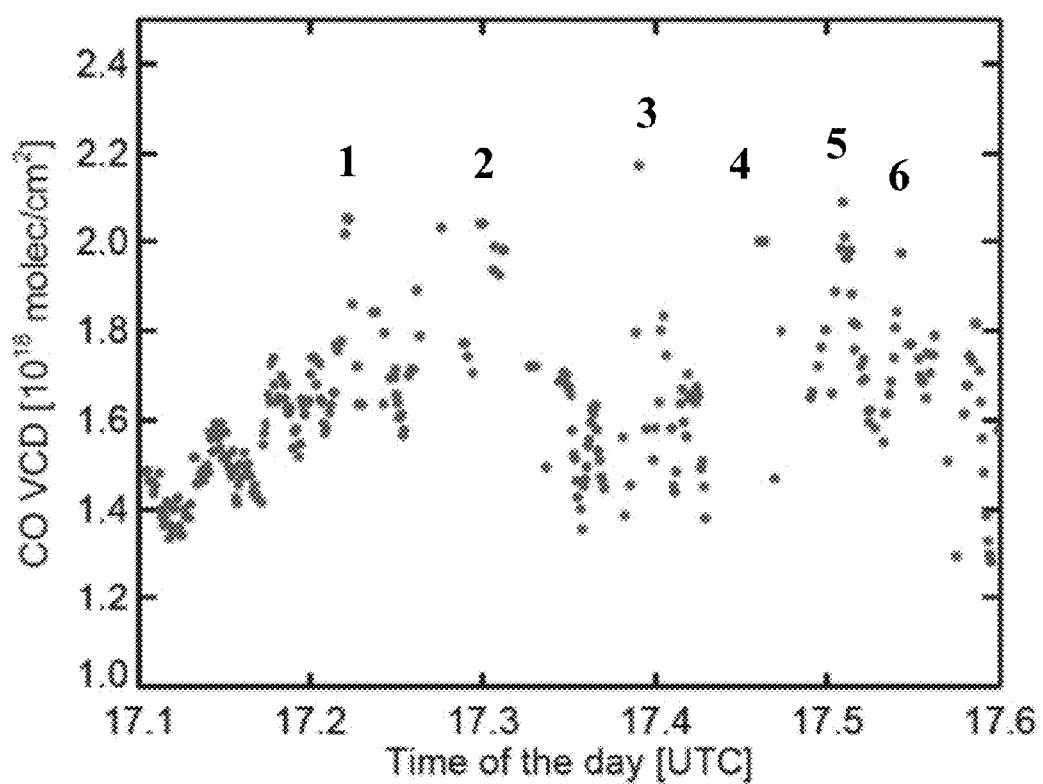
FIG. 27C is a detailed graph of the portion of FIG. 27A outlined by the box. Elevated VCDs were recorded during this portion of the flight, due to an upwind burning event. The numbered time points correspond to numbered locations in FIG. 28.
Figure 28:
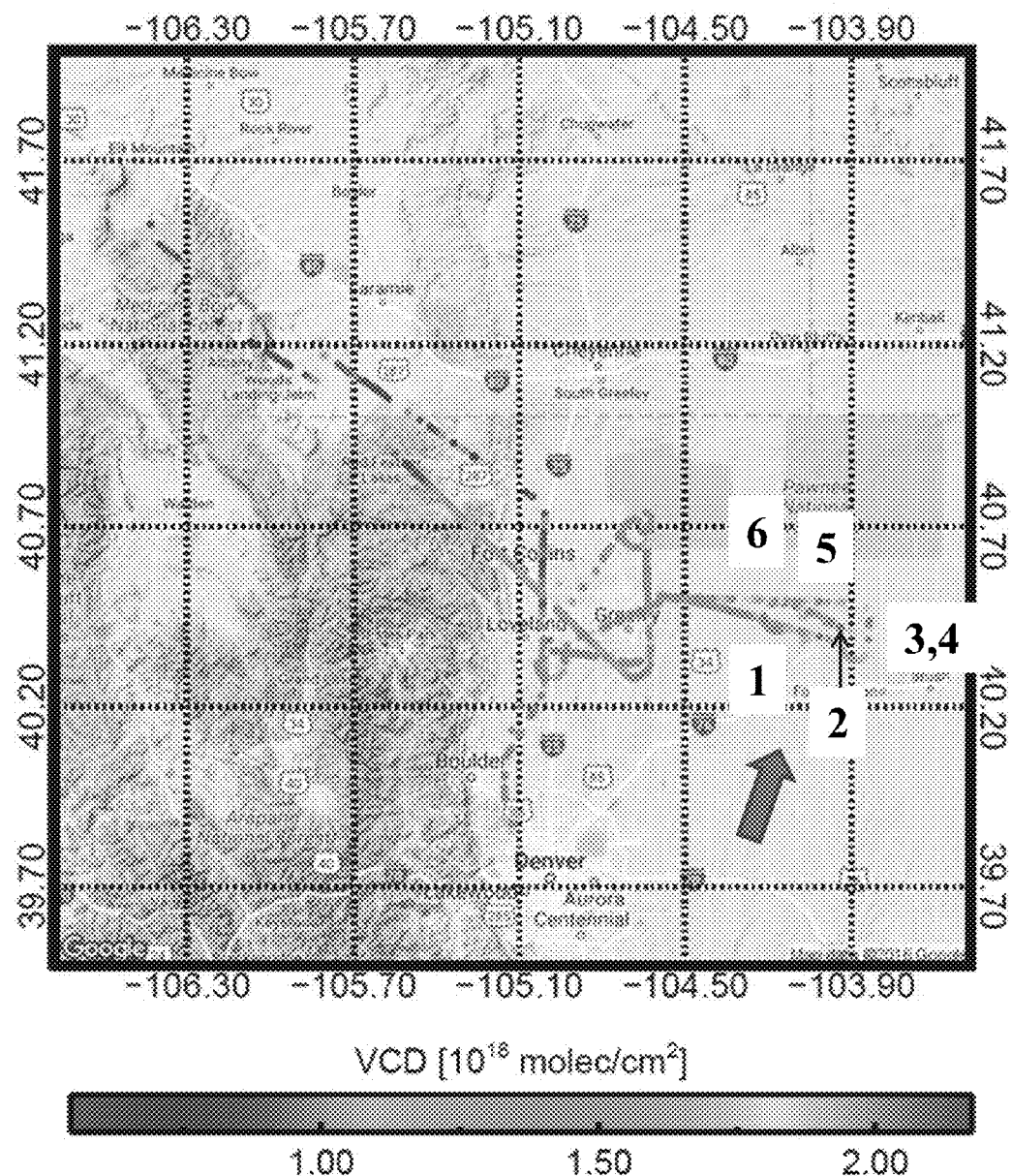
FIG. 28 is a map of the flight path of the Airborne Research Instrumentation Testing Opportunity (ARISTO) 2016 test. Elevated VCDs were recorded at the numbered locations (1-6) in the southeastern portion of the map due to an upwind burning event. The arrow identifies the average wind direction.

The device described in Example 10 was mounted on a C-130 aircraft (FIGS. 26A-26B) and tested analogously to the ground vehicle mounted devices described elsewhere herein. The aerial mounted SOF was compared to NCAR data as described in Example 12. Vertical column density was measured over the period of the test flights and averaged every 5, 15 and 25 seconds (FIGS. 27A-27C). The path of the experimental flight conducted on 10 Aug. 2016 is shown in FIG. 28. During this flight, elevated VCDs were recorded downwind of a burning event near Fort Morgan, Colo., marked on FIG. 28 as points 1-6.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A mobile radiation disk light source tracker system mounted on a platform, the system comprising:
    a first stepper motor and a second stepper motor;
    a first mirror, wherein the first mirror is mounted at a 45° angle on the first stepper motor;
    a second mirror, which is mounted at a 45° angle opposite from the first mirror; and wherein the first and second mirrors are mounted onto a rotational stage that is coupled with the second stepper motor, wherein the rotational stage allows for 360° rotation of the first and second mirrors;
    a lens and an aperture plate, which are set up such that light source incoming radiation that is reflected by the first mirror onto the second mirror is then reflected by second mirror onto the lens, wherein the lens focuses the incoming radiation disk onto a front side of the aperture plate;
    a motion compensation system that measures in real time the pitch, roll and heading information (Euler Angles) of the platform, which is used to calculate the light source position relative to the platform in real time;
    an imaging monitoring system that is capable of measuring the position of the incoming radiation disk focused onto the front side of the aperture plate,
wherein the first and second stepper motors are controlled to ensure that the incoming radiation focused onto the front side of the aperture plate is within the imaging device's field of view.

2. The mobile radiation tracker system of claim 1, wherein the light source is selected from the group consisting of the Sun, the Moon, and an artificial disk-like light source.

3. The mobile radiation tracker system of claim 2, wherein the light source is the Sun.

4. The mobile radiation tracker system of claim 1, wherein the monitoring system is a camera.

5. The mobile radiation tracker system of claim 1, wherein an UV-vis spectrometer is located on the opposite side of the aperture plate.

6. The mobile radiation tracker system of claim 5, wherein a diffuser is located between the opposite side of the aperture plate and the UV-vis spectrometer.

7. The mobile radiation tracker system of claim 1, wherein a dichroic mirror is located between the second mirror and the lens, and wherein the dichroic mirror is positioned at an angle of 45° with respect to the incoming beam.

8. The mobile radiation tracker system of claim 7, wherein the dichroic mirror directs infrared radiation to a IR spectrometer.

9. The mobile radiation tracker system of claim 1, wherein the motion compensation system comprises at least one angle sensor.

10. The mobile radiation tracker system of claim 9, wherein the at least one angle sensor comprises a GPS-based inertial navigation system and/or an inclinometer.

11. A method of tracking an incoming radiation disk light source position on a continuous basis from a platform, the method comprising monitoring the position of the light source from the platform using the mobile radiation tracker of claim 1.

12. A computer-implemented method of operating the mobile tracker system of claim 1, the method comprising:
    using heading, pitch and roll angle (Euler Angles) information of the platform to calculate an incoming radiation disk light source position relative to the platform orientation in real time; and
    controlling the first and second stepper motors such that the incoming radiation focused onto the front side of the aperture plate is within the imaging device's field of view.

13. The computer-implemented method of claim 12, wherein determining if the incoming radiation focused onto the front side of the aperture plate is within the imaging device's field of view comprises recording and evaluating incoming radiation disk images to determine the relative center positions of the aperture and the incoming radiation disk.

14. The computer-implemented method of claim 13, further wherein a threshold is applied to convert incoming radiation disk images to binary format contours.

15. The computer-implemented method of claim 14, wherein the incoming radiation disk images are distinguished from the aperture plate and aperture which are not exposed to the incoming radiation.

16. The computer-implemented method of claim 14, further wherein the binary format contours are subjected to an ellipse- or circle-fitting algorithm.

17. The computer-implemented method of claim 16, wherein the position of the fitted ellipse or circle center is determined relative to the aperture.

18. The computer-implemented method of claim 16, wherein the position of the fitted ellipse or circle center relative to the aperture is corrected for any motion observed between measurements.

19. The computer-implemented method of claim 18, wherein the relative position of the fitted ellipse or circle center is used to optimize the light source tracking precision.

* * * * *